United States Patent
Yamanaka et al.

(10) Patent No.: US 8,048,999 B2
(45) Date of Patent: Nov. 1, 2011

(54) NUCLEAR REPROGRAMMING FACTOR

(75) Inventors: Shinya Yamanaka, Kyoto (JP);
Kazutoshi Takahashi, Kyoto (JP);
Keisuke Okita, Kyoto (JP)

(73) Assignee: Kyoto University (JP)

( * ) Notice: Subject to any disclaimer, the term of this patent is extended or adjusted under 35 U.S.C. 154(b) by 201 days.

(21) Appl. No.: 12/086,479

(22) PCT Filed: Dec. 6, 2006

(86) PCT No.: PCT/JP2006/324881
§ 371 (c)(1),
(2), (4) Date: Oct. 24, 2008

(87) PCT Pub. No.: WO2007/069666
PCT Pub. Date: Jun. 21, 2007

(65) Prior Publication Data
US 2009/0068742 A1   Mar. 12, 2009

(30) Foreign Application Priority Data
Dec. 13, 2005   (JP) ................................ 2005-359537

(51) Int. Cl.
*C07H 21/04*   (2006.01)
(52) U.S. Cl. .................... 536/23.5; 435/377; 530/350
(58) Field of Classification Search .................. None
See application file for complete search history.

(56) References Cited

U.S. PATENT DOCUMENTS

| | | | |
|---|---|---|---|
| 4,650,764 A | 3/1987 | Temin et al. | |
| 4,861,719 A | 8/1989 | Miller | |
| 4,937,190 A | 6/1990 | Palmenberg et al. | |
| 5,225,348 A | 7/1993 | Nagata et al. | |
| 5,266,491 A | 11/1993 | Nagata et al. | |
| 5,268,290 A | 12/1993 | Hasegawa et al. | |
| 5,288,514 A | 2/1994 | Ellman | |
| 5,324,645 A | 6/1994 | Takahara et al. | |
| 5,449,614 A | 9/1995 | Danos et al. | |
| 5,519,134 A | 5/1996 | Acevedo et al. | |
| 5,525,735 A | 6/1996 | Gallop et al. | |
| 5,549,974 A | 8/1996 | Holmes | |
| 5,591,624 A | 1/1997 | Barber et al. | |
| 5,637,456 A | 6/1997 | Roth et al. | |
| 5,652,122 A | 7/1997 | Frankel et al. | |
| 5,674,980 A | 10/1997 | Frankel | |
| 5,707,618 A | 1/1998 | Armentano et al. | |
| 5,716,832 A | 2/1998 | Barber et al. | |
| 5,744,320 A | 4/1998 | Sherf et al. | |
| 5,817,491 A | 10/1998 | Yee et al. | |
| 5,830,725 A | 11/1998 | Nolan et al. | |
| 5,834,256 A | 11/1998 | Finer et al. | |
| 5,858,740 A | 1/1999 | Finer et al. | |
| 5,910,434 A | 6/1999 | Rigg et al. | |
| 5,955,331 A | 9/1999 | Danos et al. | |
| 6,013,517 A | 1/2000 | Respess et al. | |
| 6,017,735 A | 1/2000 | O'hare et al. | |
| 6,017,761 A | 1/2000 | Rigg et al. | |
| 6,025,192 A | 2/2000 | Beach et al. | |
| 6,140,111 A | 10/2000 | Riviere et al. | |
| 6,146,874 A | 11/2000 | Zolotukhin et al. | |
| 6,153,432 A | 11/2000 | Halvorsen et al. | |
| 6,153,745 A | 11/2000 | Williams et al. | |
| 6,203,975 B1 | 3/2001 | Wilson et al. | |
| 6,251,398 B1 | 6/2001 | O'Hare et al. | |
| 6,255,071 B1 | 7/2001 | Beach et al. | |
| 6,312,948 B1 | 11/2001 | Cohen-haguenauer | |
| 6,312,949 B1 | 11/2001 | Sakurada et al. | |
| 6,333,195 B1 | 12/2001 | Respess et al. | |
| 6,365,352 B1 | 4/2002 | Yerramilli et al. | |
| 6,395,546 B1 | 5/2002 | Zobel et al. | |
| 6,451,595 B1 | 9/2002 | Kim et al. | |
| 6,485,959 B1 | 11/2002 | Demetriou et al. | |
| 6,521,453 B1 | 2/2003 | Crameri et al. | |
| 6,521,455 B2 | 2/2003 | O'Hare et al. | |
| 6,605,275 B1 | 8/2003 | Boyse et al. | |
| 6,660,514 B1 | 12/2003 | Zolotukhin et al. | |
| 6,773,920 B1 | 8/2004 | Dalby et al. | |
| 6,833,269 B2 | 12/2004 | Carpenter | |
| 6,841,535 B2 | 1/2005 | Divita et al. | |
| 6,872,528 B2 | 3/2005 | Klatzmann et al. | |
| 6,875,578 B2 | 4/2005 | Giuliano et al. | |
| 6,881,825 B1 | 4/2005 | Robbins et al. | |
| 6,910,434 B2 | 6/2005 | Lundgren et al. | |

(Continued)

FOREIGN PATENT DOCUMENTS

AU   2008201280 A1   4/2008

(Continued)

OTHER PUBLICATIONS

Bibel et al. Differentiation of mouse embryonic stem cells into a defined neuronal lineage.Nature Neuroscience, 2004, vol. 7, pp. 1003-1009.*
Cohen et al. Ooplasmic Transfer in Mature Human Ooctyes, Molecular Human Reproduction, 1998, vol. 4, pp. 269-280.*
Do et al. Nuclei of Embryonic Stem Cells Reprogram Somatic Cells, Stem Cells, 2004, vol. 22, pp. 941-949.*
Evans et al., "Establishment in culture of pluripotential cells from mouse embryos" *Nature* 292:154-56, 1981.
Martin, "Isolation of a pluripotent cell line from early mouse embryos cultured in medium conditioned by teratocarcinoma stem cells" *Proc. Natl . Acad. Sci. U.S.A.* 78(12):7634-38, 1981.
Thomson et al., "Embryonic Stem Cell Lines Derived from Human Blastocysts" *Science* 282:1145-47, 1998.

(Continued)

*Primary Examiner* — Deborah Crouch
(74) *Attorney, Agent, or Firm* — Knobbe Martens Olson & Bear LLP

(57) ABSTRACT

There is provided a nuclear reprogramming factor for a somatic cell, which comprises a gene product of each of the following three kinds of genes: an Oct family gene, a Klf family gene, and a Myc family gene, as a means for inducing reprogramming of a differentiated cell to conveniently and highly reproducibly establish an induced pluripotent stem cell having pluripotency and growth ability similar to those of ES cells without using embryo or ES cell.

25 Claims, 24 Drawing Sheets

U.S. PATENT DOCUMENTS

| | | | |
|---|---|---|---|
| 6,995,009 B1 | 2/2006 | Kitamura et al. |
| 7,029,913 B2 | 4/2006 | Thomson |
| 7,030,292 B2 | 4/2006 | Yan et al. |
| 7,070,994 B2 | 7/2006 | Barber et al. |
| 7,250,255 B2 | 7/2007 | Yamanaka |
| 7,439,064 B2 | 10/2008 | Thomson et al. |
| 2002/0090722 A1 | 7/2002 | Dominko et al. |
| 2002/0123146 A1 | 9/2002 | Klatzmann et al. |
| 2002/0174013 A1 | 11/2002 | Freeman et al. |
| 2003/0003574 A1 | 1/2003 | Toma et al. |
| 2003/0044976 A1 | 3/2003 | Dominko et al. |
| 2003/0161817 A1 | 8/2003 | Young et al. |
| 2004/0048297 A1 | 3/2004 | Scherf |
| 2004/0137460 A1 | 7/2004 | Yamanaka et al. |
| 2005/0019801 A1 | 1/2005 | Rubin et al. |
| 2005/0026133 A1 | 2/2005 | Nakatsuji et al. |
| 2005/0079606 A1 | 4/2005 | Tamaki et al. |
| 2005/0130144 A1 | 6/2005 | Nakatsuji et al. |
| 2006/0030041 A1 | 2/2006 | Furcht et al. |
| 2006/0084172 A1 | 4/2006 | Muller et al. |
| 2006/0088599 A1 | 4/2006 | Prasad et al. |
| 2006/0095319 A1 | 5/2006 | Cardwell |
| 2006/0110830 A1 | 5/2006 | Dominko et al. |
| 2006/0292620 A1 | 12/2006 | Yamanaka et al. |
| 2007/0033061 A1 | 2/2007 | Patten et al. |
| 2007/0053884 A1 | 3/2007 | Suda et al. |
| 2007/0155013 A1 | 7/2007 | Akaike et al. |
| 2007/0202592 A1 | 8/2007 | Kitagawa et al. |
| 2007/0254884 A1 | 11/2007 | Chen et al. |
| 2007/0269790 A1 | 11/2007 | Amit et al. |
| 2008/0003560 A1 | 1/2008 | Nakatsuji et al. |
| 2008/0076176 A1 | 3/2008 | Dominko et al. |
| 2008/0085555 A1 | 4/2008 | Asahara et al. |
| 2008/0132803 A1 | 6/2008 | Friedlander |
| 2008/0171358 A1 | 7/2008 | Perrault |
| 2008/0171385 A1 | 7/2008 | Bergendahl et al. |
| 2008/0206865 A1 | 8/2008 | Zhang et al. |
| 2008/0233610 A1 | 9/2008 | Thomson et al. |
| 2008/0274914 A1 | 11/2008 | Yamanaka et al. |
| 2008/0280362 A1 | 11/2008 | Jaenisch et al. |
| 2008/0293143 A1 | 11/2008 | Lin et al. |
| 2008/0299548 A1 | 12/2008 | Yamanaka |
| 2009/0047263 A1 | 2/2009 | Yamanaka et al. |
| 2009/0191159 A1 | 7/2009 | Sakurada et al. |
| 2009/0191171 A1 | 7/2009 | Ma |
| 2009/0227032 A1 | 9/2009 | Yamanaka |
| 2009/0246875 A1 | 10/2009 | Yamanaka et al. |
| 2009/0299763 A1 | 12/2009 | Sakurada |
| 2009/0304646 A1 | 12/2009 | Sakurada et al. |
| 2009/0324559 A1 | 12/2009 | Sakurada |
| 2010/0003757 A1 | 1/2010 | Mack |
| 2010/0021437 A1 | 1/2010 | Isacson |
| 2010/0062533 A1 | 3/2010 | Yamanaka |
| 2010/0062534 A1 | 3/2010 | Hochedlinger |
| 2010/0075421 A1 | 3/2010 | Yamanaka |
| 2010/0093090 A1 | 4/2010 | Deng |
| 2010/0105100 A1 | 4/2010 | Sakurada |
| 2010/0120069 A1 | 5/2010 | Sakurada |
| 2010/0144031 A1 | 6/2010 | Jaenisch |
| 2010/0184051 A1 | 7/2010 | Hochedlinger |
| 2010/0184227 A1 | 7/2010 | Thomson |
| 2010/0210014 A1 | 8/2010 | Yamanaka |
| 2010/0216236 A1 | 8/2010 | Yamanaka |
| 2010/0221827 A1 | 9/2010 | Jaenisch |
| 2010/0233804 A1 | 9/2010 | Zhou |
| 2010/0240090 A1 | 9/2010 | Sakurada |
| 2010/0267135 A1 | 10/2010 | Sakurada |
| 2010/0279404 A1 | 11/2010 | Yamanaka |
| 2011/0039332 A1 | 2/2011 | Sakurada et al. |

FOREIGN PATENT DOCUMENTS

| | | |
|---|---|---|
| CN | 101250502 A | 8/2008 |
| CN | 101250502 A | 10/2009 |
| CN | 101550428 A | 10/2009 |
| EP | 1384775 A1 | 1/2004 |
| EP | 1403366 A1 | 3/2004 |
| EP | 1970446 A1 | 9/2008 |
| EP | 2096169 A1 | 9/2009 |
| JP | 2-227075 | 9/1990 |
| JP | 2002-065261 | 3/2002 |
| JP | 2003-009854 | 1/2003 |
| JP | 2004-161682 A | 6/2004 |
| JP | 2005-095027 | 4/2005 |
| JP | 2008-283972 | 11/2008 |
| WO | WO 95/10619 A2 | 4/1995 |
| WO | WO 95/10619 A3 | 7/1995 |
| WO | WO 97/05265 A1 | 2/1997 |
| WO | WO 98/02529 | 1/1998 |
| WO | WO 99/64568 | 12/1999 |
| WO | 00/18885 | 4/2000 |
| WO | WO 00/23567 A2 | 4/2000 |
| WO | 00/27995 A1 | 5/2000 |
| WO | WO 00/23567 A3 | 7/2000 |
| WO | WO 00/73423 A1 | 12/2000 |
| WO | WO 01/21767 A2 | 3/2001 |
| WO | 01/34776 A1 | 5/2001 |
| WO | 01/51616 A2 | 7/2001 |
| WO | WO 01/21767 A3 | 8/2001 |
| WO | 01/81549 A2 | 11/2001 |
| WO | WO 02/00871 A2 | 1/2002 |
| WO | 02/061033 A2 | 8/2002 |
| WO | WO 02/00871 A3 | 10/2002 |
| WO | WO 02/086129 A1 | 10/2002 |
| WO | WO 02/086134 A2 | 10/2002 |
| WO | 02/097090 A1 | 12/2002 |
| WO | 03/018780 A1 | 3/2003 |
| WO | WO 02/086134 A3 | 12/2003 |
| WO | 2004/081205 A1 | 9/2004 |
| WO | 2005/035741 A1 | 4/2005 |
| WO | 2005/080598 A1 | 9/2005 |
| WO | 2005/090557 A1 | 9/2005 |
| WO | 2006/035741 A1 | 4/2006 |
| WO | WO 2006/084229 A2 | 8/2006 |
| WO | WO 2006/088867 A2 | 8/2006 |
| WO | 2007/026255 A2 | 3/2007 |
| WO | WO 2007/054720 A1 | 5/2007 |
| WO | 2007/069666 A1 | 6/2007 |
| WO | 2007/097494 A1 | 8/2007 |
| WO | 2008/030610 A2 | 3/2008 |
| WO | WO 2008/035110 A1 | 3/2008 |
| WO | 2008/038148 A2 | 4/2008 |
| WO | WO 2008/089351 A1 | 7/2008 |
| WO | 2008/105630 A1 | 9/2008 |
| WO | WO 2008/105566 A1 | 9/2008 |
| WO | WO 2008/116213 A1 | 9/2008 |
| WO | 2008/118820 A2 | 10/2008 |
| WO | 2008/124133 A1 | 10/2008 |
| WO | WO 2008/118820 A3 | 11/2008 |
| WO | 2008/151058 A2 | 12/2008 |
| WO | WO 2008/150814 A2 | 12/2008 |
| WO | 2009/006930 A1 | 1/2009 |
| WO | 2009/006997 A1 | 1/2009 |
| WO | 2009/007852 A2 | 1/2009 |
| WO | WO 2008/151058 A3 | 1/2009 |
| WO | WO 2008/150814 A3 | 2/2009 |
| WO | WO 2009/023161 A1 | 2/2009 |
| WO | 2009/032456 A2 | 3/2009 |
| WO | WO 2009/032194 A1 | 3/2009 |
| WO | WO 2009/032456 A3 | 4/2009 |
| WO | 2009/057831 A1 | 5/2009 |
| WO | WO 2009/057831 A1 | 5/2009 |
| WO | WO 2009/061442 A1 | 5/2009 |
| WO | WO 2009/067563 A1 | 5/2009 |
| WO | WO 2009/007852 A3 | 8/2009 |
| WO | WO 2009/096614 A1 | 8/2009 |
| WO | WO 2009/102983 A2 | 8/2009 |
| WO | WO 2009/115295 A1 | 9/2009 |
| WO | WO 2009/133971 A1 | 11/2009 |
| WO | WO 2009/102983 A3 | 12/2009 |
| WO | WO 2009/144008 A1 | 12/2009 |
| WO | WO 2609/149233 A1 | 12/2009 |
| WO | WO 2010/013359 A1 | 2/2010 |
| WO | WO 2010/048567 A1 | 4/2010 |

OTHER PUBLICATIONS

Wakayama et al., "Full-term development of mice from enucleated oocytes injected with cumulus cell nuclei" *Nature* 394:369-74, 1998.

Wilmut et al., "Viable offspring derived from fetal and adult mammalian cells" *Nature* 385:810-13, 1997.

Hwang et al., "Evidence of a Pluriportent Human Embryonic Stem Cell Line Derived from a Cloned Blastocyst" *Science* 303:1669-74, 2004.

Hwang et al., "Patient-Specific Embryonic Stem Cells Derived from Human SCNT Blastocysts" *Science* 308:1777-83, 2005.

Tada et al., "Nuclear reprogramming of somatic cells by in vitro hybridization with ES cells" *Current Biology* 11(19):1553-58, 2001.

Cowan et al., "Nuclear Reprogramming of Somatic Cells After Fusion with Human Embryonic Stem Cells" *Science* 309:1369-73, 2005.

Taranger et al., "Induction of Dedifferentiation, Genomewide Transcriptional Programming, and Epigenetic Reprogramming by Extracts of Carcinoma and Embryonic Stem Cells" *Mol. Biol. Cell* 16:5719-35, 2005.

Tokuzawa et al., "Fbx15 Is a Novel Target of Oct3/4 but is Dispensable for Embryonic Stem Cell Self-Renewal and Mouse Development" *Mol. Cell Biol.* 23(8): 2699-708, 2003.

Okamoto et al., "A Novel Octamer Binding Transportation Factor is Differentially Expressed in Mouse Embryonic Cells" *Cell* 60:461-72, 1990.

Nichols et al., "Formation of Pluripotent Stem Cells in the Mammalian Embryo Depends on the POU Transcription Factor Oct4" *Cell* 95:379-91, 1998.

Ghaleb et al., "Krüppel-like factors 4 and 5: the yin and yang regulators of cellular proliferation" *Cell Res.* 15(2):92-96, 2005.

Adhikary et al., "Transcriptional regulation and transformation by Myc proteins" *Nat. Rev. Mol. Cell Biol.* 6:635-45, 2005.

Cartwright et al., "LIF/STAT3 controls ES cell self-renewal and pluripotency by a Myc-dependent mechanism" *Development* 132:885-96, 2005.

Avilion et al., "Multipotent cell lineages in early mouse development depend on SOX2 function" *Genes Dev.* 17:126-40, 2003.

Horikawa et al., "Differential cis-regulation of human versus mouse *TERT* gene expression in vivo: Identification of a human-specific repressive element" *Proc. Natl. Acad. Sci. U.S.A.* 102(51):18437-42, 2005.

Akimov et al., "Bypass of Senescence, Immortalization, and Transformation of Human Hematopoietic Progenitor Cells" *Stem Cells* 23:1423-33, 2005.

Salmon et al., "Reversible Immortalization of Human Primary Cells by Lentivector-Mediated Transfer of Specific Genes" *Mol. Ther.* 2(4):404-14, 2000.

Mitsui et al., "The Homeoprotein Nanog Is Required for Maintenance of Pluripotency in Mouse Epiblast and ES cells" *Cell* 113:631-42, 2003.

Takahashi et al., "Role of ERas in promoting tumour-like properties in mouse embryonic stem cells" *Nature* 423:541-45, 2003.

Bortvin et al., "Incomplete reactivation of *Oct4*-related genes in mouse embryos cloned from somatic nuclei" *Development* 130:1673-80, 2003.

Sato et al., "Maintenance of pluripotency in human and mouse embryonic stem cells through activation of Wnt signaling by a pharmacological GSK-3-specific inhibitor" *Nat. Med.* 10(1):55-63, 2004.

Maruyama et al., "Differential Roles for Sox15 and Sox2 in Transcriptional Control in Mouse Embryonic Stem Cells" *J. Biol. Chem.* 280(26):24371-79, 2005.

Loriot et al., "Five new human cancer-germline genes identified among 12 genes expressed in spermatogonia." *Int. J. Cancer* 105:371-76, 2003.

Kohlhase et al., "Cloning and expression analysis of *Sall4*, the murine homologue of the gene mutated in Okihiro syndrome" *Cytogenet. Genome Res.* 98:274-77, 2002.

Ben-Shushan et al., "*Rex-1*, a Gene Encoding a Transcription Factor Expressed in the Early Embryo, Is Regulated via Oct-3/4 and Oct-6 Binding to an Octomer Site and a Novel Protein, Rox-1, Binding to an Adjacent Site" *Mol. Cell Biol.* 18(4):1866-78, 1998.

Okuda et al., "UTF1, a novel transcriptional coactivator expressed in pluripotent embryonic stem cells and extra-embryonic cells" *EMBO J.* 17(7):2019-32, 1998.

Niwa et al., "Self-renewal of pluripotent embryonic stem cells is meditated via activation of STAT3" *Genes Dev.* 12:2048-60, 1998.

Cheng et al., "Mammalian Grb2 Regulates Multiple Steps in Embryonic Development and Malignant Transformation" *Cell* 95:793-803, 1998.

Maherali et al., "Directly Reprogrammed Fibroblasts Show Global Epigenetic Remodeling and Widespread Tissue Contribution" *Cell Stem Cell* 1:55-70, 2007.

Okita et al., "Generation of germline-competent induced pluripotent stem cells" *Nature* 448:313-17, 2007.

Wernig et al., "In vitro reprogramming of fibroblasts into a pluripotent ES-cell-like state" *Nature* 448:318-24, 2007.

Takahashi et al., "Induction of Pluripotent Stem Cells from Mouse Embryonic and Adult Fibroblast Cultures by Defined Factors" *Cell* 126(4):663-76, published online Aug. 10, 2006.

Morita et al., "Plat-E: an efficient and stable system for transient packaging of retroviruses" *Gene Ther.* 7:1063-66, 2000.

Verrey et al., "CATs and HATs: the SLC7 family of amino acid transporters" *Pflügers Archiv-European Journal of Physiology*, DOI 10.1007/s00424-003-1086-z, pp. 1-23, published online Jun. 11, 2003.

McMahon et al., "The *Wnt-1* (*int-1*) Proto-Oncogene Is Required for Development of a Large Region of the Mouse Brain" *Cell* 62:1073-85, 1990.

Adewumi et al., "Characterization of human embryonic stem cell lines by the International Stem Cell Initiative" *Nat. Biotechnol.* 25(7):803-16, 2007.

Cowan et al., "Derivation of Embryonic Stem-Cell Lines from Human Blastocysts" *N. Engl. J. Med.* 350:1353-56, 2004.

Itskovitz-Eldor et al., "Differentiation of Human Embryonic Stem Cells into Embryoid Bodies Comprising the Three Embryonic Germ Layers" *Mol. Med.* 6(2):88-95, 2000.

Kawasaki et al., "Induction of Midbrain Dopaminergic Neurons from ES Cells by Stromal Cell-Derived Inducing Activity" *Neuron* 28:31-40, 2000.

Laflamme et al., "Cardiomyocytes derived from human embryonic stem cells in pro-survival factors enhance function of infracted rat hearts" *Nat. Biotechnol.* 25(9):1015-24, 2007.

Rao, "Conserved and divergent paths that regulate self-renewal in mouse and human embryonic stem cells" *Dev. Biol.* 275:269-86, 2004.

Amit et al., "Clonally Derived Human Embryonic Stem Cell Lines Maintain Pluripotency and Proliferative Potential for Prolonged Periods of Culture" *Dev. Biol.* 227:271-78, 2000.

Matsuda et al., "STAT3 activation is sufficient to maintain an undifferentiated state of mouse embryonic stem cells" *EMBO J.* 18(15):4261-69, 1999.

Xu et al., "Basic FGF and suppression of BMP signaling sustain undifferentiated proliferation of human ES cells" *Nat. Methods* 2(3):185-90, 2005.

Ying et al., "BMP Induction of Id Proteins Suppresses Differentiation and Sustains Embryonic Stem Cell Self-Renewal in Collaboration with STAT3" *Cell* 115:281-92, 2003.

Boyer et al., "Core Transcriptional Regulatory Circuitry in Human Embryonic Stem Cells" *Cell* 122:947-56, 2005.

Loh et al., "The Oct4 and Nanog transcription network regulates pluripotency in mouse embryonic stem cells" *Nat. Genet.* 38(4):431-40, 2006.

Wang et al., "A protein interaction network for pluripotency of embryonic stem cells" *Nature* 444:364-68, 2006.

Yamanaka, "Strategies and New Developments in the Generation of Patient-Specific Pluripotent Stem Cells" *Cell Stem Cell* 1:39-49, 2007.

Evans et al., "Krüppel-like Factor 4 Is Acetylated by p300 and Regulates Gene Transcription via Modulation of Histone Acetylation" *J. Biol. Chem.* 282(47):33994-34002, 2007.

Sumi et al., "Apoptosis and differentiation of human embryonic stem cells induced by sustained activation of c-Myc" *Oncogene* 26:5564-76, 2007.

Chambers et al., "Functional Expression Cloning of Nanog, a Pluripotency Sustaining Factor in Embryonic Stem Cells" *Cell* 113:643-55, 2003.

Ryan et al., "POU domain family values: flexibility, partnerships, and developmental codes" *Genes Dev.* 11:1207-25, 1997.

Schepers et al., "Twenty Pairs of *Sox*: Extent, Homology, and Nomenclature of the Mouse and Human *Sox* Transcription Factor Gene Families" *Dev. Cell* 3:167-70, 2002.

Dang et al., "The biology of the mammalian Krüppel-like family of transcription factors" *Int. J. Biochem. Cell Biol.* 32:1103-21, 2000.

Vintersten et al., "Mouse in Red: Red Fluorescent Protein Expression in Mouse ES Cells, Embryos, and Adult Animals" *Genesis* 40:241-46, 2004.

Meiner et al., "Disruption of the acyl-CoA:cholesterol acyltransferase gene in mice: Evidence suggesting multiple cholesterol esterification enzymes in mammals" *Proc. Natl. Acad. Sci. U.S.A.* 93:14041-46, 1996.

Yu et al., "Induced Pluripotent Stem Cell Lines Derived from Human Somatic Cells" *Science* 318(5858):1917-20, published online Nov. 20, 2007.

Takahashi et al., "Induction of Pluripotent Stem Cells from Adult Human Fibroblasts by Defined Factors" *Cell* 131(5):861-72, published online Nov. 20, 2007.

Nakagawa et al., "Generation of induced pluripotent stem cells without Myc from mouse and human fibroblasts" *Nat. Biotechnol.* 26(1):101-06, published online Nov. 30, 2007.

Takahashi et al., "Induction of pluripotent stem cells from fibroblast cultures" *Nat. Protocols* 2(12):3081-89, published online Nov. 29, 2007.

Yamanaka et al., "Mouse Sen'iga Saibo Kara Yudo Tanosei Kansaibo o Tsukuru (Induction of pluripotent stem cells from mouse fibroblast cultures)" *Tanpakushitsu Kakusan Koso* (*Protein, Nucleic Acid and Enzyme*) 51(15):2346-51, 2006.

Aoi et al., "Generation of pluripotent stem cells from adult mouse liver and stomach cells" *Science* 321(5889):699-702, published online Feb. 14, 2008.

Bambrink et al., "Sequential expression of pluripotency markers during direct reprogramming of mouse somatic cells" *Cell Stem Cell* 2(2):151-59, 2008.

Barrett et al. "Activation Domains of L-Myc and c-Myc Determine Their Transforming Potencies in Rat Embryo Cells" *Mol. Cell. Biol.* 12(7):3130-37, 1992.

Benetti et al., "A mammalian microRNA cluster controls DNA methylation and telomere recombination via Rbl2-dependent regulation of DNA methyltransferases" *Nat. Struct. Mol. Biol.* 15(3):268-79, published online Mar. 2, 2008.

Birrer et al., "L-*myc* Cooperates with *ras* to Transform Primary Rat Embryo Fibroblasts" *Mol. Cell. Biol.* 8(6):2668-73, 1988.

Blackwood et al., "Max: a helix-loop-helix zipper protein that forms a sequence-specific DNA-binding complex with Myc" *Science* 251(4998):1211-17, 1991.

Blelloch et al., "Generation of Induced Pluripotent Stem Cells in the Absence of Drug Selection" *Cell Stem Cell* 1(3):245-247, 2007.

Block et al., "Population Expansion, Clonal Growth, and Specific Differentiation Patterns in Primary Cultures of Hepatocytes Induced by HGF/SF, EGF and TGFα in a Chemically Defined (HGM) Medium" *J. Cell Biol.* 132(6):1133-49, 1996.

Brough et al., "An Essential Domain of the c-Myc Protein Interacts with a Nuclear Factor That Is Also Required for E1A-Mediated Transformation" *Mol. Cell. Biol.* 15(3):1536-44, 1995.

Griffiths-Jones et al., "miRBase: tools for microRNA genomics" *Nucleic Acids Research* 36:D154-D158, published online Nov. 8, 2007.

Hanna et al., "Treatment of sickle cell anemia mouse model with iPS cells generated from autologous skin" *Science* 318(5858):1920-23, published online Dec. 6, 2007.

Hasegawa et al., "Efficient Multicistronic Expression of a Transgene in Human Embryonic Stem Cells" *Stem Cells* 25:1707-12, 2007.

Herold et al. "Negative Regulation of the Mammalian UV Response by Myc through Association with Miz-1" *Mol. Cell* 10(3):509-21, 2002.

Houbaviy et al., "Embryonic Stem Cell-Specific MicroRNAs" *Developmental Cell* 5(2):351-58, 2003.

Hsiao et al., "Marking Embryonic Stem Cells with a 2A Self-Cleaving Peptide: A NKX2-5 Emerald GFP BAC Reporter" *PLoS ONE* 3(7):e2532, 2008.

Humphries, C. "Reprogrammed Stem Cells Work on Parkinson's: A study in rodents suggests that skin cells can be transformed into neurons to treat neurodegeneration" *Technology Review*, published by MIT, Apr. 8, 2008; http:///www.technologyreview.com/printer_friendly_article.aspx?id=20530.

*Jikken Igaku* (*Experimental Medicine*) 24:814-19, 2006, along with an English language translation thereof.

Li et al., "Leukaemia disease genes: large-scale cloning and pathway predictions" *Nat. Genet.* 23(3):348-353, 1999.

Lowry et al., "Generation of human induced pluripotent stem cells from dermal fibroblasts" *Proc. Natl. Acad. Sci. U.S.A.* 105(8):2883-88, 2008.

Mali et al., "Improved Efficiency and Pace of Generating Induced Pluripotent Stem Cells from Human Adult and Fetal Fibroblasts" *Stem Cells*, published online May 29, 2008, DOI:10.1634/stemcells.2008-0346.

Masaki et al., "Heterogeneity of pluripotent marker gene expression in colonies generated in human iPS cell induction culture" *Stem Cell Res.* (2008) DOI:10.1016/j.scr.2008.01.001.

*MicroRNA Jikken Purotokoru* (*miroRNA Experimental Protocol*), pp. 20-35, 2008, Yodosha Co., LTD.

Ying et al., "The MicroRNA: Overview of the RNA Gene That Modulates Gene Functions," *Methods in Molecular Biology, MicroRNA Protocols*, vol. 342, pp. 1-18, Humana Press, 2006.

Meissner et al., "Direct reprogramming of genetically unmodified fibroblasts into pluripotent stem cells" *Nat. Biotechnol.* 25(10):1177-1181, published online Aug. 27, 2007.

Nienhuis et al., "Genotoxicity of retroviral integration in hematopoietic cells" *Mol. Ther.* 13(6):1031-49, 2006.

Niwa et al., "Efficient selection for high-expression transfectants with a novel eukaryotic vector" *Gene* 108(2):193-99, 1991.

Nolta et al., "Transduction of pluripotent human hematopoietic stem cells demonstrated by clonal analysis after engraftment in immune-deficient mice" *Proc. Natl. Acad. Sci. USA* 93:2414-19, 1996.

Okita et al., "Generation of mouse induced pluripotent stem cells without viral vectors" *Science* 322(5903):949-53, published online Oct. 9, 2008.

Park et al., "Reprogramming of human somatic cells to pluripotency with defined factors" *Nature* 451:141-46, published online Dec. 23, 2007.

Sakai et al., "A Transgenic Mouse Line That Retains Cre Recombinase Activity in Mature Oocytes Irrespective of the *cre* Transgene Transmission" *Biochem. Biophys. Res. Commun.* 237(2):318-24, 1997.

Sinkkonen et al., "MicroRNAs control *de novo* DNA methylation through regulation of transcriptional repressors in mouse embryonic stem cells" *Nat. Struct. Mol. Biol.* 15(3):259-267, published online Mar. 2, 2008.

Spencer et al., "E-Cadherin Inhibits Cell Surface Localization of the Pro-Migratory 5T4 Oncofetal Antigen in Mouse Embryonic Stem Cells" *Mol. Biol. Cell* 18:2838-51, 2007.

Stadtfeld et al., "Induced pluripotent stem cells generated without viral integration" *Science* 322(5903):945-49, published online Sep. 25, 2008.

Stadtfeld et al., "Defining Molecular Cornerstones during Fibroblast to iPS Cell Reprogramming in Mouse" *Cell Stem Cell* 2(3):230-40, 2008.

Takahashi et al. "Induced Pluripotent Stem Cells" *Jikken Igaku* (*Experimental Medicine*) 26(5):35-40, 2008.

Takeda et al. "Human Oct3 gene family: cDNA sequences, alternative splicing, gene organization, chromosomal location, and expression at low levels in adult tissues" *Nucleic Acids Research* 20(17):4613-4620, 1992.

Tateno et al., "Heterogeneity of growth potential of adult rat hepatocytes in vitro" *Hepatology* 31(1):65-74, 2000.

Qin et al., "Direct generation of ES-like cells from unmodified mouse embryonic fibroblasts by Oct4/Sox2/Myc/Klf4" *Cell Res.* 17(11):959-62, 2007.

Wernig et al., "c-Myc is dispensable for direct reprogramming of mouse fibroblasts" *Cell Stem Cell* 2(1):10-12, published online Dec. 13, 2007.

Wernig et al., "Neurons derived from reprogrammed fibroblasts functionally integrate into the fetal brain and improve symptoms of rats with Parkinson's disease" *Proc. Natl. Acad. Sci. U.S.A.* 105(15):5856-5861, 2008.

Yang et al., "Nuclear reprogramming of cloned embryos and its implications for therapeutic cloning" *Nat. Genet.* 39(3):295-302, 2007.

"Stem cells made to mimic disease" BBC News, http://newsvote.bbc.co.uk/mpapps/pagetools/print/news.bbc.co.uk/2/hi/health/7334365.stm, Apr. 7, 2008.

English language Abstract of JP 2002-065261.

English language Abstract of JP 2003-009854.

English language Abstract of JP 2005-095027.

English language Abstract of JP 2005-359537.

English language Abstract of JP 2004-161682 A.

Postic et al., "Dual Roles for Glucokinase in Glucose Homeostasis as Determined by Liver and Pancreatic β Cell-specific Gene Knockouts Using Cre Recombinase" *J. Biol. Chem.* 274(1):305-15, 1999.

Yamanaka, "Pluripotency of differentiation and miRNA" *The Journal of Biochemistry*, vol. 79, No. 11, Abstract 3BT17 from the 80$^{th}$ Annual Meeting of the Japanese Biochemical Society, Nov. 25, 2007, along with an English language translation thereof.

Koyanagi et al., "Screening and functional analysis of microRNAs which involve in reprogramming of murine somatic cells" *The Journal of Biochemistry*, vol. 79, No. 11, Abstract 1T7-7 from the 80$^{th}$ Annual Meeting of the Japanese Biochemical Society, Nov. 25, 2007, along with an English language translation thereof.

Zhang et al., "MicroRNA: A New Player in Stem Cells" *Journal of Cellular Physiology* 209:266-269, 2006.

Spivakov et al. "Epigenetic signatures of stem-cell identity" *Nat. Rev. Genet.* 8(4):263-271, 2007.

Suh et al. "Human embryonic stem cells express a unique set of microRNAs" *Developmental Biology* 270:488-498, 2004.

Hatfield et al., "Stem cell division is regulated by the microRNA pathway" *Nature* 435(7044):974-978, 2005.

Kanellopoulou et al. "Dicer-deficient mouse embryonic stem cells are defective in differentiation and centromeric silencing" *Genes & Development* 19:489-501, 2005.

Bang et al. "Deconstructing Pluripotency" *Science* 320:58-59, 2008.

Viswanathan et al. "Selective Blockade of MicroRNA Processing by Lin28" *Science* 320:97-100, 2008.

U.S. Appl. No. 12/213,035, filed Jun. 13, 2008 to Yamanaka et al., entitled "Nuclear Reprogramming Factor and Induced Pluripotent Stem Cells."

U.S. Appl. No. 12/289,873, filed Nov. 6, 2008 to Yamanaka et al., entitled "Nuclear Reprogramming Factor and Induced Pluripotent Stem Cells."

U.S. Appl. No. 12/292,717, filed Nov. 25, 2008 to Yamanaka et al., entitled "Efficient Method for Nuclear Reprogramming."

U.S. Appl. No. 12/379,564, filed Feb. 25, 2009 to Yamanaka et al., entitled "Efficient Method for Nuclear Reprogramming."

Huangfu et al., "Induction of Pluripotent Stem Cells by Defined Factors is Greatly Improved by Small-Molecule Compounds" *Nature Biotechnology* 26(7):795-97, 2008.

Kubicek et al., "Reversal of H3K9me2 by a Small-Molecule Inhibitor for the G9a Histone Methyltransferase" *Molecular Cell* 25:473-81, 2007.

Lin et al., "Mir-302 Reprograms Human Skin Cancer Cells into a Pluripotent ES-Cell-Like State" *RNA* 14:1-10, 2008.

Marson et al., "Wnt Signaling Promotes Reprogramming of Somatic Cells to Pluripotency" *Cell Stem Cell* 3:132-35, 2008.

Nolta et al., "Transduction of Pluripotent Human Hematopoietic Stem Cells Demonstrated by Clonal Analysis After Engraftment in Immune-Deficient Mice" *Proc. Natl. Acad. Sci. USA* 93(6):2414-19, 1996.

Shi et al., "A Combined Chemical and Genetic Approach for the Generation of Induced Pluripotent Stem Cells" *Cell Stem Cell* 2:525-28, 2008.

Shi et al., "Induction of Pluripotent Stem Cells from Mouse Embryonic Fibroblasts by Oct4 and Klf4 with Small-Molecule Compounds" *Cell Stem Cell* 3:568-74, 2008.

Silva et al., "Promotion of Reprogramming to Ground State Pluripotency by Signal Inhibition" *PLoS Biology* 6(10):2237-47, 2008.

Zhao et al., "Two Supporting Factors Greatly Improve the Efficiency of Human iPSC Generation" *Cell Stem Cell* 3:475-79, 2008.

Check, E. "Simple Recipe Gives Adult Cells Embryonic Powers" *Nature* 442:11, Jul. 6, 2006.

Cyranoski et al., "Simple Switch Turns Cells Embryonic" *Nature* 447:618-619, Jun. 7, 2007.

Correction printed in *Nature* 447:897, Jun. 21, 2007.

Hanna et al., "Direct Reprogramming of Terminally Differentiated Mature B Lymphocytes to Pluripotency" *Cell* 133:250-264, Apr. 17, 2008.

Liao et al., "Enhanced Efficiency of Generating Induced Pluripotent Stem (iPS) Cells from Human Somatic Cells by a Combination of Six Transcription Factors" *Cell Research* 18:600-603, doi: 10.1038/cr.2008.51, published online Apr. 15, 2008.

Surani et al., "A New Route to Rejuvenation" *Nature* 443:284-285, Sep. 21, 2006.

*Kyoto Shimbun* (Japanese Newspaper) article of Apr. 16, 2008, cols. 1-3, along with a partial English language translation thereof.

*Newton* "Attracting world's attention. Pluripotent cells are generated from human skin. What is the 'iPS cell' that can be used not only in the regeneration therapy but also in the tailor-made therapy" pp. 70-75, Feb. 2008, along with a partial English language translation thereof.

*Asahi Shimbun Weekly AERA* "The novel pluripotent cells established by Professor Yamanaka of Kyoto University may change medical care" pp. 72-73, Dec. 24, 2007, along with a partial English language translation thereof.

U.S. Appl. No. 12/457,356, filed Jun. 9, 2009 to Yamanaka, entitled "Nuclear Reprogramming Factor and Induced Pluripotent Stem Cells."

Kim et al., "Generation of Human Induced Pluripotent Stem Cells by Direct Delivery of Reprogramming Proteins" *Cell Stem Cell* 4:472-476, 2009.

Ziegler et al., "The Cationic Cell-Penetrating Peptide CPP$^{TAT}$ Derived from the HIV-1 Protein TAT Is Rapidly Transported into Living Fibroblasts: Optical, Biophysical, and Metabolic Evidence" *Biochemisny* 44:138-148, published online Dec. 14, 2004.

Zhou et al., "Generation of Induced Pluripotent Stem Cells Using Recombinant Proteins" *Cell Stem Cell* 4:381-384, 2009.

Wadia et al., "Protein Transduction Technology" *Curr. Opin. Biotechnol.* 13:52-56, 2002.

Cosmo Bio News 49:5, 2005 (catalog of ES cell culture medium).

BioPorter™ Gene Therapy System, Inc., Wako Bio Window 40:7, 2002.

BioPorter™ Protein Delivery Reagent from www.biocarta.com.

Wakayama et al., "Differentiation of Embryonic Stem Cell Lines Generated from Adult Somatic Cells by Nuclear Transfer" *Science* 292:740-43, 2001.

Amsellem et al., "Ex vivo Expansion of Human Hematopoietic Stem Cells by Direct Delivery of the HOXB4 Homeoprotein" *Nat. Med.* 9(11):1423-27, 2003.

Krosl et al., "In vitro Expansion of Hematopoietic Stem Cells by Recombinant TAT-HOXB4 Protein" *Nat. Med.* 9(11):1428-32, 2003.

Tsunoda, Y., et al., The Recent Progress on Nuclear Transfer in Mammals, *Zoological Science* 17:1177-1184, 2000.

Wu et al., Sall4 Interacts With Nanog and Co-Occupies Nanog Genomic Sites in Embryonic Stem Cells, *J. Biol. Chem.*, 281(34):24090-24094, 2000.

Jaenisch et al., Stem Cells, the Molecular Circuitry of Pluripotency and Nuclear Reprogramming, Cell, 2008, vol. 132, pp. 567-582.

Liu, S.V., iPS Cells: a More Critical Review, Stem Cells and Development, 2008, pp. 1-11.

Yamanaka et al., Method of Nuclear Reprogramming, U.S. Appl. No. 12/733,118, Feb. 12, 2010.

Yamanaka, Nuclear Reprogramming Factor and Induced Pluripotent Stem Cells, U.S. Appl. No. 12/656,907, Feb. 18, 2010.

Yamanaka, Nuclear Reprogramming Factor and Induced Pluripotent Stem Cells, U.S. Appl. No. 12/656,908, Feb. 18, 2010.

Yamanaka, S., Induction of Pluripotent Stem Cells From Mouse Fibroblasts by Four Transcription Factors, Cell Proliferation, 2008, vol. 41, Issue (Suppl. 1), pp. 51-56.

Official Action issued in connection with Canadian Patent Application No. 2,632,142.

Official Action issued in connection with New Zealand Patent Application No. 569530.

A reprogramming rush. Editorial. Nature. Mar. 27, 2008. 452:388. Published online Mar. 26, 2008.

Adachi et al. Role of SOX2 in maintaining pluripotency of human embryonic stem cells. Genes Cells. May 2010; 15(5):455-70.

Allergucci et al. Differences between human embryonic stem cell lines. Hum Reprod Update. Mar.-Apr. 2007;13(2):103-20.

Altschul et al. Gapped BLAST and PSI-BLAST: a new generation of protein database search programs. Nucleic Acids Research. 1997;25(17): 3389-3402.

Anderson et al. Transgenic enrichment of cardiomyocytes from human embryonic stem cells. Mol Ther. Nov. 2007; 15(11):2027-36.

Assady et al. Insulin production by human embryonic stem cells. Diabetes. Aug. 2001;50(8): 1691-7.

Assou et al. A meta-analysis of human embryonic stem cells transcriptome integrated into a web-based expression atlas. Stem Cells. Apr. 2007;25(4):961-73.

Bader et al. Leukemia inhibitory factor modulates cardiogenesis in embryoid bodies in opposite fashions. Circ Res. Apr. 14, 2000;86(7):787-94.

Bagutti et al. Differentiation of embryonal stem cells into keratinocytes: comparison of wild-type and beta 1 integrin-deficient cells. Dev Biol. Oct. 10, 1996; 179(1): 184-96.

Barrett et al. NCBI GEO: mining tens of millions of expression profiles—database and tools update. Nucleic Acids Res. Jan. 2007;35(Database issue):D760-S.

Berg et al. An argument against a role for Oct4 in somatic stem cells. Cell Stem Cell. Oct. 11, 2007;1(4):359-60.

Birnbaum et al. Slicing across Kingdoms: Regeneration in Plants and Animals. Cell. Feb. 22, 2008; 132(4):697-710.

Blow, N. Stem cells: in search of common ground. Nature. Feb. 14, 2008;451 (7180):855-8.

Bonetta, L. European Stem Cell Patents: Taking the moral High Road? Cell. Feb. 22, 2008; 132(4):SI4-S16.

Brüstle et al. Embryonic stem cell-derived glial precursors: a source of myelinating transplants. Science. Jul. 30, 1999;285(5428):754-6.

Cai et al. Directed differentiation of human embryonic stem cells into functional hepatic cells. Hepatology. May 2007;45(5): 1229-39.

Chadwick et al. Cytokines and BMP-4 promote hematopoietic differentiation of human embryonic stem cells. Blood. Aug. 1, 2003; 102(3):906-15.

Chang et al. The c-Myc transactivation domain is a direct modulator of apoptotic versus proliferative signals. Mol Cell Biol. Jun. 2000;20(12):4309-19.

Childs et al. Regression of metastatic renal-cell carcinoma after nonmyeloablative allogeneic peripheral-blood stem-cell transplantation. N. Engl J Med. Sep. 14, 2000;343(11):750-8.

Chin et al. Induced pluripotent stem cells and embryonic stem cells are distinguished by gene expression signatures. Cell Stem Cell. Jul. 2, 2009;5(1): 111-23.

Cinalli et al. Germ Cells are Forever. Cell. Feb. 22, 2008; 132(4):559-562.

CIRM Public Release. $24 Million in New Stem Cell Research Funding Awarded to 25 California Institutions. California Institute for Regenerative Medicine (4 pages). Jun. 27, 2008.

Cline et al. Randomize Gene Sequences with New PCR Mutagenesis Kit. Strategies Newsletter. 2000; 13: 157-161.

Cyranoski, D. Stem cells: 5 things to know before jumping on the iPS bandwagon. Nature. 2008;452(7186)406-408.

Cyranoski. Japan ramps up patent effort to keep iPS lead. Nature. 2008; 453(7198):962-3.

Daley et al. Prospects for Stem Cell Based Therapy. Cell. Feb. 22, 2008; 132(4):544-548.

Dani, et at Differentiation of embryonic stem cells into adipocytes in vitro. J Cell Sci. Jun. 1997;110 (Pt 11):1279-85.

Dewitt et al. "Diversomers": an approach to nonpeptide, nonoligomeric chemical diversity. Proc Natl Acad Sci USA. Aug. 1, 1993;90(15):6909-13.

Dimos et al. Induced pluripotent stem cells generated from patients with ALS can be differentiated into motor neurons. Science. Aug. 29, 2008;321(5893):1218-21.

D'Ippolito et al. Marrow-isolated adult multilineage inducible (MIAMI) cells, a unique population of postnatal young and old human cells with extensive expansion and differentiation potential. J Cell Sci. Jun. 15, 2004; 117(Pt 14):2971-81.

Ehrich et al. Quantitative high-throughput analysis of DNA methylation patterns by base-specific cleavage and mass spectrometry. Proc Natl Acad Sci USA. Nov. 1, 2005; 102(44): 15785-90.

Eisen et al. Cluster analysis and display of genome-wide expression patterns. Dec. 8, 1998;95(25): 14863-14868.

Evans et al. Krüppel-like factor 4 is acetylated by p300 and regulates gene transcription via modulation of histone acetylation. J Biol Chem. Nov. 23, 2007;282(47): 33994-4002.

Felgner et al. Lipofection: a highly efficient, lipid-mediated DNA-transfection procedure. Proc Natl Acad Sci USA. Nov. 1987;84(21):7413-7.

Ferrer-Costa et al. PMUT: a web-based tool for the annotation of pathological mutations on proteins. Bioinformatics. Jul. 15, 2005;21(14):3176-8.

Gu et al. Opposite regulation of gene transcription and cell proliferation by c-Myc and Max. Proc Nat! Acad Sci USA. Apr. 1, 1993;90(7):2935-9.

Ha et al. Cryopreservation of human embryonic stem cells without the use of a programmable freezer. Hum Reprod. Jul. 2005;20(7): 1779-85.

Hanna et al. Direct Reprogramming of Terminally Differentiated Mature B Lymphocytes to Pluripotency. Cell. Apr. 18, 2008;133: 250-264. Erratum in: Cell. 2008; 134(2):365.

Hermann et al. Efficient generation of neural stem cell-like cells from adult human bone marrow stromal cells. J Cell Sci. Sep. 1, 2004; 117(Pt 19):4411-22.

Hockemeyer et al. A drug-inducible system for direct reprogramming of human somatic cells to pluripotency. Cell Stem Cell. Sep. 11, 2008;3(3):346-53.

Jaenisch et al. Stem Cells, the Molecular Circuitry of Pluripotency and Nuclear Reprogramming. Cell. Feb. 22, 2008; 132(4):567-582.

Jiang et al. In vitro derivation of functional insulin-producing cells from human embryonic stem cells. Cell Res. Apr. 2007; 17(4):333-44.

Johnston et al. Minimum requirements for efficient transduction of dividing and nondividing cells by feline immunodeficiency virus vectors. J Virol. Jun. 1999;73(6):4991-5000.

Kamachi, et at. Mechanism of regulatory target selection by the SOX high-mobility-group domain proteins as revealed by comparison of SOX1/2/3 and SOX9. Mol. Cell Biol. Jan. 1999;19(1):107-20.

Kanegae et al. Efficient gene activation in mammalian cells by using recombinant adenovirus expressing site-specific Cre recombinase. Nucleic Acids Res. Oct. 11, 1995;23(19):3816-21.

Kehat et al. Human embryonic stem cells can differentiate into myocytes with structural and functional properties of cardiomyocytes. J Clin Invest. Aug. 2001; 108(3):407-14.

Nagy et al. Embryonic stem cells alone are able to support fetal development in the mouse. Development. Nov. 1990:110(3):815-21.

Nakatake et al. Klf4 cooperates with Oct3/4 and Sox2 to activate the Lefty1 core promoter in embryonic stem cells. Mol Cell Biol. Oct. 2006;26(20):7772-82.

Needleman et al. A general method applicable to the search for similarities in the amino acid sequence of two proteins. J Mol Biol. Mar. 1970;48(3):443-53.

Ng et al. Predicting the effects of amino acid substitutions on protein function. Annu Rev Genomics Hum Genet. 2006;7:61-80.

Okita et al. Intracellular Signaling Pathways Regulating Pluripotency of Embryonic Stem Cells. Current Stem Cell Research & Therapy. 2006;1:103-111.

Orkin et al. Hematopoiesis: An Evolving Paradigm for Stem Cell Biology. Cell. Feb. 22, 2008; 132(4):631-644.

Osuna et al. Protein evolution by codon-based random deletions. Nucleic Acids Res. Sep. 30, 2004; 32(17):e136.

Padmanabhan et al. Visualization of telomerase reverse transcriptase (hTERT) promoter activity using a trimodality fusion reporter construct. J Nucl Med. Feb. 2006;47(2):270-7.

Park et al. Disease-specific induced pluripotent stem cells. Cell. Sep. 5, 2008; 134(5):877-86.

Park, A. Stem-cell research: The quest resumes. Time Magazine. Feb. 9, 2009. Available at http://www.time.com/time/health/article/0,8599,1874717,00.html. Accessed Jun. 3, 2009.

Parson, A.B. Stem Cell Biotech: Seeking a Piece of the Action. Cell. Feb. 22, 2008; 132(4):511-513.

Pear et al. Production of high-titer helper-free retroviruses by transient transfection. Proc. Natl. Acad. Sci. USA, vol. 90, pp. 8392-8396.

Pearson et al. Improved tools for biological sequence comparison. Proc Natl Acad Sci USA. Apr. 1988;85(8):2444-8.

Pearson, W.R. Rapid and sensitive sequence comparison with FASTP and FASTA. Methods Enzymol. 1990;183:63-98.

Pomp et al. Generation of peripheral sensory and sympathetic neurons and neural crest cells from human embryonic stem cells. Stem Cells. Aug. 2005;23(7):923-30.

Ratajczak et al. Bone-marrow-derived stem cells—our key to longevity? J. Appl. Genet. 2007;48(4): 307-319.

Reubinoff et al. Neural progenitors from human embryonic stem cells. Nat Biotechnol. Dec. 2001; 19(12):1134-40.

Riviére et al. Effects of retroviral vector design on expression of human adenosine deaminase in murine bone marrow transplant recipients engrafted with genetically modified cells. Proc Natl Acad Sci USA. Jul. 18, 1995;92(15):6733-7.

Rodda et al. Transcriptional regulation of nanog by OCT4 and SOX2. J Biol Chem. Jul. 1, 2005;280(26):24731-7.

Rodriguez et al., Manipulation of OCT4 Levels in Human Embryonic Stem Cells Results in Induction of Differential Cell Types. Experimental Biology and Medicine, 2007, vol. 232, pp. 1368-1380.

Root et al. Genome-scale loss-of-function screening with a lentiviral RNAi library. Nat Methods. Sep. 2006;3(9):715-9.

Rossant, J. Stem Cell and Early Lineage Development. Cell. Feb. 22, 2008; 132(4):527-531.

Saldanha et al. Assessment of telomere length and factors that contribute to its stability. Eur J Biochem. Feb. 2003;270(3):389-403.

Scherr et al. Gene silencing by small regulatory RNAs in mammalian cells. Cell Cycle. Feb. 1, 2007;6(4):444-9.

Schuldiner et al. Induced neuronal differentiation of human embryonic stem cells. Brain Res. Sep. 21, 2001;913(2):201-5.

Schwenk et al. Hybrid embryonic stem cell-derived tetraploid mice show apparently normal morphological, physiological, and neurological characteristics. Mol Cell Biol. Jun. 2003;23(11):3982-9.

Science magazine names top 10 breakthroughs of 2008. Available at http://arstechnica.com/old/content/2008/12/isciencei-names-top-10-scientific-breakthroughs-of-2008.ars. Accessed May 19, 2009.

Shah, R. Pharmacogenetics in drug regulation: promise, potential and pitfalls. Philos Trans R Soc Lond B Biol Sci. Aug. 29, 2005; 360(1460):1617-1638.

Silva et al. Capturing Pluripotericy. Cell. Feb. 22, 2008; 132(4):532-536.

Silva et al. Profiling essential genes in human mammary cells by multiplex RNAi screening. Science. Feb. 1, 2008;319(5863):617-20.

Skottman et al. Culture conditions for human embryonic stem cells. Reproduction. Nov. 2006;132(5):691-8.

Stadler et al. Small RNAs: Keeping Stem Cells in Line. Cell. Feb. 22, 2008; 132(4):563-566.

Stojkovic et al. Derivation, growth and applications of human embryonic stem cells. Reproduction. Sep. 2004;128(3):259-67.

Swift et al. Rapid production of retroviruses for efficient gene delivery to mammalian cells using 293T cell-based systems. Current Protocols in Immunology, Supp. 31, 1999, pp. 10.17.14-10.17.29.

Tan et al. Changing viral tropism using immunoliposomes alters the stability of gene expression: implications for viral vector design. Mol Med. Mar.-Apr. 2007; 13(3-4):216-26.

Tantin et al. High-throughput biochemical analysis of in vivo location data reveals novel distinct classes of POU5FI(Oct4)/DNA complexes. Genome Res. Apr. 2008;18(4):631-9.

The Japan Times. Bayer team makes stem cells from skin. Apr. 12, 2008. Available at http://search.japantimes.co.jp/cgi-bin/nn20080412a5.html. Accessed May 19, 2009.

Time. The Top 10 Everything of 2008—1. First Neurons Created from ALS Patients. Available at http://www.time.com/time/specials/2008/top10/article/0, 30583,1855948_1863993,00. html. Accessed Dec. 15, 2008.

Troyanskaya et al. Nonparametric methods for identifying differentially expressed genes in microarray data. Bioinformatics. 2002;18(11): 1454-1461.

Tsai et al. In vivo immunological function of mast cells derived from embryonic stem cells: an approach for the rapid analysis of even embryonic lethal mutations in adult mice in vivo. Proc Natl Acad Sci USA. Aug. 1, 2000;97(16):9186-90.

Tzukerman et al. Identification of a novel transcription factor binding element involved in the regulation by differentiation of the human telomerase (hTERT) promoter. Mol Biol Cell. Dec. 2000;11(12):4381-91.

Ulloa-Montoya et al. Comparative transcriptome analysis of embryonic and adult stem cells with extended and limited differentiation capacity. Genome Biol. 2007;8(8):R163.

Vallier et al. Activin/Nodal and FGF pathways cooperate to maintain pluripotency of human embryonic stem cells. J Cell Sci. Oct. 1, 2005;118(Pt 19):4495-509.

Vermeesch et al. Guidelines for molecular karyotyping in constitutional genetic diagnosis. Eur J Hum Genet. Nov. 2007;15(11):1105-14.

Vogel, G. Breakthrough of the year. Reprogramming Cells. Science. Dec. 19, 2008;322(5909): 1766-7.

Wang et al. Inhibition of caspase-mediated anoikis is critical for bFGF-sustained culture of human pluripotent stem cells. J Biol Chem. Oct. 16, 2009. [Epub ahead of print].

Watson et al. Identifying Genes Regulated in a Myc-dependent Manner. J Biol Chem. Oct. 4, 2002;277(40):36921-30.

Werbowetski-Ogilvie et al. Characterization of human embryonic stem cells with features of neoplastic progression. Nat Biotechnol. Jan. 2009;27(1):91-7.

Wernig et al. c-Myc is dispensable for direct reprogramming of mouse fibroblast. Cell Stem Cell. 2008; 2, 10-12.

Wernig et al. In vitro reprogramming of fibroblasts into a pluripotent ES-cell-like state. Nature. Jul. 19, 2007;448:318-324.

Wernig et al. Neurons derived from reprogrammed fibroblasts functionally integrate into the fetal brain and improve symptoms of rats with Parkinson's disease. Proc Natl Acad Sci USA. Apr. 15, 2008;105(15):5856-61.

What are adult stem Cells? Stem Cell Information. The National Institutes of Health resource for stem cell research. 2007. Available at: http://stemcells.nih.gov/info/basics/basics4.asp. Accessed Jun. 4, 2007.

Wu et al. Origins and Fates of Cardiovascular Progenitor Cells. Cell. Feb. 22, 2008; 132(4):537-543.

Yamane et al. Derivation of melanocytes from embryonic stem cells in culture. Dev. Dyn. 1999;216:450-458.

Yamashita et al. Flk1-positive cells derived from embryonic stem cells serve as vascular progenitors. Nature. Nov. 2, 2000;408(6808):92-6.

Yu et al. Induced pluripotent stem cell lines derived from human somatic cells. Science. Dec. 21, 2007;318(5858):1917-20.

Yuasa et al. Transient inhibition of BMP signaling by Noggin induces cardiomyocyte differentiation of mouse embryonic stem cells. Nat Biotechnol. May 2005;23(5):607-11.

Zhang et al. In vitro differentiation of transplantable neural precursors from human embryonic stem cells. Nat Biotechnol. Dec. 2001;19(12):1129-33.

Zhao et al. Mechanisms and Functional Implications of Adult Neurogenesis. Cell. Feb. 22, 2008; 132(4):645-660.

Bayani et al. Multi-color FISH techniques. Curr. Protoc. Cell Biol. 2004; Chapter 22:Unit 22.5.

Becker-Hapak et al. Protein transduction: generation of full-length transducible proteins using the TAT system. Curr Protoc Cell Biol. May 2003;Chapter 20: Unit 20.2.

Bendall et al. IGF and FGF cooperatively establish the regulatory stem cell niche of pluripotent human cells in vitro. Nature. Aug. 30, 2007;448(7157): 1015-21.

Bigdeli et al., Adaptation of Human Embryonic Stem Cells to Feeder-Free and Matrix-Free Culture Conditions Directly on Plastic Surfaces. J. Biotec., 2008, vol. 133, pp. 146-153.

Boquest et al. Epigenetic programming of mesenchymal stem cells from human adipose tissue. Stem Cell Rev. 2006;2(4):319-29.

Brena et al. Quantitative assessment of DNA methylation: Potential applications for disease diagnosis, classification, and prognosis in clinical settings. J Mol Med. May 2006;84(5):365-77.

Burns et al. Diabetes mellitus: a potential target for stem cell therapy. Curr Stem Cell Res Ther. May 2006; 1 (2):255-66.

Buttery et al. Differentiation of osteoblasts and in vitro bone formation from murine embryonic stem cells. Tissue Eng. Feb. 2001;7(1):89-99.

Campbell et al. Phosphonate Ester Synthesis Using a Modified Mitsunobu Condensation. J. Org. Chem.1994;59: 658-660.

Chen et al. Analogous Organic-Synthesis of Small-Compound Libraries—Validation of Combinatorial Chemistry in Small-Molecule Synthesis. Journal of the American Chemical Society. 1994;116(6): 2661-2662.

Chen et al. From stem cells to oligodendrocytes: prospects for brain therapy. Stem Cell Rev. Dec. 2007;3(4):280-8.

Cho et al. An unnatural biopolymer. Science. Sep. 3, 1993;261 (5126): 1303-5.

CIRM: Summaries of Review for Applications to RFA 07-05. California Institute for Regenerative Medicine Web site. 2007. Available at: http://www.cirm.ca.gov/RFAlrfa_07-05/. Accessed Jul. 1, 2008.

Coutts et al. Stem cells for the treatment of spinal cord injury. Exp Neurol. Feb. 2008;209(2):368-77.

Cowling et al. Mechanism of transcriptional activation by the Myc oncoproteins. Semin Cancer Biol. Aug. 2006; 16(4):242-52.

D'Amour et al. Efficient differentiation of human embryonic stem cells to definitive endoderm. Nat Biotechnol. Dec. 2005;23(12):1534-41.

D'Amour et al. Production of pancreatic hormone-expressing endocrine cells from human embryonic stem cells. Nat Biotechnol. Nov. 2006;24(11): 1392-401.

Deb, et al. Embryonic Stem Cells: From Markers to Market. Feb. 2008; 11(1): 19-37.

Denker, H. W. Human embryonic stem cells: the real challenge for research as well as for bioethics is still ahead of us. Cells Tissues Organs. 2008;187(4):250-6.

Durcova-Hills et al. Induced reprogramming of human somatic cells into pluripotency: a new way how to generate pluripotent stem cells. Differentiation. Apr. 2008;76(4):323-5.

Ebert, L. Yamanaka scooped on iPS (stem cell) patent?!. TMCNews reports on Jan. 4, 2009. Available at http://ipbiz.blogspot.com/2009/01/yamanaka-scooped-on-ips-stemcell.html. Accessed May 19, 2009.

Elefanty, A. Ed. In this Issue . . . Stem Cell Research. 2008; 1:87.

Essentials of Stem Cell Biology, R. Lanza et al. Ed., 2006, Elsevier Academic Press, pp. 266-267.

Forsyth et al. Human Embryonic Stem Cell Telomere Length Impacts Directly on Clonal Progenitor Isolation Frequency. Rejuvenation Research. Feb. 2008;11(1):5-17.

Gallop et al. Applications of combinatorial technologies to drug discovery. 1. Background and peptide combinatorial libraries. J Med Chem. Apr. 29, 1994;37(9): 1233-51.

Goswami et al. Embryonic stem cell therapy. IDrugs. Oct. 2007;10(10):713-9.

Heng et al. Incorporating protein transduction domains (PTD) within intracellular proteins associated with the 'stemness' phenotype. Novel use of such recombinant 'fusion' proteins to overcome current limitations of applying autologous adult stem cells in regenerative medicine? Med Hypotheses. 2005;64(5):992-6.

Highfield, R. Dolly creator Proflan Wilmut shuns cloning. Available at http://www.telegraph.co.uk/earth/main.jhtml?xml=/earth/2007/11/16/scidolly116.xml. Accessed Nov. 12, 2008.

Huangfu et al. Efficient Induction of Pluripotent Stem Cells Using Small Molecule Compounds. Companion manuscript to U.S. Appl. No. 61/029,287.

Itsykson et al. Derivation of neural precursors from human embryonic stem cells in the presence of noggin. Mol Cell Neurosci. Sep. 2005;30(1):24-36.

Jahagirdar et al. Multipotent adult progenitor cell and stem cell plasticity. Stem Cell Rev. 2005;1(1):53-9.

Janssens et al. Autologous bone marrow-derived stem-cell transfer in patients with ST-segment elevation myocardial infarction: double-blind, randomised controlled trial. Lancet. Jan. 14, 2006;367(9505):113-21.

Jiang et al. A core Klf circuitry regulates self-renewal of embryonic stem cells. Nat Cell Biol. Mar. 2008; 10(3):353-60.

Jiang et al. Pluripotency of mesenchymal stem cells derived from adult marrow. Nature. Jul. 4, 2002;418(6893):41-9.

Kim et al. Ex vivo characteristics of human amniotic membrane-derived stem cells. Cloning Stem Cells. 2007 Winter;9(4):581-94.

Kitamura et al. Retrovirus-mediated gene transfer and expression cloning: powerful tools in functional genomics. Exp Hematol. Nov. 2003;31(11):1007-14.

Kitamura, T. New experimental approaches in retrovirus-mediated expression screening. Int J Hematol. Jun. 1998;67(4):351-9.

Klingemann, H. Discarded stem cells with a future? Expert Opin Biol Ther. Dec. 2006;6(12): 1251-4.

Knoblich, J.A. Mechanisms of Asymmetric Stem Cell Division. Cell. Feb. 22, 2008; 132(4):583-597.

Koch et al. Transduction of human embryonic stem cells by ecotropic retroviral vectors. Nucl Acids Res. 2006; 34, e120.

Kohge et al. Promotion of antigen-specific antibody production in murine B cells by a moderate increase in histone acetylation. Biochem Pharmacol. Nov. 15, 1998;56(10): 1359-64.

Kopsidas et al. RNA mutagenesis yields highly diverse mRNA libraries for in vitro protein evolution. BMC Biotechnol. Apr. 11, 2007;7:18.

Kramer et al. Embryonic stem cell-derived chondrogenic differentiation in vitro: activation by BMP-2 and BMP-4. Mech Dev. Apr. 2000;92(2):193-205.

Krausz, E. High-content siRNA screening. Mol Biosyst. Apr. 2007;3(4):232-40.

Kunath et al. FGF stimulation of the Erk1/2 signalling cascade triggers transition of pluripotent embryonic stem cells from self-renewal to lineage commitment. Development. Aug. 2007;134(16):2895-902.

Kuroda et al. Octamer and Sox Elements Are Required for Transcriptional cis Regulation of Nanog Gene Expression. Mol Cell Biol. Mar. 2005; 25(6):2475-2485.

Laird et al. Stem Cell Trafficking in Tissue Development, Growth, and Disease. Cell. Feb. 22, 2008; 132(4):612-630.

Lee et al. Efficient generation of midbrain and hindbrain neurons from mouse embryonic stem cells. Nat Biotechnol. Jun. 2000;18(6):675-9.

Lemken et al. Evidence for intercellular trafficking of VP22 in living cells. Mol Ther. Feb. 2007;15(2):310-9.

Lengner et al. The pluripotency regulator Oct4: a role in somatic stem cells? Cell Cycle. Mar. 2008;7(6):725-8.

Li et al. Small dsRNAs induce transcriptional activation in human cells. Proc Natl Acad Sci. 2006; 103, 17337-17342.

Lieschke et al. Development of functional macrophages from embryonal stem cells in vitro. Exp Hematol. Apr. 1995;23(4):328-34.

Lin-Goerke et al. PCR-based random mutagenesis using manganese and reduced dNTP concentration. Biotechniques. Sep. 1997;23(3):409-12.

Link et al. Therapeutic protein transduction of mammalian cells and mice by nucleic acid-free lentiviral nanoparticles. Nucleic Acids Res. Jan. 30, 2006;34(2):e16.

Littlewood et al. A modified oestrogen receptor ligand-binding domain as an improved switch for the regulation of heterologous proteins. Nucleic Acids Res. May 25, 1995;23(10):1686-90.

Loudig et al. Transcriptional co-operativity between distant retinoic acid response elements in regulation of Cyp26A1 inducibility. Biochem J. Nov. 15, 2005;392(Pt 1):241-8.

Ludwig et al. Derivation of human embryonic stem cells in defined conditions. Nat Biotechnol. Feb. 2006;24(2):185-7.

Lumelsky et al. Differentiation of embryonic stem cells to insulin-secreting structures similar to pancreatic islets. Science. May 18, 2001;292(5520):1389-94.

Lunde et al. Zebrafish pou5f1/pou2, homolog of mammalian Oct4, functions in the endoderm specification cascade. Curr Biol. Jan. 6, 2004;14(1):48-55.

Lungwitz et al. Polyethylenimine-based non-viral gene delivery systems. Eur J Pharm Biopharm. Jul. 2005;60(2):247-66.

Maherali et al. A high-efficiency system for the generation and study of human induced pluripotent stem cells. Cell Stem Cell. Sep. 11, 2008;3(3):340-5.

Masaki et al. Tendency of Pluripotential marker gene expression in colonies derived from human neonatal fibroblasts induced by the human iPS cell method. Stem Cell Researchr. 2008. doi: 10.1016/j. scr.2008.01.001 (Accepted Manuscript).

Mathe et al. Computational approaches for predicting the biological effect of p53 missense mutations: a comparison of three sequence analysis based methods. Nucleic Acids Res. Mar. 6, 2006;34(5):1317-25.

Mikkelsen et al. Dissecting direct reprogramming through integrative genomic analysis. Nature. Jul. 3, 2008;454(7200):49-55. Erratum in: Nature. 2008;454(7205):794.

Miyagishi et al. Strategies for generation of an siRNA expression library directed against the human genome. Oligonucleotides. 2003;13(5):325-33.

Miyoshi et al. Development of a self-inactivating lentivirus vector. J Virol. Oct. 1998;72(10):8150-7.

More California Dough—$23 Million—Rolls Out the Door for Stem Cell Research. California Stem Cell Report Web Site. 2005. Available at: http://californiastemcellreport.blogspot.com/2008/06/more-dough-25-million-rolls-out-door-in.html. Accessed Jul. 1, 2008.

Morgenstern et al. Advanced mammalian gene transfer: high titre retroviral vectors with multiple drug selection markers and a complementary helper-free packaging cell line. Nucleic Acids Res. Jun. 25, 1990; 18(12):3587-3596.

Morizane et al. From bench to bed: the potential of stem cells for the treatment of Parkinson's disease. Cell Tissue Res. Jan. 2008;331(1):323-36.

Morling et al. Enhanced transduction efficiency of retroviral vectors coprecipitated with calcium phosphate. Gene Ther. Sep. 1995;2(7):504-8.

Morrison, S.J. Stem Cells and Niches: Mechanisms that Promote Stem Cell Maintenance throughout Life. Cell. Feb. 22, 2008; 132(4):598-611.

Mummery et al. Differentiation of human embryonic stem cells to cardiomyocytes: role of coculture with visceral endoderm-like cells. Circulation. Jun. 3, 2003; 107(21):2733-40.

Murry et al. Differentiation of Embryonic Stem Cells to Clinically Relevant Populations: Lessons from Embryonic Development. Cell. Feb. 22, 2008; 132(4):661-680.

Naldini et al. In vivo gene delivery and stable transduction of nondividing cells by a lentiviral vector. Science. Apr. 12, 1996;272(5259):263-7.

Négre et al. Lentiviral vectors derived from simian immunodeficiency virus. Curr Top Microbiol Immunol. 2002;261:53-74.

Onishi et al. Applications of retrovirus-mediated expression cloning. Exp Hematol. Feb. 1996;24(2):324-9.

Pera, M.F. On the Road to Reprogramming. Stem Cell Research. 2008; 1:103-104.

Pralong et al. Cell fusion for reprogramming pluripotency: toward elimination of the pluripotent genome. Stem Cell Rev. 2006;2(4):331-40.

Prelle et al. Overexpression of insulin-like growth factor-II in mouse embryonic stem cells promotes myogenic differentiation. Biochem Biophys Res Commun. Nov. 2, 2000;277(3):631-8.

Rambhatla et al. Generation of hepatocyte-like cells from human embryonic stem cells. Cell Transplant. 2003;12(1):1-11.

Rosenfeld et al. Adenovirus-mediated transfer of a recombinant alpha 1-antitrypsin gene to the lung epithelium in vivo. Science. Apr. 19, 1991;252(5004):431-4.

Rossant, J. Stem Cells: The Magic Brew. Nature. Jul. 19, 2007;448, 260-262.

Rossi et al. Stem Cells and the Pathways to Aging and Cancer. Cell. Feb. 22, 2008; 132(4):681-696.

Rubin, L. Stem Cell and Drug Discovery: The Beginning of a New Era? Cell. Feb. 22, 2008; 132(4):549-552.

Sadowski et al. GAL4-VP16 is an unusually potent transcriptional activator. Nature. Oct. 6, 1988;335(6190):563-;4.

Sottile et al. In vitro osteogenic differentiation of human ES cells. Cloning Stem Cells. 2003;5(2):149-55.

Stewart et al. Mechanisms of self-renewal in human embryonic stem cells. Eur J Cancer. Jun. 2006;42(9):1257-72.

Strelchenko et al., Embryonic Stem Cells from Morula, Methods in Enzymology, 2006, vol. 418, pp. 93-108.

Sumi et al. Apoptosis and differentiation of human embryonic stem cells induced by sustained activation of c-Myc. Oncogene. Aug. 16, 2007;26(38):5564-76.

Tokuzawa et al. Utilization of Digital Differential Display to Identify Novel Targets of Oct3/4. In: Turksen, K., ed. Embryonic Stem Cell Protocols: vol. I: Isolation and Characterization. Humana Press; 2nd ed. Edition. Feb. 15, 2006: 223-231.

Trompeter, et. al. Rapid and highly efficient gene transfer into natural killer cells by nucleofection. J Immunol Methods. Mar. 1, 2003 ;274(1-2):245-56.

Wagner et al. Mesenchymal stem cell preparations—comparing apples and oranges. Stem Cell Rev. Dec. 2007;3(4):239-48.

Watanabe et al. A ROCK inhibitor permits survival of dissociated human embryonic stem cells. Nat Biotechnol. 2007; 25, 681-686.

Xu et al. Random mutagenesis libraries: optimization and simplification by PCR. Biotechniques. Dec. 1999;27(6):1102, 1104, 1106, 1108.

Yee et al. Generation of high-titer pseudotyped retroviral vectors with very broad host range. Methods Cell Biol. 1994;43 Pt A:99-112.

Zhan et al. Conservation and variation of gene regulation in embryonic stem cells assessed by comparative genomics. Cell Biochem Biophys. 2005;43(3):379-405.

Crouch, D.H., et al., Multiple Phenotypes Associated With Myc-Induced Transformation of Chick Embryo Fibroblasts Can Be Dissociated by a Basic Region Mutation, Nucleic Acids Research 24(16):3216-3221, 1996.

International Search Report and Written Opinion issued in PCT/JP2011/051685.

Nakagawa, M., et al., Promotion of Direct Reprogramming by Transformation-Deficient Myc., Proc. Natl. Acad. Sci. USA 107(32):14152-14157, Aug. 2010.

Sarid, J., et al., Evolutionarily Conserved Regions of the Human c-Myc Protein Can Be Uncoupled From Transforming Activity, Proc. Natl. Acad. Sci. USA 84(1):170-173, 1987.

Australian Examination Report on Patent Application No. 2006325975 to Kyoto University, issued Apr. 18, 2011.

Nagano et al., "Large-scale identification of proteins expressed in mouse embryonic stem cells," Proteomics 2005, 5, pp. 1346-1361.

Okumura-Nakanishi et al., "Oct-3/4 and Sox2 Regulate Oct-3/4 Gene in Embryonic Stem Cells," The Journal of Biological Chemistry, vols. 280, No. 7, Issue of Feb. 18, pp. 5307-5317 (2006).

Wakao et al., "Multilineage-differentiating stress-enduring (Muse) cells are a primary source of induced pluripotent stem cells in human fibroblasts," available at www.pnas.org/cgi/content/short/1100816108.

Bongso, A., et al., Isolation and Culture of Inner Cell Mass Cells From Human Blastocysts, Human Reproduction 9(11):2110-2117, 1994.

Rodriquez, R.T., et al., Manipulation of OCT4 Levels in Human Embryonic Stem Cells Results in Induction of Differential Cell Types, Experimental Biology and Medicine, 2007, vol. 232, pp. 1368-1380.

Essentials of Stem Cell Biology, R. Lanza et al., Ed., 2006, Elsevier Academic Press, pp. 266-267.

Strelchenko et al. Embryonic Stem Cells from Morula, Methods in Enzymology, 2006, vol. 418, pp. 93-108.

Belmonte et al. "Induced pluripotent stem cells and reprogramming: seeing the science through the hype." Nat Rev Genet. Dec. 2009;10(12):878-83. Epub Oct. 27, 2009.

Carey et al., "Reprogramming of murine and human somatic cells using a single polycistronic vector," Proc. Natl. Acad. Sci. USA, Jan. 6, 2009, vol. 106(1), pp. 157-162, Epub. Dec. 24, 2008. Erratum in: Proc. Natl. Acad. Sci. USA, Mar. 31, 2009, vol. 106(13), p. 5449.

Chang et al., Embryonic Stem Cells/Induced Pluripotent Stem Cells, Stem Cells, 2009, vol. 27, pp. 1042-1049.

Daley, et al., "Broader implications of defining standards for the pluripotency of iPSCs." Cell Stem Cell. Mar. 6, 2009;4(3):200-1; author reply 202.

Extended European Search Report issued in connection with European Patent Application No. 10154819.6, Jun. 10, 2010.

Extended European Search Report issued in connection with European Patent Application No. EP 06834636.0, Mar. 11, 2009.

Extended European Search Report issued in connection with European Patent Application No. EP 10154817.0, Jun. 10, 2010.
Extended European Search Report issued in connection with European Patent Application No. EP 10154821.2, Jun. 10, 2010.
Hakelien et al., Reprogramming Fibroblasts to Express T-cell Functions Using Cell Extracts, Nature Biotechnology, May 2002, vol. 20, pp. 460-466.
Hong et al., "Suppression of induced pluripotent stem cell generation by the p53-p21 pathway." Nature. Aug. 27, 2009;460(7259):1132-5. Epub Aug. 9, 2009.
Hsiao et al., Marking Embryonic Stem Cells With a 2A Self-Cleaving Peptide: A NKX2-5 Emerald GFP BAC Reporter, PLoS ONE 3(7):e2532, 2008.
Hyun et al., "New advances in iPS cell research do not obviate the need for human embryonic stem cells." Cell Stem Cell. Oct. 11, 2007;1(4):367-8.
International Search Report issued with respect to PCT/JP2009/058873, mailed Jul. 7, 2009.
Kaji et al., Virus-Free Induction of Pluripotency and Subsequent Excision of Reprogramming Factors, Nature, Mar. 1, 2009, vol. 458, Issue 7239, pp. 771-775.
Lewitzky et al., "Reprogramming somatic cells towards pluripotency by defined factors." Curr Opin Biotechnol. Oct. 2007;18(5):467-73.
Miura et al. "Variation in the safety of induced pluripotent stem cell lines." Nat Biotechnol. Aug. 2009;27(8):743-5. Epub Jul. 9, 2009.
Nakagawa et al., "Promotion of direct reprogramming by transformation-deficient Myc." Proc Natl Acad Sci U S A. Aug. 10, 2010;107(32):14152-7. Epub Jul. 26, 2010.
Office Action issued in connection with Chinese Patent Application No. 200680048227.7, Sep. 14, 2010.
Office Action issued in connection with European Patent Application No. EP 06834636.0, Apr. 30, 2010.
Office Action issued in connection with European Patent Application No. EP 06834636.0, Oct. 25, 2010.
Office Action issued in connection with Israeli Patent Application No. 191903, Aug. 19, 2010.
Office Action issued in connection with Japanese Patent Application No. JP 2009-056747, mailed Jun. 2, 2009.
Office Action issued in connection with Japanese Patent Application No. JP 2009-056748, mailed Jun. 2, 2009.
Official Action issued in connection with Japanese Patent Application No. JP 2009-056748, mailed Nov. 4, 2009.
Official Rejection issued in connection with Japanese Patent Application No. JP 2009-056748, mailed Feb. 23, 2010.
Office Action issued in connection with Japanese Patent Application No. JP 2009-056749, mailed Jun. 4, 2009.
Official Rejection issued in connection with Japanese Patent Application No. JP 2009-056749, mailed Nov. 4, 2009.
Office Action issued in connection with Japanese Patent Application No. JP 2009-056750, mailed Jun. 2, 2009.
Office Action issued in connection with New Zealand Patent Application No. 569530, Apr. 20, 2010.
Office Action issued in connection with Singapore Patent Application No. 200804231-9, Apr. 13, 2010.
Office Action issued in connection with Singapore Patent Application No. 200901803-7, Jan. 22, 2010.
Official Action issued in connection with Eurasian Patent Application No. 200870046, Nov. 9, 2009.
Official Action issued in connection with Eurasian Patent Application No. 201000858, Jul. 14, 2010.
Ohnuki et al., "Generation and characterization of human induced pluripotent stem cells." Curr Protoc Stem Cell Biol. Jun. 2009;Chapter 4:Unit 4A.2.
Okabe et al., Green Mice as a Source of Ubiquitous Green Cells, FEBS Letters, 1997, vol. 407, pp. 313-319.
Okita et al., "Generation of mouse-induced pluripotent stem cells with plasmid vectors." Nat Protoc. 2010;5(3):418-28. Epub Feb. 11, 2010.
Okita et al., "Induction of pluripotency by defined factors." Exp Cell Res. Oct. 1, 2010;316(16):2565-70. Epub Apr. 24, 2010.

Peister et al., Gene Ther, Jan. 2004, vol. 11, Issue 2, pp. 224-228.
Quenneville et al., Mol. Ther., Oct. 2004, vol. 10, Issue 4, pp. 679-687.
Shao et al., Generation of iPS Cells Using Defined Factors Linked Via the Self-Cleaving 2A Sequences in a Single Open Reading Frame, Cell Res., Mar. 2009, vol. 19, Issue 3, pp. 296-312.
Soldner et al., Parkinson's Disease Patient-Derived Induced Pluripotent Stem Cells Free of Viral Reprogramming Factors, Cell, Mar. 6, 2009, vol. 136, Issue 5, pp. 964-977.
Takahashi, K. et al. "Human induced pluripotent stem cells on autologous feeders." PLoS One. Dec. 2, 2009;4(12):e8067.
Takeda et al., Characterization of Dental Pulp Stem Cells of Human Tooth Germs, Journal of Dental Research, 2008, vol. 87, pp. 676-681.
Tsubooka et al. "Roles of Sall4 in the generation of pluripotent stem cells from blastocysts and fibroblasts." Genes Cells. Jun. 2009;14(6):683-94. Epub May 19, 2009.
Woltjen et al., PiggyBac Transposition Reprograms Fibroblasts to Induced Pluripotent Stem Cells, Nature, Mar. 1, 2009, vol. 458, Issue 7239, pp. 766-770.
Xu et al., "BMP4 initiates human embryonic stem cell differentiation to trophoblast." Nature Biotechnology, Dec. 2002, vol. 20, pp. 1261-1264.
Yamanaka et al., "Nuclear reprogramming to a pluripotent state by three approaches." Nature. Jun. 10, 2010;465(7299):704-12.
Yamanaka S., "An interview with . . . Shinya Yamanaka. Interview by Mary Muers." Nat Rev Genet. Jun. 2010;11(6):390. Epub May 5, 2010.
Yamanaka S., "Patient-specific pluripotent stem cells become even more accessible" Cell Stem Cell. Jul. 2. 2010;7(1):1-2.
Yamanaka S., "Pluripotency and nuclear reprogramming." Philos Trans R Soc Lond B Biol Sci. Jun. 27, 2008;363(1500):2079-87.
Yamanaka S., "Symposium: Nuclear reprogramming and the control of differentiation in mammalian embryos. Introduction." Reprod Biomed Online. Jan. 2008;16(1):11-2.
Yamanaka, S., "A fresh look at iPS cells." Cell. Apr. 3, 2009;137(1):13-7.
Yamanaka, S., "Ekiden to iPS Cells." Nat Med. Oct. 2009;15(10):1145-8.
Yamanaka, S., "Elite and stochastic models for induced pluripotent stem cell generation." Nature. Jul. 2, 2009;460(7251):49-52.PMID: 19571877 [PubMed—indexed for MEDLINE]Related citations.
Yamanaka, S., "Induction of Pluripotency by Defined Factors—The History of iPS Cells", Gairdner Award acceptance speech, presented on or about Oct. 29, 2009.
Yamanaka, S., "Induction of Pluripotency by Defined Factors", lecture presented on or about Oct. 29, 2009.
Yoshida et al. "Hypoxia enhances the generation of induced pluripotent stem cells." Cell Stem Cell. Sep. 4, 2009;5(3):237-41. Epub Aug. 27, 2009.
Yoshida et al., "Recent stem cell advances: induced pluripotent stem cells for disease modeling and stem cell-based regeneration." Circulation. Jul. 6, 2010;122(1):80-7.
Kim et al., "Oct4-Induced Pluripotency in Adult Neural Stem Cells" *Cell* 136:411-419, 2009.
Kim et al., "Pluripotent Stem Cells Induced From Adult Neural Stem Cells by Reprogramming with Two Factors" *Nature* 454:646-650, 2008.
Huangfu et al., "Induction of Pluripotent Stem Cells From Primary Human Fibroblasts with Only *Oct4* and *Sox 2*" *Nature Biotechnology* 26:1269-1275, 2008.
Feng et al., "Reprogramming of Fibroblasts into Induced Pluripotent Stem Cells with Orphan Nuclear Receptor Esrrb" *Nature Cell Biology* 11:197-203, 2009.
Mali et al. "Improved Efficiency and Pace of Generating Induced Pluripotent Stem Cells from Human Adult and Fetal Fibroblasts" *Stem Cells* 26:1998-2005, 2008.
Yu et al., "Human Induced Pluripotent Stem Cells Free of Vector and Transgene Sequences" *Science* 324:797-801, 2009.

\* cited by examiner

Fig. 20
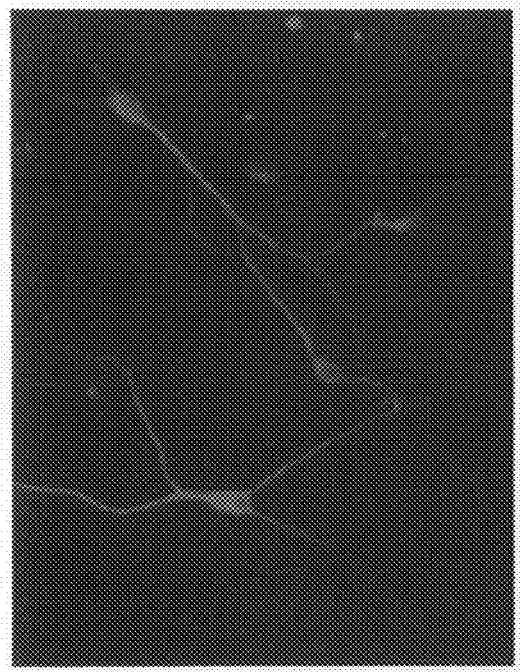
Neuron (βIII tubulin)
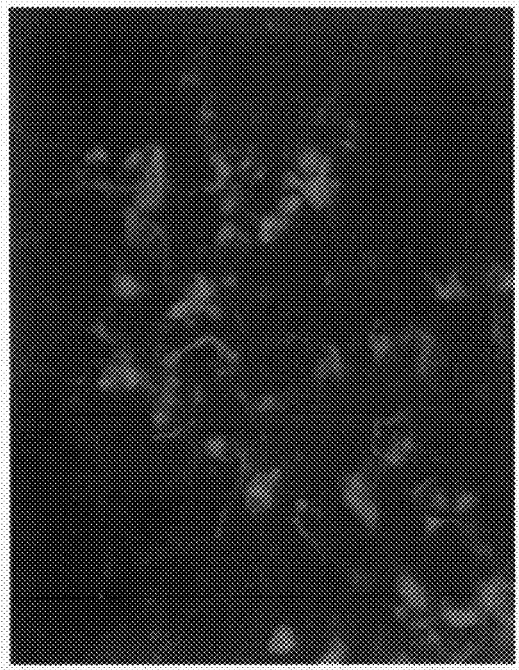
Astrocyte (GFAP)
Oligodendrocyte (O4)

Fig. 23
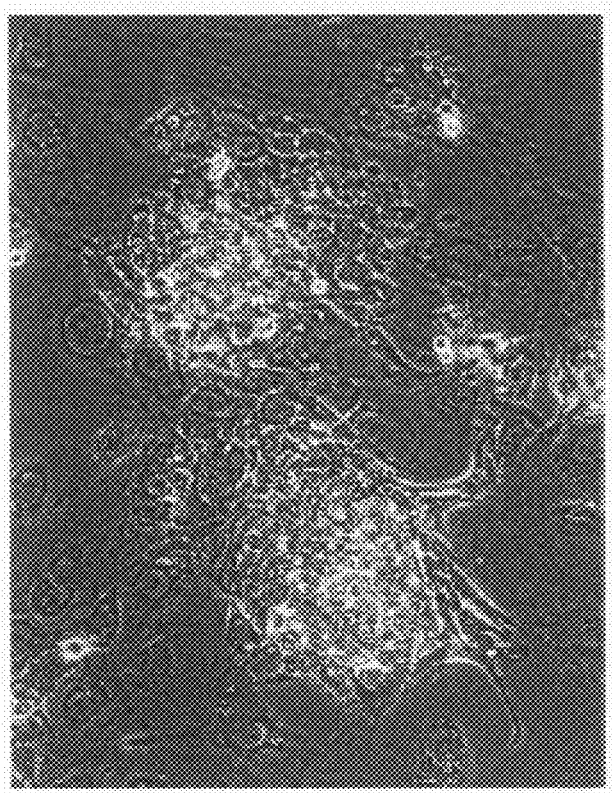
After passages (Passage 2)
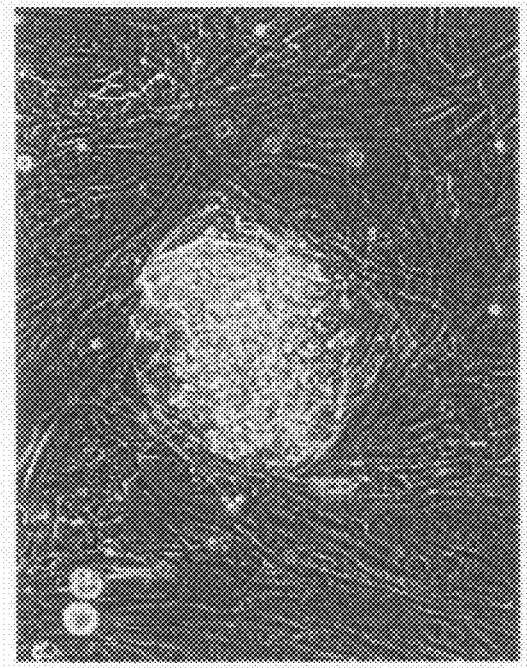
Colony

SEQUENCE LISTING

```
<160> NUMBER OF SEQ ID NOS: 25

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgtggggccc tgaaaggcga gctgagat                                      28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgggccgcc atacgacgac gctcaact                                      28

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaagtctggt tccttggcag gatg                                          24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
actcgataca ctggcctagc                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
caggtgtttg agggtagctc                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggttcatca tggtacagtc                                                    20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
actgcccctc atcagactgc tact                                               24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cactgccttg tactcgggta gctg                                               24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gttccaacct gtgcctcgcg tctt                                               24

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agcgaggcat ggagagagcg gagcag                                             26

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
```

```
cgtggtgagc atcttcggag tgg                                            23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccttcttggt ccgcccgttc tta                                            23

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atggacgcaa ctgtgaacat gatgttcgca                                     30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctttgaggtc ctggtccatc acgtgaccat                                     30

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccattagggg ccatcatcgc tttc                                           24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cactgctcac tggaggggc ttgc                                            24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgctgcggtc caggccatca agag                                           24
```

```
<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggcactgtt cagttcagcg gatc                                           24

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tctttccacc aggccccggg ctc                                            23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgcgggcgga catggggaga tcc                                            23

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
attcttcgtt gtcaagccgc caaagtggag                                     30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agttgtttgc tgcggagttg tcatctcgtc                                     30

<210> SEQ ID NO 23
<211> LENGTH: 2127
<212> TYPE: DNA
<213> ORGANISM: Simian virus 40

<400> SEQUENCE: 23
atggataaag tttttaaacag agaggaatct tgcagctaa tggaccttct aggtcttgaa    60
aggagtgcct gggggaatat tcctctgatg agaaaggcat atttaaaaaa atgcaaggag   120
tttcatcctg ataaaggagg agatgaagaa aaaatgaaga aatgaatac tctgtacaag   180 aaaatggaag atggagtaaa atatgctcat caacctgact ttggaggctt ctgggatgca   240
```

```
actgagattc aacctatgg aactgatgaa tgggagcagt ggtggaatgc ctttaatgag    300
gaaaacctgt tttgctcaga agaaatgcca tctagtgatg atgaggctac tgctgactct    360
caacattcta ctcctccaaa aaagaagaga aaggtagaag accccaagga ctttccttca    420
gaattgctaa gtttttttgag tcatgctgtg tttagtaata gaactcttgc ttgctttgct    480
atttacacca caaaggaaaa agctgcactg ctatacaaga aaattatgga aaaatattct    540 gtaacctttta taagtaggca taacagttat aatcataaca tactgttttt tcttactcca    600
cacaggcata gagtgtctgc tattaataac tatgctcaaa aattgtgtac ctttagcttt    660
ttaatttgta aaggggttaa taaggaatat ttgatgtata gtgccttgac tagagatcca    720 tttctgtta ttgaggaaag tttgccaggt gggttaaagg agcatgattt taatccagaa    780
gaagcagagg aaactaaaca agtgtcctgg aagcttgtaa cagagtatgc aatggaaaca    840
aaatgtgatg atgtgttgtt attgcttggg atgtacttgg aatttcagta cagttttgaa    900
atgtgtttaa aatgtattaa aaaagaacag cccagccact ataagtacca tgaaaagcat    960
tatgcaaatg ctgctatatt tgctgacagc aaaaaccaaa aaaccatatg ccaacaggct    1020
gttgatactg ttttagctaa aaagcgggtt gatagcctac aattaactag agaacaaatg    1080
ttaacaaaca gatttaatga tcttttggat aggatggata taatgtttgg ttctacaggc    1140
tctgctgaca tagaagaatg gatggctgga gttgcttggc tacactgttt gttgcccaaa    1200
atggattcag tggtgtatga cttttttaaaa tgcatggtgt acaacattcc taaaaaaga    1260 tactggctgt ttaaaggacc aattgatagt ggtaaaacta cattagcagc tgctttgctt    1320
gaattatgtg gggggaaagc tttaaatgtt aatttgccct tggacaggct gaactttgag    1380
ctaggagtag ctattgacca gttttttagta gttttttgagg atgtaaaggg cactggaggg    1440
gagtccagag atttgccttc aggtcaggga attaataacc tggacaattt aagggattat    1500
ttggatggca gtgttaaggt aaacttagaa aagaaacacc taaataaaag aactcaaata    1560 tttcccctg gaatagtcac catgaatgag tacagtgtgc ctaaaacact gcaggccaga    1620
tttgtaaaac aaatagattt taggcccaaa gattatttaa agcattgcct ggaacgcagt    1680 gagttttgt tagaaaagag aataattcaa agtggcattg ctttgcttct tatgttaatt    1740
tggtacagac ctgtggctga gtttgctcaa agtattcaga gcagaattgt ggagtggaaa    1800
gagagattgg acaaagagtt tagtttgtca gtgtatcaaa aaatgaagtt taatgtggct    1860
atgggaattg gagttttaga ttggctaaga aacagtgatg atgatgatga agacagccag    1920
gaaaatgctg ataaaaatga agatggtggg gagaagaaca tggaagactc agggcatgaa    1980
acaggcattg attcacagtc ccaaggctca tttcaggccc ctcagtcctc acagtctgtt    2040
catgatcata tcagccata ccacatttgt agaggtttta cttgctttaa aaaacctccc    2100
acacctcccc ctgaacctga aacataa    2127
```

<210> SEQ ID NO 24  
<211> LENGTH: 456  
<212> TYPE: DNA  
<213> ORGANISM: Human papillomavirus type 16

<400> SEQUENCE: 24

```
atgtttcagg acccacagga gcgacccaga aagttaccac agttatgcac agagctgcaa     60
acaactatac atgatataat attagaatgt gtgtactgca agcaacagtt actgcgacgt    120
gaggtatatg actttgcttt tcgggattta tgcatagtat atagagatgg gaatccatat    180
gctgtatgtg ataaatgttt aaagttttat tctaaaatta gtgagtatag acattattgt    240
```

```
tatagtttgt atggaacaac attagaacag caatacaaca aaccgttgtg tgatttgtta    300
attaggtgta ttaactgtca aaagccactg tgtcctgaag aaaagcaaag acatctggac    360
aaaaagcaaa gattccataa tataagggt cggtggaccg gtcgatgtat gtcttgttgc    420
agatcatcaa gaacacgtag agaaacccag ctgtaa                              456

<210> SEQ ID NO 25
<211> LENGTH: 297
<212> TYPE: DNA
<213> ORGANISM: Human papillomavirus type 16

<400> SEQUENCE: 25
atgcatggag atacacctac attgcatgaa tatatgttag atttgcaacc agagacaact     60
gatctctact gttatgagca attaaatgac agctcagagg aggaggatga aatagatggt    120
ccagctggac aagcagaacc ggacagagcc cattacaata ttgtaacctt ttgttgcaag    180
tgtgactcta cgcttcggtt gtgcgtacaa agcacacacg tagacattcg tactttggaa    240
gacctgttaa tgggcacact aggaattgtg tgccccatct gttctcagaa accataa       297
```

NUCLEAR REPROGRAMMING FACTOR

TECHNICAL FIELD

The present invention relates to a nuclear reprogramming factor having an action of reprogramming a differentiated somatic cell to derive an induced pluripotent stem cell.

BACKGROUND ART

Embryonic stem cells (ES cells) are stem cells established from human or mouse early embryos which have a characteristic feature that they can be cultured over a long period of time while maintaining pluripotent ability to differentiate into all kinds of cells existing in living bodies. Human embryonic stem cells are expected for use as resources for cell transplantation therapies for various diseases such as Parkinson's disease, juvenile diabetes, and leukemia, taking advantage of the aforementioned properties. However, transplantation of ES cells has a problem of causing rejection in the same manner as organ transplantation. Moreover, from an ethical viewpoint, there are many dissenting opinions against the use of ES cells which are established by destroying human embryos. If dedifferentiation of patients' own differentiated somatic cells could be induced to establish cells having pluripotency and growth ability similar to those of ES cells (in this specification, these cells are referred to as "induced pluripotent stem cells (iPS cells)", though they are sometimes called "embryonic stem cell-like cells" or "ES-like cells"), it is anticipated that such cells could be used as ideal pluripotent cells, free from rejection or ethical difficulties.

As a method for reprogramming a somatic nucleus, for example, a technique of establishing an embryonic stem cell from a cloned embryo, prepared by transplanting a nucleus of a somatic cell into an egg, was reported (W. S. Hwang et al., Science, 303, pp. 1669-74, 2004; W. S. Hwang et al., Science, 308, pp. 1777-83, 2005: these articles were, however, proved to be fabrications and later withdrawn). However, this technique of preparing the cloned embryo only for the purpose of establishing ES cells, has rather more serious ethical problems when compared with ordinary ES cells using surplus embryos produced in fertilization therapy. A technique of reprogramming a somatic cell nucleus by fusing a somatic cell and an ES cell was also reported (M. Tada et al., Curr. Biol., 11, pp. 1553-1558, 2001; C. A. Cowan et al., Science, 309, pp. 1369-73, 2005). However, this method results in the use of human ES cells, which fails to provide a solution to the ethical difficulties. Further, a technique of reprogramming a cell nucleus by reacting an extract of a cell strain, derived from a germ cell tumor generated in a human, with a differentiated cell was reported (C. K. Taranger et al., Mol. Biol. Cell, 16, pp. 5719-35, 2005). However, it was completely unknown which component in the extract induced the reprogramming in this method, and therefore, this method has problems of technical reliability and safety.

A method for screening a nuclear reprogramming factor having an action of reprogramming differentiated somatic cells to derive induced pluripotent stems cell was proposed (International Publication WO2005/80598). This method comprises the steps of contacting somatic cells containing a gene, in which a marker gene is positioned so as to receive expression control by an expression control region of the ECAT (ES cell associated transcript) genes (i.e., a class of genes specifically expressed in ES cells), with each test substance; examining presence or absence of the appearance of a cell that expresses the marker gene; and choosing a test substance inducing the appearance of said cell as a candidate of a nuclear reprogramming factor for somatic cells. A method for reprogramming a somatic cell is disclosed in Example 6 and the like of the above publication. However, this publication fails to report an actual identification of a nuclear reprogramming factor.

Patent document 1: International Publication WO2005/80598

DISCLOSURE OF THE INVENTION

An object of the present invention is to provide a nuclear reprogramming factor. More specifically, it is an object of the present invention to provide a means for inducing reprogramming of a differentiated cell without using eggs, embryos, or ES cells, to conveniently and highly reproducibly establish an induced pluripotent stem cell having pluripotency and growth ability similar to those of ES cells.

The inventors of the present invention conducted various research to achieve the aforementioned object and attempted to identify a nuclear reprogramming factor by using the screening method for a nuclear reprogramming factor disclosed in International Publication WO2005/80598. As a result, 24 kinds of candidate genes were found as genes relating to nuclear reprogramming, and among them, three kinds of the genes were found as essential genes for nuclear reprogramming. The present invention was achieved on the basis of the aforementioned findings.

The present invention thus provides a nuclear reprogramming factor for a somatic cell, which comprises a gene product of each of the following three kinds of genes: an Oct family gene, a Klf family gene, and a Myc family gene. According to a preferred embodiment of the invention, there is provided the aforementioned factor comprising a gene product of each of the following three kinds of genes: Oct3/4, Klf4 and c-Myc.

According to another preferred embodiment, there is provided the aforementioned factor, which further comprises a gene product of the following gene: a Sox family gene, and as a more preferred embodiment, there is provided the aforementioned factor, which comprises a gene product of Sox2.

According to still another preferred embodiment, there is provided the aforementioned factor, which comprises a cytokine together with the gene product of the Myc family gene, or alternatively, instead of the gene product of the Myc family gene. As a more preferred embodiment, there is provided the aforementioned factor, wherein the cytokine is basic fibroblast growth factor (bFGF) and/or stem cell factor (SCF).

According to particularly preferred embodiments, there are provided a nuclear reprogramming factor for a somatic cell, which comprises a gene product of the TERT gene in addition to a gene product of each of an Oct family gene, a Klf family gene, a Myc family gene, and a Sox family gene; and the aforementioned factor, which comprises a gene product or gene products of one or more kinds of genes selected from the group consisting of the following genes: SV40 Large T antigen, HPV16 E6, HPV16 E7, and Bmil, in addition to a gene product of each of the Oct family gene, the Klf family gene, the Myc family gene, the Sox family gene, and the TERT gene.

In addition to these factors, there is provided the aforementioned factor, which further comprises a gene product or gene products of one or more kinds of genes selected from the group consisting of the following: Fbx15, Nanog, ERas, ECAT15-2, Tcl1, and β-catenin.

According to another preferred embodiment of the aforementioned invention, there is also provided the aforementioned factor, which comprises a gene product or gene products of one or more kinds of genes selected from the group consisting of the following: ECAT1, Esg1, Dnmt3L, ECAT8, Gdf3, Sox15, ECAT15-1, Fthl17, Sall4, Rex1, UTF1, Stella, Stat3, and Grb2.

In another aspect, the present invention provides a method for preparing an induced pluripotent stem cell by nuclear reprogramming of a somatic cell, which comprises the step of contacting the aforementioned nuclear reprogramming factor with the somatic cell.

According to a preferred embodiment of the invention, there are provided the aforementioned method, which comprises the step of adding the aforementioned nuclear reprogramming factor to a culture of the somatic cell; the aforementioned method, which comprises the step of introducing a gene encoding the aforementioned nuclear reprogramming factor into the somatic cell; the aforementioned method, which comprises, the step of introducing said gene into the somatic cell by using a recombinant vector containing at least one kind of gene encoding the aforementioned nuclear reprogramming factor; and the aforementioned method, wherein a somatic cell isolated from a patient is used as the somatic cell.

In another aspect, the present invention provides an induced pluripotent stem cell obtained by the aforementioned method. The present invention also provides a somatic cell derived by inducing differentiation of the aforementioned induced pluripotent stem cell.

The present invention further provides a method for stem cell therapy, which comprises the step of transplanting a somatic cell, wherein said cell is obtained by inducing differentiation of an induced pluripotent stem cell obtained by the aforementioned method using a somatic cell isolated and collected from a patient, into said patient.

The present invention further provides a method for evaluating a physiological function or toxicity of a compound, a medicament, a poison or the like by using various cells obtained by inducing differentiation of an induced pluripotent stem cell obtained by the aforementioned method.

The present invention also provides a method for improving ability of differentiation and/or growth of a cell, which comprises the step of contacting the aforementioned nuclear reprogramming factor with the cell, and further provides a cell obtained by the aforementioned method, and a somatic cell derived by inducing differentiation of a cell obtained by the aforementioned method.

By using the nuclear reprogramming factor provided by the present invention, reprogramming of a differentiated cell nucleus can be conveniently and highly reproducibly induced without using embryos or ES cells, and an induced pluripotent stem cell, as an undifferentiated cell having differentiation ability, pluripotency, and growth ability similar to those of ES cells, can be established. For example, an induced pluripotent stem cell having high growth ability and differentiation pluripotency can be prepared from a patient's own somatic cell by using the nuclear reprogramming factor of the present invention. Cells obtainable by differentiating said cell (for example, cardiac muscle cells, insulin producing cells, nerve cells and the like) are extremely useful, because they can be utilized for stem cell transplantation therapies for a variety of diseases such as cardiac insufficiency, insulin dependent diabetes mellitus, Parkinson's disease and spinal cord injury, thereby the ethical problem concerning the use of human embryo and rejection after transplantation can be avoided. Further, various cells obtainable by differentiating the induced pluripotent stem cell (for example, cardiac muscle cells, hepatic cells and the like) are highly useful as systems for evaluating efficacy or toxicity of compounds, medicaments, poisons and the like.

BRIEF EXPLANATION OF THE DRAWINGS

FIG. 20 shows induction of differentiation into nerve cells from iPS cells. Nerve cells (top, βIII tubulin-positive), oligodendrocytes (left, O4-positive), and astrocytes (right, GFAP-positive) differentiated in vitro from dermal fibroblasts-derived iPS cells are shown.

FIG. 23 shows iPS cell-like cells derived from human fibroblasts. The colonies obtained by retroviral transduction with human homologous genes of the 4 factors into fibroblasts derived from human embryos (left), and the cells after two passages (right) are shown.

BEST MODE FOR CARRYING OUT THE INVENTION

Figure 1:
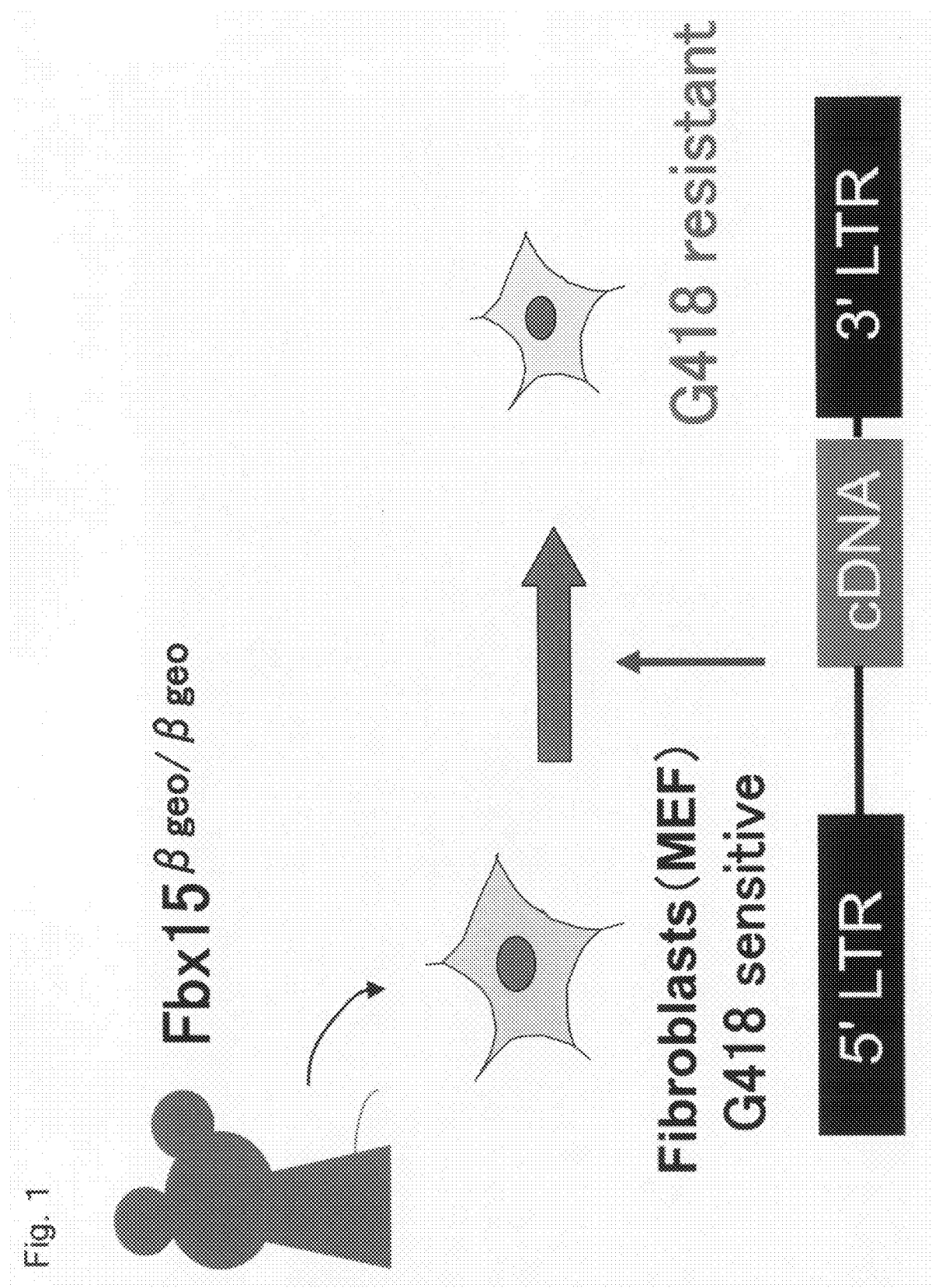
FIG. 1 shows a screening method for reprogramming factors using embryonic fibroblasts (MEFs) of a mouse having βgeo knockin Fbx15 gene.

The nuclear reprogramming factor of the present invention is characterized in that it comprises a gene product of each of the following three kinds of genes: an Oct family gene, a Klf family gene, and a Myc family gene; and according to a preferred embodiment, it is characterized in that it comprises a gene product of a Sox family gene in addition to the aforementioned three kinds of genes.

As a means for confirming the nuclear reprogramming factor of the present invention, for example, the screening method for nuclear reprogramming factors disclosed in International Publication WO 2005/80598 can be used. The entire disclosure of the aforementioned publication is incorporated into the disclosure of the specification by reference. By referring to the aforementioned publication, those skilled in the art can perform screening of nuclear reprogramming factors to confirm the existence and the action of the reprogramming factor of the present invention.

For example, as an experimental system enabling observation of the reprogramming phenomenon, a mouse can be used in which the βgeo (a fusion gene of the β galactosidase gene and the neomycin resistance gene) is knocked into the Fbx15 locus. The details are described in the examples of the specification. The mouse Fbx15 gene is a gene specifically expressed in differentiation pluripotent cells such as ES cells and early embryos. In a homomutant mouse in which βgeo is knocked into the mouse Fbx15 gene so as to be deficient in the Fbx15 function, abnormal phenotypes including those relating to differentiation pluripotency or generation are not generally observed. In this mouse, the expression of the βgeo is controlled by the enhancer and promoter of the Fbx15 gene, and differentiated somatic cells in which βgeo is not expressed have sensitivity to G418. In contrast, βgeo knockin homomutant ES cells have resistance against G418 at an extremely high concentration (higher than 12 mg/ml). By utilizing this phenomenon, an experimental system can be constructed to visualize reprogramming of somatic cells.

By applying the aforementioned experimental system, fibroblasts (Fbx15$^{\beta geo/\beta geo}$ MEFs) can be first isolated from an embryo of the βgeo knockin homomutant mouse (13.5 days after fertilization). The MEFs do not express the Fbx15 gene, and accordingly also do not express βgeo to give sensitivity to G418. However, when the MEFs are fused with genetic manipulation-free ES cells (also have sensitivity to G418), βgeo is expressed and the cells become G418-resistant as a result of reprogramming of nuclei of MEFs. Therefore, by utilizing this experimental system, the reprogramming phenomenon can be visualized as G418 resistance.

Nuclear reprogramming factors can be selected by using the aforementioned experimental system. As candidates of genes relevant to nuclear reprogramming factors, a plurality of genes can be selected which show specific expression in ES cells or of which important roles in the maintenance of pluripotency of ES cells are suggested, and it can be confirmed whether or not each candidate gene can induce nuclear reprogramming alone or in an appropriate combination thereof. For example, a combination of all of the selected primary candidate genes is confirmed to be capable of inducing the reprogramming of differentiated cells into a state close to that of ES cells. Combinations are then prepared by withdrawing each individual gene from the aforementioned combination, and the same actions of the combinations are confirmed in order to select each secondary candidate gene whose absence causes a reduction of the reprogramming induction ability or loss of the reprogramming induction ability. By repeating similar steps for the secondary candidate genes selected as described above, an essential combination of nuclear reprogramming genes can be selected, and it can be confirmed that a combination of gene products of each of the three kinds of genes, an Oct family gene, a Klf family gene, and a Myc family gene, acts as a nuclear reprogramming factor. It can be further confirmed that a combination of a gene product of a Sox family gene additionally with the gene products of the aforementioned three kinds of genes has extremely superior characteristics as a nuclear reprogramming factor. Specific examples of the selection method for the nuclear reprogramming factors are demonstrated in the examples of the specification. Therefore, by referring to the above general explanations and specific explanations of the examples, those skilled in the art can readily confirm that the combination of these three kinds of genes induces the reprogramming of somatic cells, and that the combination of these three kinds of gene products is essential for nuclear reprogramming.

The nuclear reprogramming factor provided by the present invention comprises at least a combination of gene products of an Oct family gene, a Klf family gene, and a Myc family gene, for example, a combination of gene products of Oct3/4, Klf4, and c-Myc. Examples of the Oct family gene include, for example, Oct3/4, Oct1A, Oct6, and the like. Oct3/4 is a transcription factor belonging to the POU family, and is reported as a marker of undifferentiated cells (K. Okamoto et al., Cell, 60, pp 461-72, 1990). Oct3/4 is also reported to participate in the maintenance of pluripotency (J. Nichols et al., Cell, 95, pp 379-91, 1998). Examples of the Klf family gene include Klf1, Klf2, Klf4, Klf5 and the like. Klf4 (Kruppel like factor-4) is reported as a tumor repressing factor (A. M. Ghaleb et al., Cell Res., 15, pp 92-6, 2005). Examples of the Myc family gene include c-Myc, N-Myc, L-Myc and the like. c-Myc is a transcription control factor involved in differentiation and proliferation of cells (S. Adhikary, M. Eilers, Nat. Rev. Mol. Cell Biol., 6, pp. 635-45, 2005), and is also reported to be involved in the maintenance of pluripotency (P. Cartwright et al., Development, 132, pp. 885-96, 2005). The NCBI accession numbers of the genes of the families other than Oct3/4, Klf4 and c-Myc are as follows:

TABLE 1

|       |                                                                             | Mouse      | Human      |
|-------|-----------------------------------------------------------------------------|------------|------------|
| Klf1  | Kruppel-like factor 1 (erythroid)                                           | NM_010635  | NM_006563  |
| Klf2  | Kruppel-like factor 2 (lung)                                                | NM_008452  | NM_016270  |
| Klf5  | Kruppel-like factor 5                                                       | NM_009769  | NM_001730  |
| c-Myc | myelocytomatosis oncogene                                                   | NM_010849  | NM_002467  |
| N-Myc | v-Myc myelocytomatosis viral related oncogene, neuroblastoma derived (avian) | NM_008709  | NM_005378  |
| L-Myc | v-Myc myelocytomatosis viral oncogene homolog 1, lung carcinoma derived (avian) | NM_008506 | NM_005376 |
| Oct1A | POU domain, class 2, transcription factor 1                                 | NM_198934  | NM_002697  |
| Oct6  | POU domain, class 3, transcription factor 1                                 | NM_011141  | NM_002699  |

All of these genes are those commonly existing in mammals including human, and for use of the aforementioned gene products in the present invention, genes derived from arbitrary mammals (those derived from mammals such as mouse, rat, bovine, ovine, horse, and ape) can be used. In addition to wild-type gene products, mutant gene products including substitution, insertion, and/or deletion of several (for example, 1 to 10, preferably 1 to 6, more preferably 1 to 4, still more preferably 1 to 3, and most preferably 1 or 2) amino acids and having similar function to that of the wild-type gene products can also be used. For example, as a gene product of c-Myc, a stable type product (T58A) may be used as well as the wild-type product. The above explanation may be applied similarly to the other gene products.

The nuclear reprogramming factor of the present invention may comprise a gene product other than the aforementioned three kinds of gene products. An example of such gene product includes a gene product of a Sox family gene. Examples of the Sox family gene include, for example, Sox1, Sox3, Sox7, Sox15, Sox17 and Sox18, and a preferred example includes Sox2. A nuclear reprogramming factor comprising at least a combination of the gene products of four kinds of genes, an Oct family gene (for example, Oct3/4), a Klf family gene (for example, Klf4), a Myc family gene (for example, c-Myc), and a Sox family gene (for example, Sox2) is a preferred embodiment of the present invention from a viewpoint of reprogramming efficiency, and in particular, a combination of a gene product of a Sox family gene is sometimes preferred to obtain pluripotency. Sox2, expressed in an early development process, is a gene encoding a transcription factor (A. A. Avilion et al., Genes Dev., 17, pp. 126-40, 2003). The NCBI accession numbers of Sox family genes other than Sox2 are as follows.

TABLE 2

|       |                          | Mouse      | Human      |
|-------|--------------------------|------------|------------|
| Sox1  | SRY-box containing gene 1  | NM_009233  | NM_005986  |
| Sox3  | SRY-box containing gene 3  | NM_009237  | NM_005634  |
| Sox7  | SRY-box containing gene 7  | NM_011446  | NM_031439  |
| Sox15 | SRY-box containing gene 15 | NM_009235  | NM_006942  |
| Sox17 | SRY-box containing gene 17 | NM_011441  | NM_022454  |
| Sox18 | SRY-box containing gene 18 | NM_009236  | NM_018419  |

Further, a gene product of a Myc family gene may be replaced with a cytokine. As the cytokine, for example, SCF, bFGF or the like is preferred. However, cytokines are not limited to these examples.

As a more preferred embodiment, an example includes a factor which induces immortalization of cells, in addition to the aforementioned three kinds of gene products, preferably, the four kinds of gene products. For example, an example includes a combination of a factor comprising a gene product of TERT gene with a factor comprising a gene product or gene products of one or more kinds of genes selected from the group consisting of the following genes: SV40 Large T antigen, HPV16 E6, HPV16 E7, and Bmil. TERT is essential for the maintenance of the telomere structure at the end of chromosome at the time of DNA replication, and the gene is expressed in stem cells or tumor cells in humans, whilst it is not expressed in many somatic cells (I. Horikawa, et al., Proc. Natl. Acad. Sci. USA, 102, pp. 18437-442, 2005). SV40 Large T antigen, HPV16 E6, HPV16 E7, or Bmil was reported to induce immortalization of human somatic cells in combination with Large T antigen (S. Akimov et al., Stem Cells, 23, pp. 1423-1433, 2005; P. Salmon et al., Mol. Ther., 2, pp. 404-414, 2000). These factors are extremely useful particularly when iPS cells are induced from human cells. The NCBI accession numbers of TERT and Bmil genes are as follows.

TABLE 3

|  |  | Mouse | Human |
|---|---|---|---|
| TERT | telomerase reverse transcriptase | NM_009354 | NM_198253 |
| Bmi1 | B lymphoma Mo-MLV insertion region 1 | NM_007552 | NM_005180 |

Furthermore, a gene product or gene products of one or more kinds of genes selected from the group consisting of the following: Fbx15, Nanog, ERas, ECAT15-2, Tcl1, and β-catenin may be combined. As a particularly preferred embodiment from a viewpoint of reprogramming efficiency, an example includes a nuclear reprogramming factor comprising a total of ten kinds of gene products, wherein gene products of Fbx15, Nanog, ERas, ECAT15-2, Tcl1, and β-catenin are combined with the aforementioned four kinds of gene products. Fbx15 (Y. Tokuzawa et al., Mol. Cell Biol., 23, pp. 2699-708, 2003), Nanog (K. Mitsui et al., Cell, 113, pp. 631-42, 2003), ERas (K. Takahashi, K. Mitsui, S. Yamanaka, Nature, 423, pp. 541-5, 2003), and ECAT15-2 (A. Bortvin et al., Development, 130, pp. 1673-80, 2003) are genes specifically expressed in ES cells. Tcl1 is involved in the activation of Akt (A. Bortvin et al., Development, 130, pp. 1673-80, 2003), and β-catenin is an important factor constituting the Wnt signal transmission pathway, and also reported to be involved in the maintenance of pluripotency (N. Sato et al, Nat. Med., 10, pp. 55-63, 2004).

Further, the nuclear reprogramming factor of the present invention may comprise, for example, a gene product or gene products of one or more kinds of genes selected from the group consisting of the following: ECAT1, Esg1, Dnmt3L, ECAT8, Gdf3, Sox15, ECAT15-1, Fthl17, Sall4, Rex1, UTF1, Stella, Stat3, and Grb2. ECAT1, Esg1, ECAT8, Gdf3, and ECAT15-1 are genes specifically expressed in ES cells (K. Mitsui et al., Cell, 113, pp. 631-42, 2003). Dnmt3L is a DNA methylating enzyme-related factor, and Sox15 is a class of genes expressed in an early development process and encoding transcription factors (M. Maruyama et al., J. Biol. Chem., 280, pp. 24371-9, 2005). Fthl17 encodes ferritin heavy polypeptide-like 17 (A. colLoriot, T. Boon, C. De Smet, Int. J. Cancer, 105, pp. 371-6, 2003), Sall4 encodes a Zn finger protein abundantly expressed in embryonic stem cells (J. Kohlhase et al., Cytogenet. Genome Res., 98, pp. 274-7, 2002), and Rex1 encodes a transcription factor locating downstream from Oct¾ (E. Ben-Shushan, J. R. Thompson, L. J. Gudas, Y. Bergman, Mol. Cell Biol., 18, pp. 1866-78, 1998). UTF1 is a transcription cofactor locating downstream from Oct¾, and it is reported that the suppression of the proliferation of ES cells is induced when this factor is suppressed (A. Okuda et al., EMBO J., 17, pp. 2019-32, 1998). Stat3 is a signal factor for proliferation and differentiation of cells. The activation of Stat3 triggers the operation of LIF, and thereby the factor plays an important role for the maintenance of pluripotency (H. Niwa, T. Burdon, I. Chambers, A. Smith, Genes Dev., 12, pp. 2048-60, 1998). Grb2 encodes a protein mediating between various growth factor receptors existing in cell membranes and the Ras/MAPK cascade (A. M. Cheng et al., Cell, 95, pp. 793-803, 1998).

However, the gene products which may be included in the nuclear reprogramming factor of the present invention are not limited to the gene products of the genes specifically explained above. The nuclear reprogramming factor of the present invention may contain one or more factors relating to differentiation, development, proliferation or the like and factors having other physiological activities, as well as other gene products which can function as a nuclear reprogramming factor. It is understood that such embodiments fall within the scope of the present invention. By using somatic cells in which only one or two genes among the three kinds of the gene Oct¾, Klf4, and c-Myc are expressed, the other gene products which can function as a nuclear reprogramming factor can be identified by, for example, performing screening for a gene product which can induce nuclear reprogramming of said cells. According to the present invention, the aforementioned screening method is also provided as a novel method for screening for a nuclear reprogramming factor.

The gene products contained in the nuclear reprogramming factor of the present invention may be, for example, a protein, per se, produced from the aforementioned gene, or alternatively, in a form of a fusion gene product of said protein with another protein, peptide or the like. For example, a fusion protein with green fluorescence protein (GFP) or a fusion gene product with a peptide such as a histidine tag can also be used. Further, by preparing and using a fusion protein with the TAT peptide derived form the virus HIV, intracellular uptake of the nuclear reprogramming factor through cell membranes can be promoted, thereby enabling induction of reprogramming only by adding the fusion protein to a medium thus avoiding complicated operations such as gene transduction. Since preparation methods of such fusion gene products are well known to those skilled in the art, skilled artisans can easily design and prepare an appropriate fusion gene product depending on the purpose.

By using the nuclear reprogramming factor of the present invention, the nucleus of a somatic cell can be reprogrammed to obtain an induced pluripotent stem cell. In the specification, the term "induced pluripotent stem cells" means cells having properties similar to those of ES cells, and more specifically, the term encompasses undifferentiated cells having pluripotency and growth ability. However, the term should not be construed narrowly in any sense, and should be construed in the broadest sense. The method for preparing induced pluripotent stem cells by using a nuclear reprogramming factor is explained in International Publication WO2005/80598 (the term "ES-like cells" is used in the publication), and a means for isolating induced pluripotent stem cells is also specifically explained. Therefore, by referring to the aforementioned publication, those skilled in the art can easily prepare induced pluripotent stem cells by using the nuclear reprogramming factor of the present invention.

The method for preparing induced pluripotent stem cells from somatic cells by using the nuclear reprogramming factor of the present invention is not particularly limited. Any method may be employed as long as the nuclear reprogramming factor can contact with somatic cells under an environment in which the somatic cells and induced pluripotent stem cells can proliferate. For example, a gene product contained in the nuclear reprogramming factor of the present invention may be added to a medium. Alternatively, by using a vector containing a gene that is capable of expressing the nuclear reprogramming factor of the present invention, a means of transducing said gene into a somatic cell may be employed. When such vector is used, two or more kinds of genes may be incorporated into the vector, and each of the gene products may be simultaneously expressed in a somatic cell. When one or more of the gene products contained in the nuclear reprogramming factor of the present invention are already expressed in a somatic cell to be reprogrammed, said gene products may be excluded from the nuclear reprogramming factor of the present invention. It is understood that such embodiment falls within the scope of the present invention.

In the preparation of induced pluripotent stem cells by using the nuclear reprogramming factor of the present invention, types of somatic cells to be reprogrammed are not particularly limited, and any kinds of somatic cells may be used. For example, matured somatic cells may be used, as well as somatic cells of an embryonic period. When induced pluripotent stem cells are used for therapeutic treatment of diseases, it is desirable to use somatic cells isolated from patients. For example, somatic cells involved in diseases, somatic cells participating in therapeutic treatment of diseases and the like can be used. A method for selecting induced pluripotent stem cells that appear in a medium according to the method of the present invention is not particularly limited, and a well-known means may be suitably employed, for example, a drug resistance gene or the like can be used as a marker gene to isolate induced pluripotent stem cells using drug resistance as an index. Various media that can maintain undifferentiated state and pluripotency of ES cells and various media which cannot maintain such properties are known in this field, and induced pluripotent stem cells can be efficiently isolated by using a combination of appropriate media. Differentiation and proliferation abilities of isolated induced pluripotent stem cells can be easily confirmed by those skilled in the art by using confirmation means widely applied to ES cells.

Uses of the induced pluripotent stem cells prepared by the method of the present invention are not particularly limited. The cells can be used for any experiments and research conducted with ES cells, therapeutic treatments utilizing ES cells and the like. For example, desired differentiated cells (e.g., nerve cells, cardiac muscle cells, hemocyte cells and the like) can be derived by treating induced pluripotent stem cells obtained by the method of the present invention with retinoic acid, growth factors such as EGF, glucocorticoid or the like, and stem cell therapy based on cellular auto-transplantation can be achieved by returning the differentiated cells obtained as described above to the patient. However, uses of the induced pluripotent stem cells of the present invention are not limited to the aforementioned specific embodiments.

EXAMPLES

The present invention will be more specifically explained with reference to examples. However, the scope of the present invention is not limited to the following examples.

Example 1

Selection of Reprogramming Factor

In order to identify reprogramming factors, an experimental system for easy observation of the reprogramming phenomenon is required. As an experimental system, a mouse in which βgeo (a fusion gene of β-galactosidase gene and neomycin resistance gene) was knocked into the Fbx15 locus was used. The mouse Fbx15 gene is a gene specifically expressed in differentiation pluripotent cells such as ES cells and early embryos. However, in a homomutant mouse in which βgeo was knocked into the mouse Fbx15 gene so as to delete the function of Fbx15, no abnormal phenotypes including those concerning differentiation pluripotency or development were observed. In this mouse, expression control of βgeo is attained by the enhancer and promoter of the Fbx15 gene. Specifically, βgeo is not expressed in differentiated somatic cells, and they have sensitivity to G418. In contrast, the βgeo knockin homomutant ES cells have resistance against G418 at an extremely high concentration (higher than 12 mg/ml). By utilizing the above phenomenon, an experimental system for visualizing the reprogramming of somatic cells was constructed.

In the aforementioned experimental system, fibroblasts (Fbx15$^{\beta geo/\beta geo}$ MEFs) were first isolated from an embryo of the βgeo knockin homomutant mouse (13.5 days after fertilization). Since MEFs do not express the Fbx15 gene, the cells also do not express βgeo and thus have sensitivity to G418. Whist, when the MEFs are fused with ES cells that have not been gene-manipulated (also having sensitivity to G418), the nuclei of MEFs are reprogrammed, and as a result, βgeo is expressed to give G418-resistance. The reprogramming phenomenon can thus be visualized as G418 resistance by using this experimental system (International Publication WO2005/80598). Searches for reprogramming factors were performed by using the aforementioned experimental system (FIG. 1), and total 24 kinds of genes were selected as candidate reprogramming factors, including genes showing specific expression in ES cells and genes suggested to have important roles in the maintenance of differentiation pluripotency of ES cells. These genes are shown in Tables 4 and 5 below. For β-catenin (#21) and c-Myc (#22), active type mutants (catenin: S33Y, c-Myc: T58A) were used.

TABLE 4

| Number | Name of Gene | Explanation of Gene |
|---|---|---|
| 1 | ECAT1 | ES cell associated transcript 1 (ECAT1) |
| 2 | ECAT2 | developmental pluripotency associated 5 (DPPA5), ES cell specific gene 1 (ESG1) |
| 3 | ECAT3 | F-box protein 15 (Fbx15), |
| 4 | ECAT4 | homeobox transcription factor Nanog |
| 5 | ECAT5 | ES cell expressed Ras (ERas), |
| 6 | ECAT7 | DNA (cytosine-5-)-methyltransferase 3-like (Dnmt3l), valiant 1 |
| 7 | ECAT8 | ES cell associated transcript 8 (ECAT8) |
| 8 | ECAT9 | growth differentiation factor 3 (Gdf3), |
| 9 | ECAT10 | SRY-box containing gene 15 (Sox15), |
| 10 | ECAT15-1 | developmental pluripotency associated 4 (Dppa4), variant 1 |

TABLE 4-continued

| Number | Name of Gene | Explanation of Gene |
|---|---|---|
| 11 | ECAT15-2 | developmental pluripotency associated 2 (Dppa2), |
| 12 | Fthl17 | ferritin, heavy polypeptide-like 17 (Fthl17), |
| 13 | Sall4 | sal-like 4 (*Drosophila*) (Sall4), transcript variant a |
| 14 | Oct3/4 | POU domain, class 5, transcription factor 1 (Pou5f1), |
| 15 | Sox2 | SRY-box containing gene 2 (Sox2), |
| 16 | Rex1 | zinc finger protein 42 (Zfp42), |
| 17 | Utf1 | undifferentiated embryonic cell transcription factor 1 (Utf1) |
| 18 | Tcl1 | T-cell lymphoma breakpoint 1 (Tcl1), |
| 19 | Stella | developmental pluripotency-associated 3 (Dppa3), |
| 20 | Klf4 | Kruppel-like factor 4 (gut) (Klf4), |
| 21 | β-catenin | catenin (cadherin associated protein), beta 1, 88 kDa (Ctnnb1) |
| 22 | c-Myc | myelocytomatosis oncogene (Myc), |
| 23 | Stat3 | signal transducer and activator of transcription 3 (Stat3), transcript variant 1 |
| 24 | Grb2 | growth factor receptor bound protein 2 (Grb2), |

TABLE 5

| Number | Name of Gene | Characteristic Feature | NCBI accession number Mouse | NCBI accession number Human |
|---|---|---|---|---|
| 1 | ECAT1 | Gene specifically expressed in ES cell | AB211060 | AB211062 |
| 2 | ECAT2 | Gene specifically expressed in ES cell | NM_025274 | NM_001025290 |
| 3 | ECAT3 | Gene specifically expressed in ES cell | NM_015798 | NM_152676 |
| 4 | ECAT4 | Transcription factor having homeodomain, essential factor for differentiation pluripotency maintenance | AB093574 | NM_024865 |
| 5 | ECAT5 | Ras family protein, ES cell growth promoting factor | NM_181548 | NM_181532 |
| 6 | ECAT7 | DNA methylation enzyme-related factor, essential for imprinting | NM_019448 | NM_013369 |
| 7 | ECAT8 | Gene specifically expressed in ES cell, having Tudor domain | AB211061 | AB211063 |
| 8 | ECAT9 | Gene specifically expressed in ES cell, belonging to TGFβ family | NM_008108 | NM_020634 |
| 9 | ECAT10 | Gene specifically expressed in ES cell, SRY family transcription factor | NM_009235 | NM_006942 |
| 10 | ECAT15-1 | Gene specifically expressed in ES cell | NM_028610 | NM_018189 |
| 11 | ECAT15-2 | Gene specifically expressed in ES cell | NM_028615 | NM_138815 |
| 12 | Fthl17 | Gene specifically expressed in ES cell, similar to ferritin heavy chain | NM_031261 | NM_031894 |
| 13 | Sall4 | Gene specifically expressed in ES cell, Zn finger protein | NM_175303 | NM_020436 |
| 14 | Oct3/4 | POU family transcription factor, essential for pluripotency maintenance | NM_013633 | NM_002701 |
| 15 | Sox2 | SRY family transcription factor, essential for pluripotency maintenance | NM_011443 | NM_003106 |
| 16 | Rex1 | Gene specifically expressed in ES cell, Zn finger protein | NM_009556 | NM_174900 |
| 17 | Utf1 | Transcription regulation factor highly expressed in ES cell, promoting growth of ES | NM_009482 | NM_003577 |
| 18 | Tcl1 | Oncogene activating AKT, abundantly expressed in ES cell | NM_009337 | NM_021966 |
| 19 | Stella | Gene specifically expressed in ES cell | NM_139218 | NM_199286 |
| 20 | Klf4 | Abundantly expressed in ES cell, both actions as antioncogene and oncogene are reported | NM_010637 | NM_004235 |
| 21 | β-catenin | Transcription factor activated by Wnt signal, involvement in pluripotency maintenance is reported | NM_007614 | NM_001904 |
| 22 | c-Myc | Transcription control factor participating in cell proliferation and differentiation and oncogene, | NM_010849 | NM_002467 |

TABLE 5-continued

Figure 2:
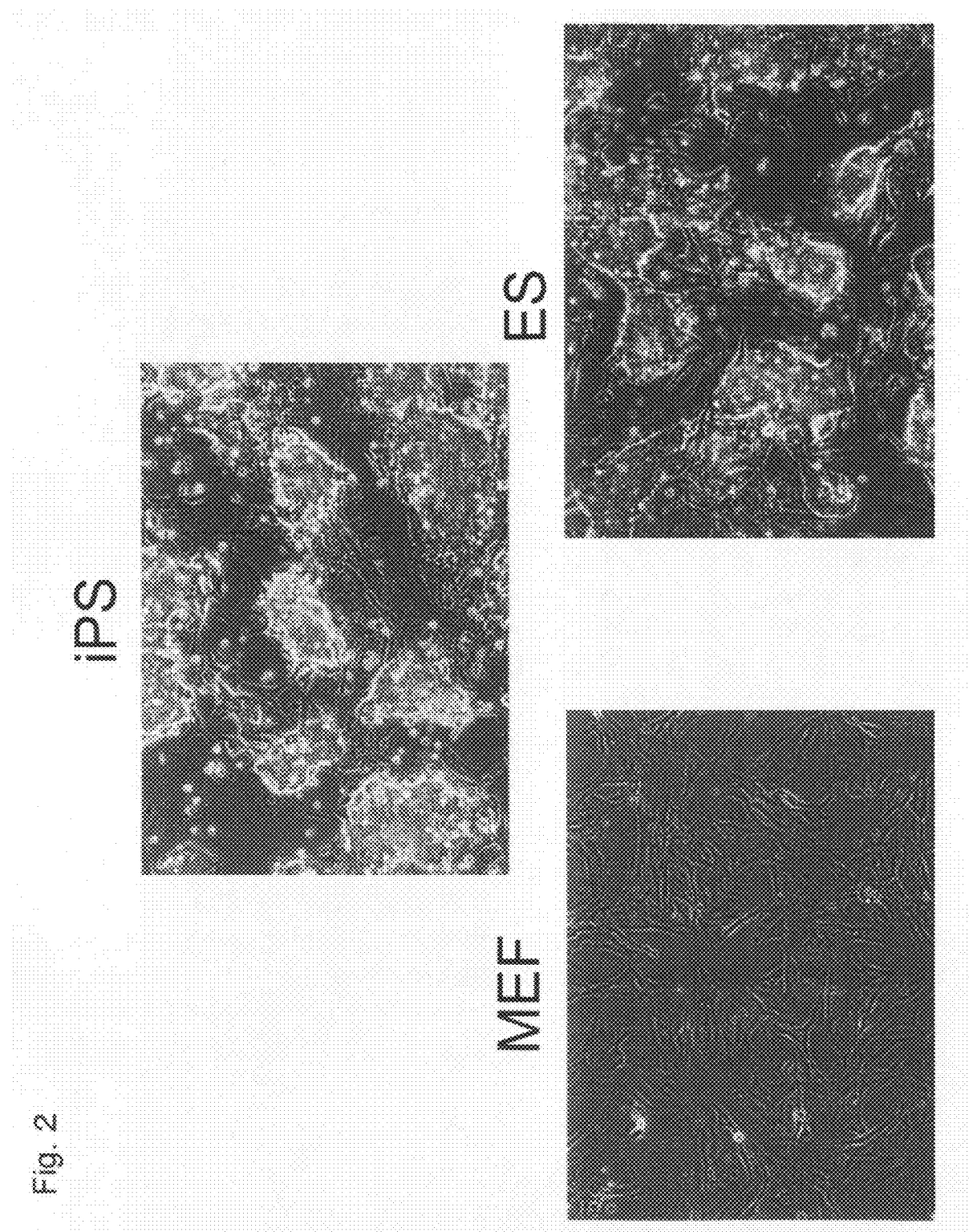
FIG. 2 depicts photographs showing morphology of iPS cells obtained by introducing the 24 genes shown in Table 1. Morphologies of differentiated cells (MEF) and of normal embryonic stem cells (ES) are also shown as a reference.

| Number | Name of Gene | Characteristic Feature | NCBI accession number Mouse | Human |
|---|---|---|---|---|
| 23 | Stat3 | involvement in pluripotency maintenance is reported Transcription factor activated by LIF signal, considered essential for pluripotency maintenance of mouse ES cells | NM_213659 | NM_139276 |
| 24 | Grb2 | Adapter protein mediating growth factor receptors and Ras/MAPK cascade | NM_008163 | NM_002086 | cDNAs of these genes were inserted into the retroviral vector pMX-gw by the Gateway technology. First, each of the 24 genes was infected into Fbx15$^{\beta geo/\beta geo}$ MEFs, and then G418 selection was performed under ES cell culture conditions. However, no G418-resistant colony was obtained. Next, the retroviral vectors of all of the 24 genes were simultaneously infected into Fbx15$^{\beta geo/\beta geo}$ MEFs. When G418 selection was performed under ES cell culture conditions, a plurality of drug resistant colonies were obtained. These colonies were isolated, and cultivation was continued. It was found that cultivation of these cells over a long period of time could be performed, and that these cells had morphology similar to that of ES cells (FIG. 2). In the figure, iPS cells represent induced pluripotent stem cells (also called "ES like cells", "ES-like cells", or "ESL cells"), ES represents embryonic stem cells, and MEF represents differentiated cells (embryonic fibroblasts).

Figure 3:
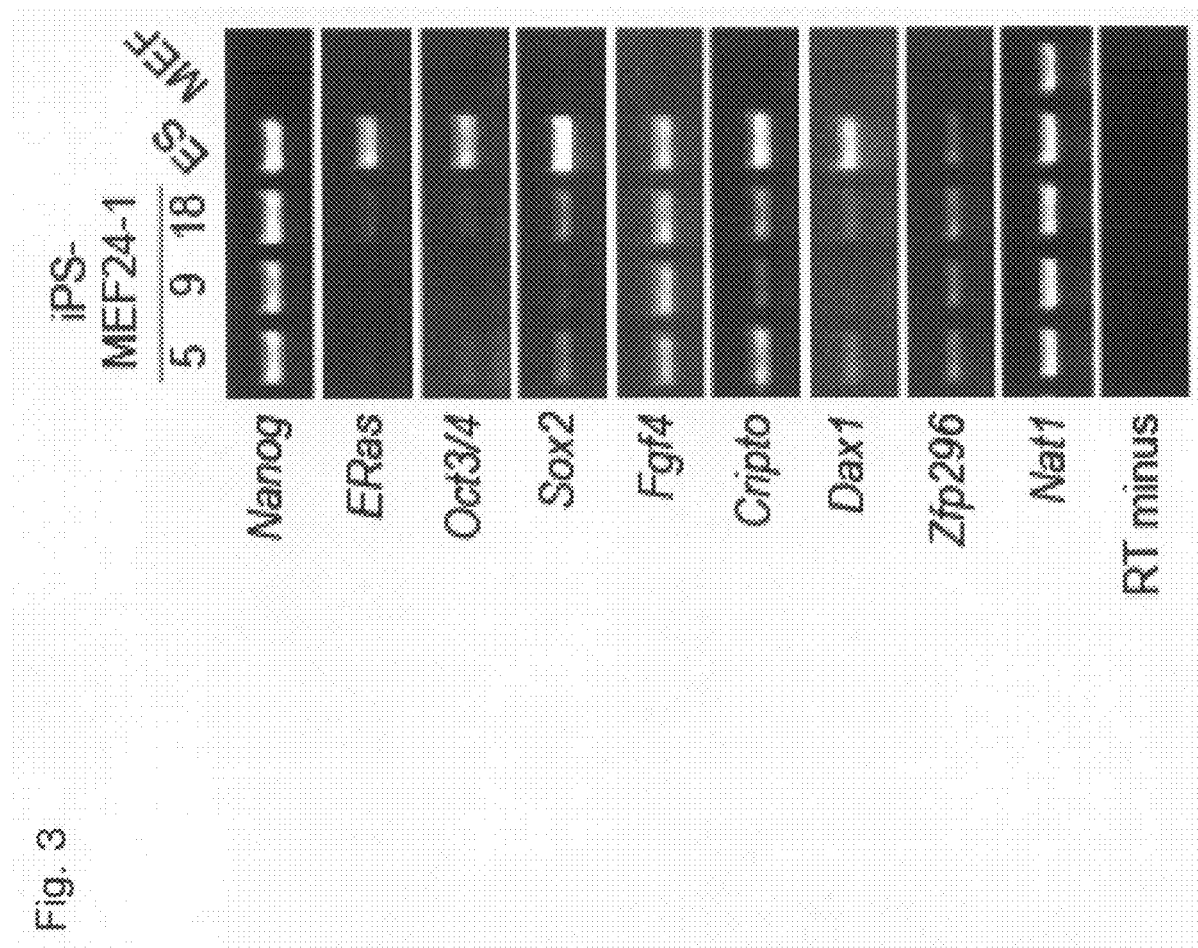
FIG. 3 shows expression profiles of marker genes in iPS cells. The results of RT-PCR using total RNAs extracted from iPS cells, ES cells and MEF cells as templates are shown.
Figure 4:
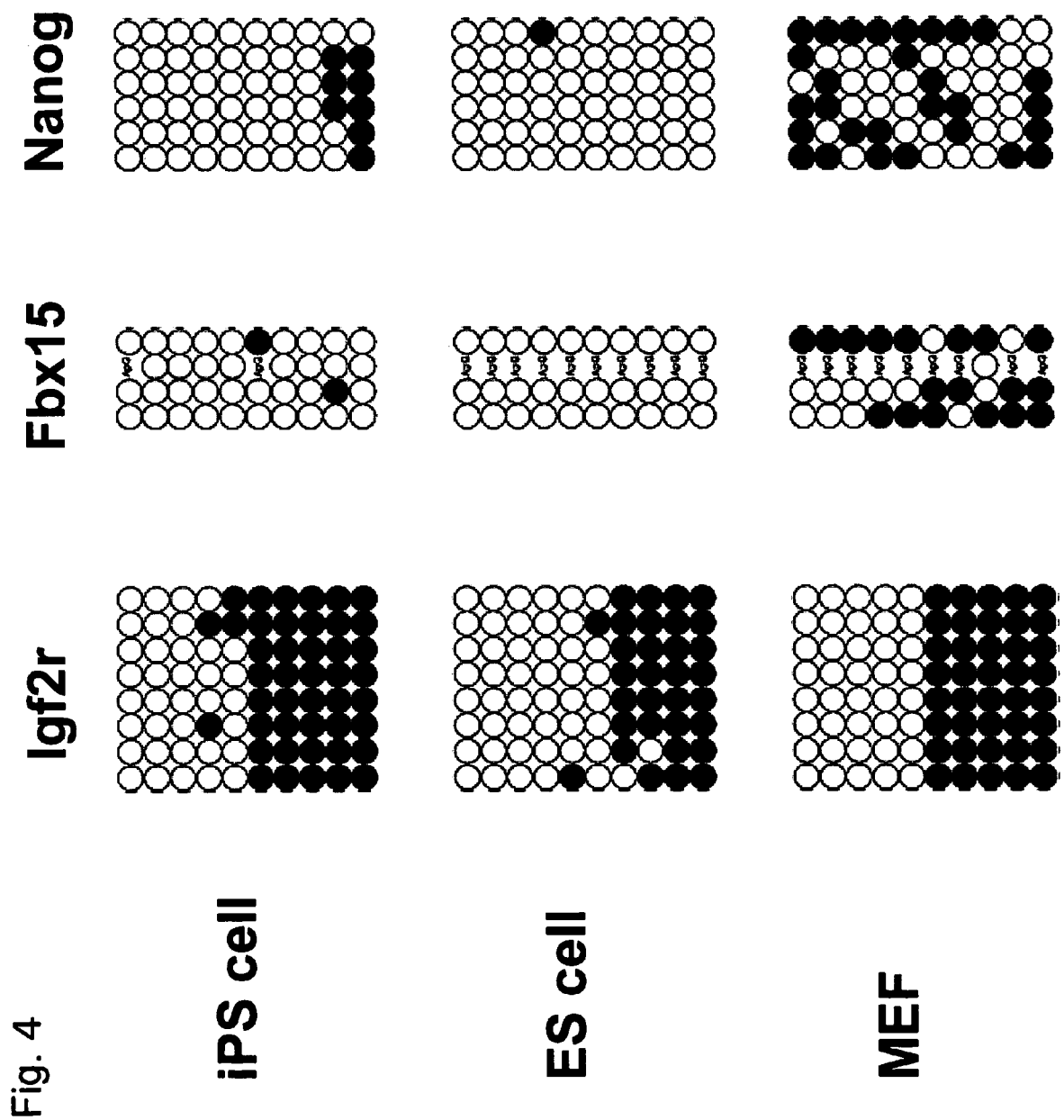
FIG. 4 shows methylation status of DNA in iPS cells. Genomic DNAs extracted from iPS cells, ES cells, and MEF cells were treated with bisulfite. The target DNAs were amplified by PCR and then inserted into plasmid. Ten clones of plasmid were isolated for each of the genes, and sequenced. Methylated CpGs are indicated with closed circles, and unmethylated CpGs with open circles.

When expression profiles of the marker genes were examined by RT-PCR, undifferentiation markers such as Nanog and Oct¾ were found to be expressed (FIG. 3). It was found that the expression of Nanog was close to that of ES cells, whereas the expression of Oct¾ was lower than that of ES cells. When DNA methylation status was examined by the bisulfite genomic sequencing, it was found that the Nanog gene and Fbx15 gene were highly methylated in MEFs, whereas they were demethylated in the iPS cells (FIG. 4). About 50% of IGF2 gene, an imprinting gene, was methylated both in the MEF and iPS cells. Since it was known that the imprinting memory was deleted and the IGF2 gene was almost completely demethylated in the primordial germ cells at 13.5 days after fertilization, from which the Fbx15$^{\beta geo/\beta geo}$ MEFs were isolated, it was concluded that iPS cells were not derived from primordial germ cells contaminated in the Fbx15$^{\beta geo/\beta geo}$ MEFs. The above results demonstrated that reprogramming of the differentiated cells (MEFs) into a state close to that of ES cells was able to be induced with the combination of the 24 kinds of factors.

Figure 5:
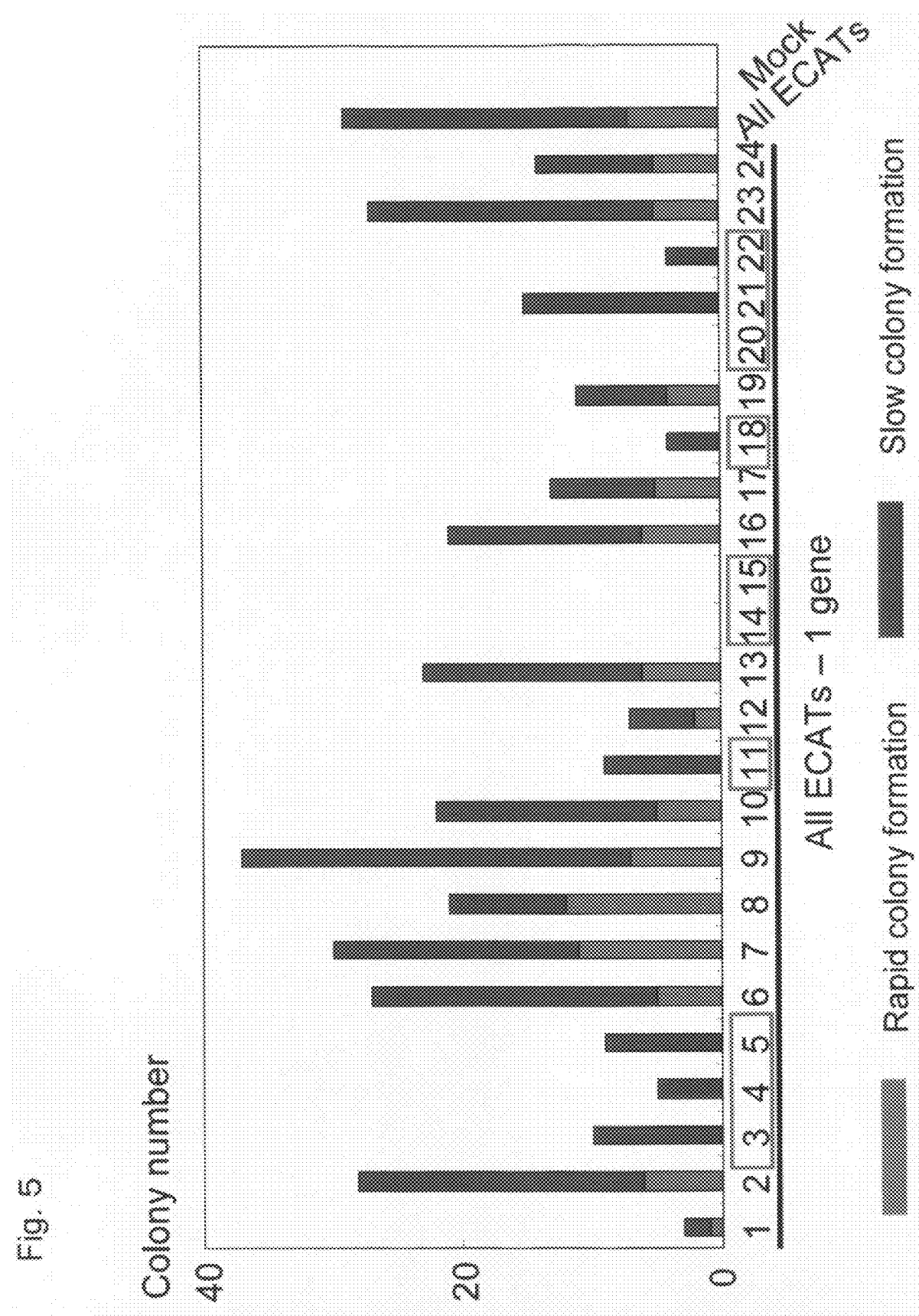
FIG. 5 shows colony numbers of G418 cells obtained by transduction of 24-gene group and 23-gene groups wherein each individual gene was withdrawn from the 24-gene group. The lower parts of the graph show colony numbers obtained in one week after the G418 selection, and the upper parts of the graph show numbers of clones obtained in three weeks. When each boxed gene (the reference number for each gene is the same as that indicated in Table 1) was withdrawn, no colonies were obtained at all, or only a few colonies were observed after 3 weeks.

Then, studies were made as to whether or not all of the 24 kinds of genes were required for the reprogramming. With withdrawal of each individual gene, 23 genes were transfected into the Fbx15$^{\beta geo/\beta geo}$ MEFs. As a result, for 10 genes, colony formation was found to be inhibited with each withdrawal thereof (FIG. 5, the gene numbers correspond to the gene numbers shown in Table 4, and the genes are the following 10 kinds of genes: #3, #4, #5, #11, #14, #15, #18, #20, #21, and #22). When these ten genes were simultaneously transfected into the Fbx15$^{\beta geo/\beta geo}$ MEFs, G418-resistant colonies were significantly more efficiently obtained as compared to simultaneous transfection with the 24 genes.

Figure 6:
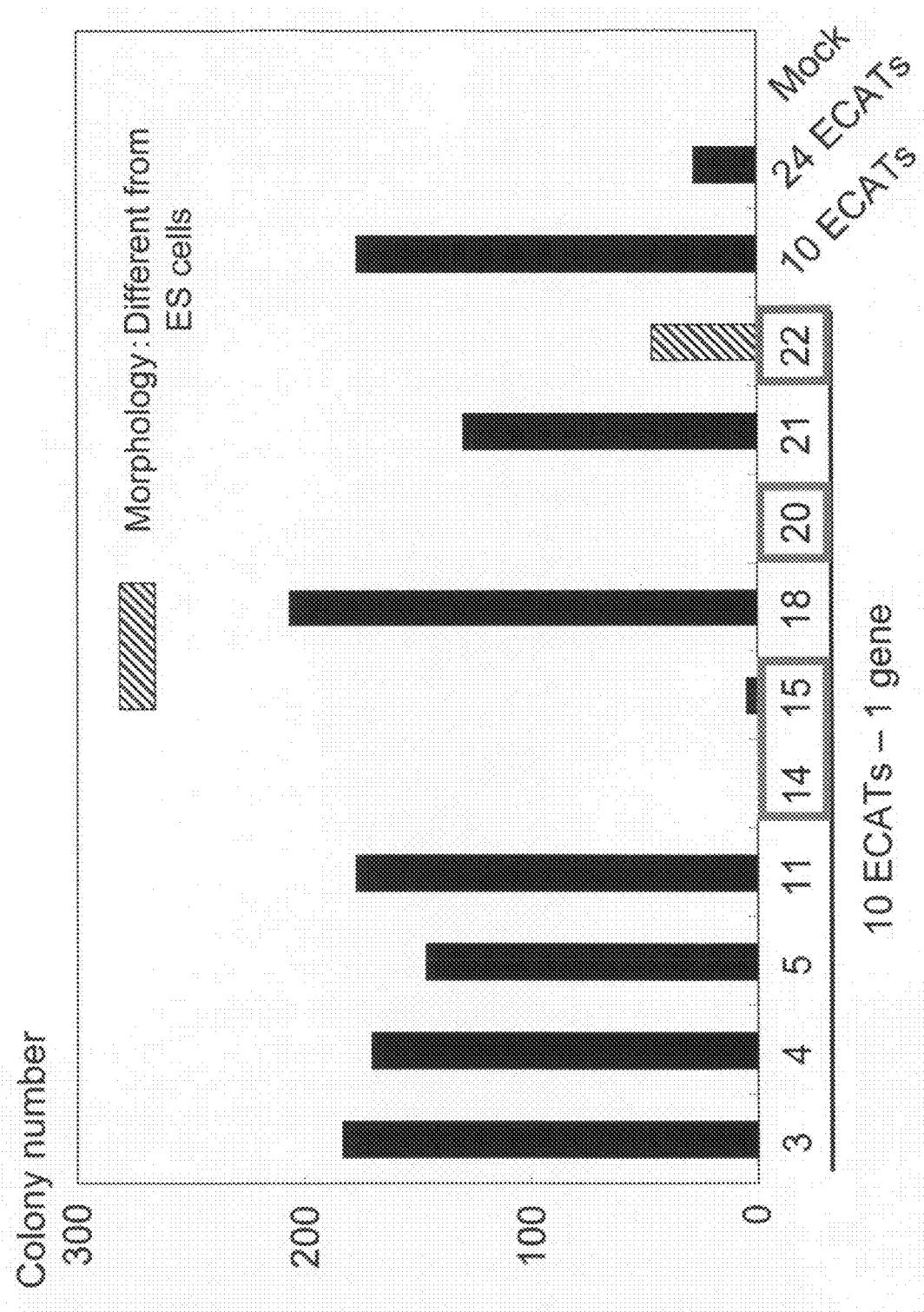
FIG. 6 shows colony numbers of G418 cells obtained by transduction of 10-gene group and 9-gene groups wherein each individual gene was withdrawn from the 10-gene group. When each of genes #14, #15 or #20 was withdrawn, no colony was obtained. When gene #22 was withdrawn, a few G418-resistant colonies were obtained. However, the cells gave differentiated morphology which was apparently different from that of iPS cells.

Furthermore, 9 genes, withdrawal of each individual gene from the 10 genes, were transfected into Fbx15$^{\beta geo/\beta geo}$ MEFs. As a result, it was found that G418-resistant iPS cell colonies were not formed when each of 4 kinds of genes (#14, #15, #20, or #22) was withdrawn (FIG. 6). Therefore, it was suggested that these four kinds of genes, among the ten genes, had particularly important roles in the induction of reprogramming.

Example 2

Induction of Reprogramming with Combination of 4 Kinds of Genes

It was examined whether or not induction of reprogramming of somatic cells was achievable with the four kinds of genes of which particular importance was suggested among the 10 genes. By using the combination of the aforementioned 10 kinds of genes, the combination of the aforementioned 4 kinds of genes, combinations of only 3 kinds of genes among the 4 kinds of genes, and combinations of only 2 kinds of genes among the 4 kinds of genes, these sets of genes were retrovirally transduced into the MEF cells as somatic cells in which βgeo was knocked into the Fbx15 gene. As a result, when the 4 kinds of genes were transduced, 160 G418-resistant colonies were obtained. Although this result was almost the same as that obtained by the transduction with the 10 kinds of genes (179 colonies), the colonies obtained by the 4-gene transduction were smaller than those by the 10-gene transduction. When these colonies were passaged, the numbers of colonies having iPS cell morphology was 9 clones among 12 clones in the case of the 10-gene transduction, whereas there was a somewhat lower tendency of 7 clones among 12 clones in the case of the 4-gene transduction. As for the 4 genes, almost the same numbers of iPS cells were obtained with either of those derived from mouse or those derived from human.

Figure 7:
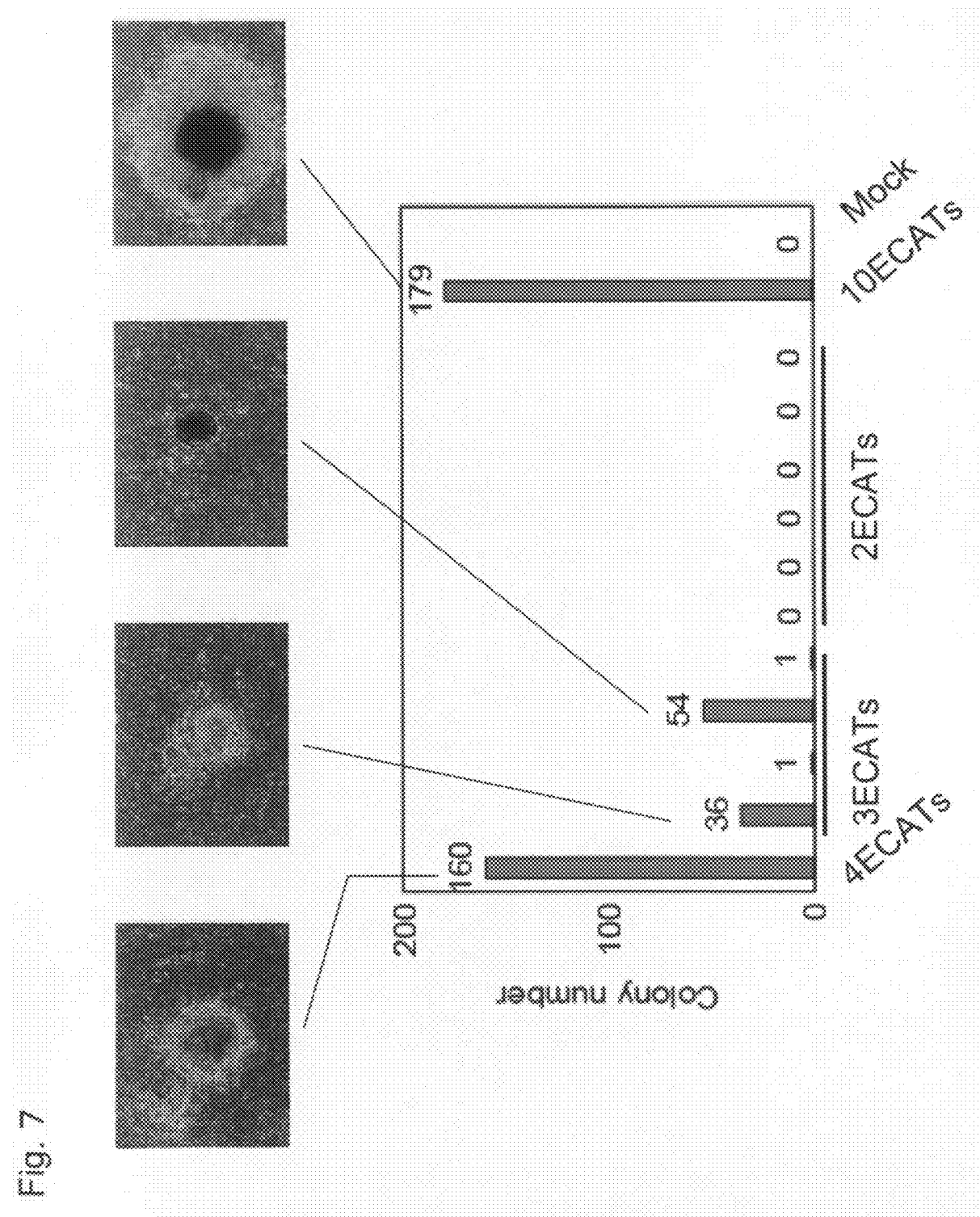
FIG. 7 shows numbers of G418-resistant emerged colonies (reprogrammed colony) with 10-gene group, 4-gene group, 3-gene groups, or 2-gene groups. Typical morphology and sizes of the colonies are shown.

When 3 genes selected from the aforementioned 4 genes were transduced, 36 flat colonies were obtained with one combination (#14, #15, and #20). However, iPS cells were not observed when they were passaged. With another combination (#14, #20, and #22), 54 small colonies were obtained. When 6 of the relatively large colonies from among those colonies were passaged, cells similar to ES cells were obtained for all these 6 clones. However, it seemed that adhesion of the cells between themselves and to the culture dish was weaker than that of ES cells. The proliferation rate of the cells was also slower than that observed in the case of the transduction with the 4 genes. Further, one colony each was formed with each of the other two kinds of combinations of 3 genes among the 4 genes. However, proliferation of the cells was not observed when the cells were passaged. With any of combinations of 2 genes selected from the 4 genes (6 combinations), no G418-resistant colonies were formed. The above results are shown in FIG. 7.

Figure 10:
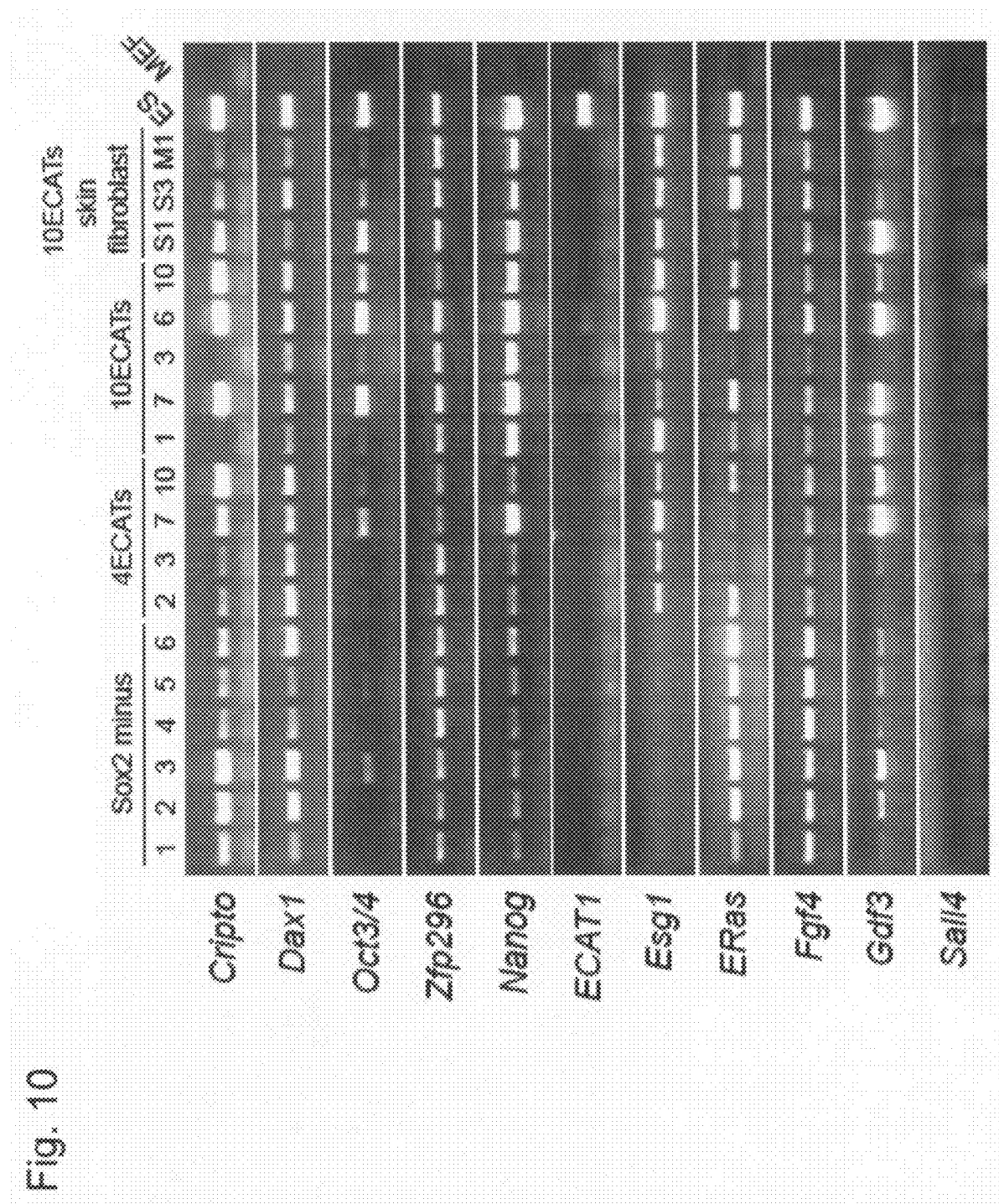
FIG. 10 depicts photographs showing results of RT-PCR confirming the expression of the ES cell marker genes. In the photographs, Sox2 minus indicates iPS cells established by the transduction of 3 genes into MEFs, 4ECATs indicates iPS cells established by the transduction of 4 genes into MEFs, 10ECATs indicates iPS cells established by the transduction of 10 genes into MEFs, 10ECATs Skin fibroblast indicates iPS cells established by the transduction of 10 genes into dermal fibroblasts, ES indicates mouse ES cells, and MEF indicates MEF cells without gene transduction. The numerical values under the symbols indicate clones numbers.

Further, the results of observation of expression profiles of the ES cell marker genes by RT-PCR are shown in FIG. 10. The details of the method are as follows. From iPS cells established by transducing 3 genes (Oct¾, Klf4, and c-Myc: represented as "Sox2 minus"), 4 genes (Sox2 was added to the three genes: represented as "4ECAT"), and 10 genes (#3, #4, #5, #11, #18, and #21 in Table 4 were added to the four genes: represented as "10ECAT") into Fbx15$^{\beta geo/\beta geo}$MEFs, iPS cells established by transducing 10 genes into fibroblasts established from tail tip of an adult mouse in which βgeo was knocked into the Fbx15 gene (represented as "10ECAT Skin fibroblast"), mouse ES cells, and MEF cells with no gene transduction, total RNAs were purified, and treated with DNaseI to remove contamination of genomic DNA. First strand cDNAs were prepared by a reverse transcription reaction, and expression profiles of the ES cell marker genes were examined by PCR. For Oct¾, Nanog, and ERas, PCR was performed by using primers which only amplified a transcript product from an endogenous gene, not from the transduced retrovirus. The primer sequences are shown in Table 6.

Example 3

Analysis of Pluripotency of Reprogrammed Cells

Figure 8:
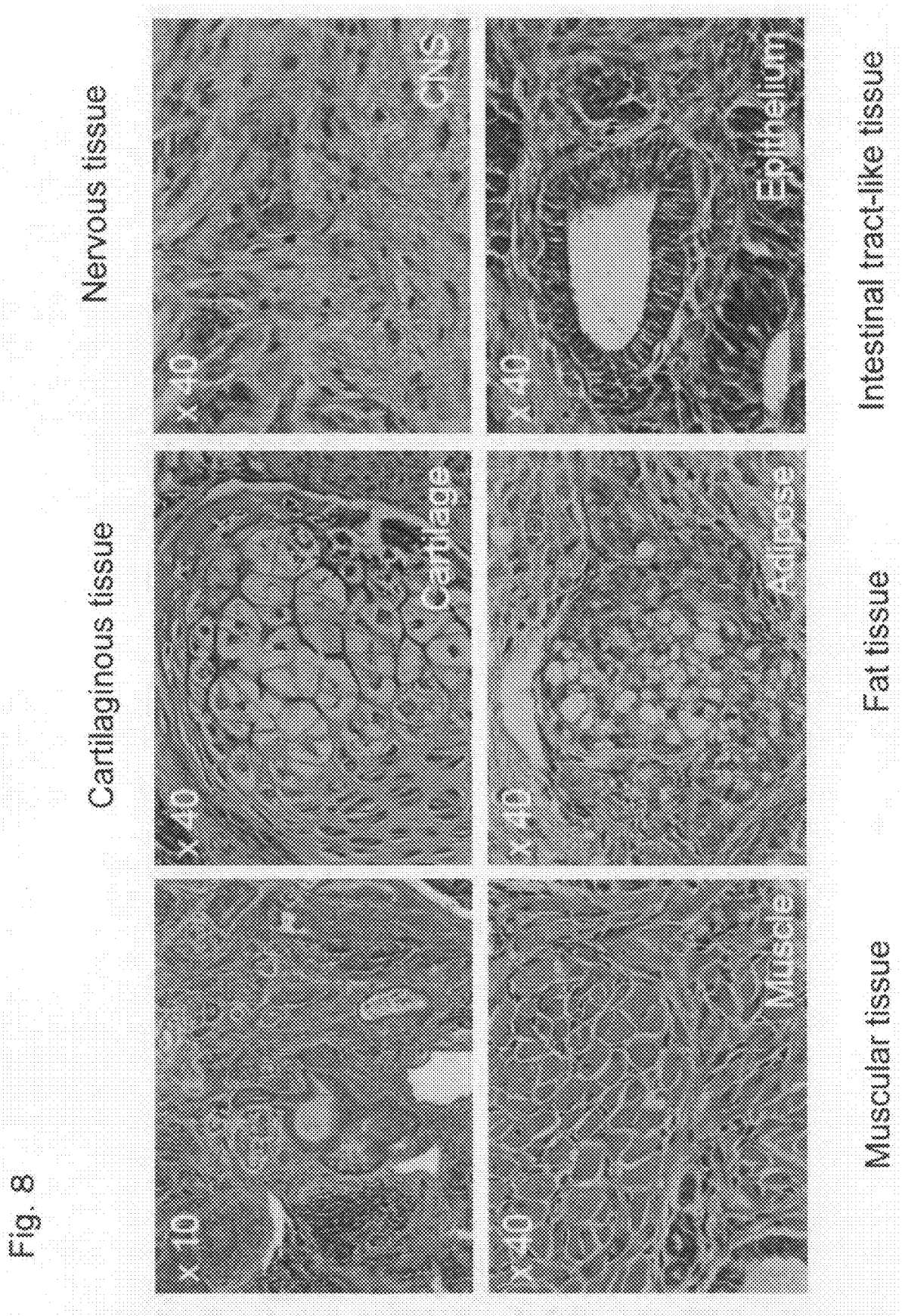
FIG. 8 depicts photographs showing results of hematoxylin-eosin (H & E) staining of tumors formed after subcutaneous transplantation of iPS cells derived from MEFs into nude mice. Differentiation into a variety of tissues in a triploblastic system was observed.

In order to evaluate the differentiation pluripotency of the established iPS cells, the iPS cells established with 24 factors, 10 factors, and 4 factors were subcutaneously transplanted into nude mice. As a result, tumors having a size similar to that observed with ES cells were formed in all animals. Histologically, the tumors consisted of a plurality of kinds of cells, and cartilaginous tissues, nervous tissues, muscular tissues, fat tissues, and intestinal tract-like tissues were observed (FIG. 8), which verified pluripotency of the iPS cells. In contrast, although tumors were formed when the cells established with the 3 factors were transplanted into nude mice, they were formed histologically only from undifferentiated cells. Therefore, it was found that a Sox family gene was essential for the induction of differentiation pluripotency.

TABLE 6

| Gene | Primer | Sequence | SEQ ID |
|---|---|---|---|
| ECAT1 | ECAT1-RT-S | TGT GGG GCC CTG AAA GGC GAG CTG AGA T | (SEQ ID NO: 1) |
|  | ECAT1-RT-AS | ATG GGC CGC CAT ACG ACG ACG GTC AAC T | (SEQ ID NO: 2) |
| Esg1 | pH34-U38 | GAA GTC TGG TTC CTT GGC AGG ATG | (SEQ ID NO: 3) |
|  | pH34-L394 | ACT CGA TAC ACT GGC CTA GC | (SEQ ID NO: 4) |
| Nanog | 6047-S1 | CAG GTG TTT GAG GGT AGC TC | (SEQ ID NO: 5) |
|  | 6047-AS1 | CGG TTC ATC ATG GTA CAG TC | (SEQ ID NO: 6) |
| ERas | 45328-S118 | ACT GCC CCT CAT CAG ACT GCT ACT | (SEQ ID NO: 7) |
|  | ERas-AS304 | CAC TGC CTT GTA CTC GGG TAG CTG | (SEQ ID NO: 8) |
| Gdf3 | Gdf3-U253 | GTT CCA ACC TGT GCC TCG CGT CTT | (SEQ ID NO: 9) |
|  | GDF3 L16914 | AGC GAG GCA TGG AGA GAG CGG AGC AG | (SEQ ID NO: 10) |
| Fgf4 | Fgf4-RT-S | CGT GGT GAG CAT CTT CGG AGT GG | (SEQ ID NO: 11) |
|  | Fgf4-RT-AS | CCT TCT TGG TCC GCC CGT TCT TA | (SEQ ID NO: 12) |
| Cripto | Cripto-S | ATG GAC GCA ACT GTG AAC ATG ATG TTC GCA | (SEQ ID NO: 13) |
|  | Cripto-AS | CTT TGA GGT CCT GGT CCA TCA CGT GAC CAT | (SEQ ID NO: 14) |
| Zfp296 | Zfp296-S67 | CCA TTA GGG GCC ATC ATC GCT TTC | (SEQ ID NO: 15) |
|  | Zfp296-AS350 | CAC TGC TCA CTG GAG GGG GCT TGC | (SEQ ID NO: 16) |
| Dax1 | Dax1-S1096 | TGC TGC GGT CCA GGC CAT CAA GAG | (SEQ ID NO: 17) |
|  | Dax1-AS1305 | GGG CAC TGT TCA GTT CAG CGG ATC | (SEQ ID NO: 18) |
| Oct3/4 | Oct3/4-S9 | TCT TTC CAC CAG GCC CCC GGC TC | (SEQ ID NO: 19) |
|  | Oct3/4-AS210 | TGC GGG CGG ACA TGG GGA GAT CC | (SEQ ID NO: 20) |
| NAT1 | NAT1 U283 | ATT CTT CGT TGT CAA GCC GCC AAA GTG GAG | (SEQ ID NO: 21) |
|  | NAT1 L476 | AGT TGT TTG CTG CGG AGT TGT CAT CTC GTC | (SEQ ID NO: 22) |

The results shown in this figure revealed that, by transduction of the 3 genes, expression of each of ERas and Fgf4 was efficiently induced, but expression of each of Oct¾ and Nanog, essential factors for the maintenance of pluripotency, was not induced, or was very weak even when induced. However, when the 4 genes were transduced, there was one clone (#7) in which Oct¾ and Nanog were relatively strongly induced among 4 clones examined. Further, when the 10 genes were transduced, strong induction of each of Oct¾ and Nanog was observed in 3 clones among 5 clones examined.

These results revealed that a combination of at least 3 genes (#14, #20, and #22) was essential for reprogramming, and in the cases of the 4-gene group and 10-gene group including the 3 kinds of genes, the reprogramming efficiency was increased in proportion to the increasing number of genes.

Example 4

Reprogramming of Fibroblasts Derived from Tails of Adult Mice

Figure 9:
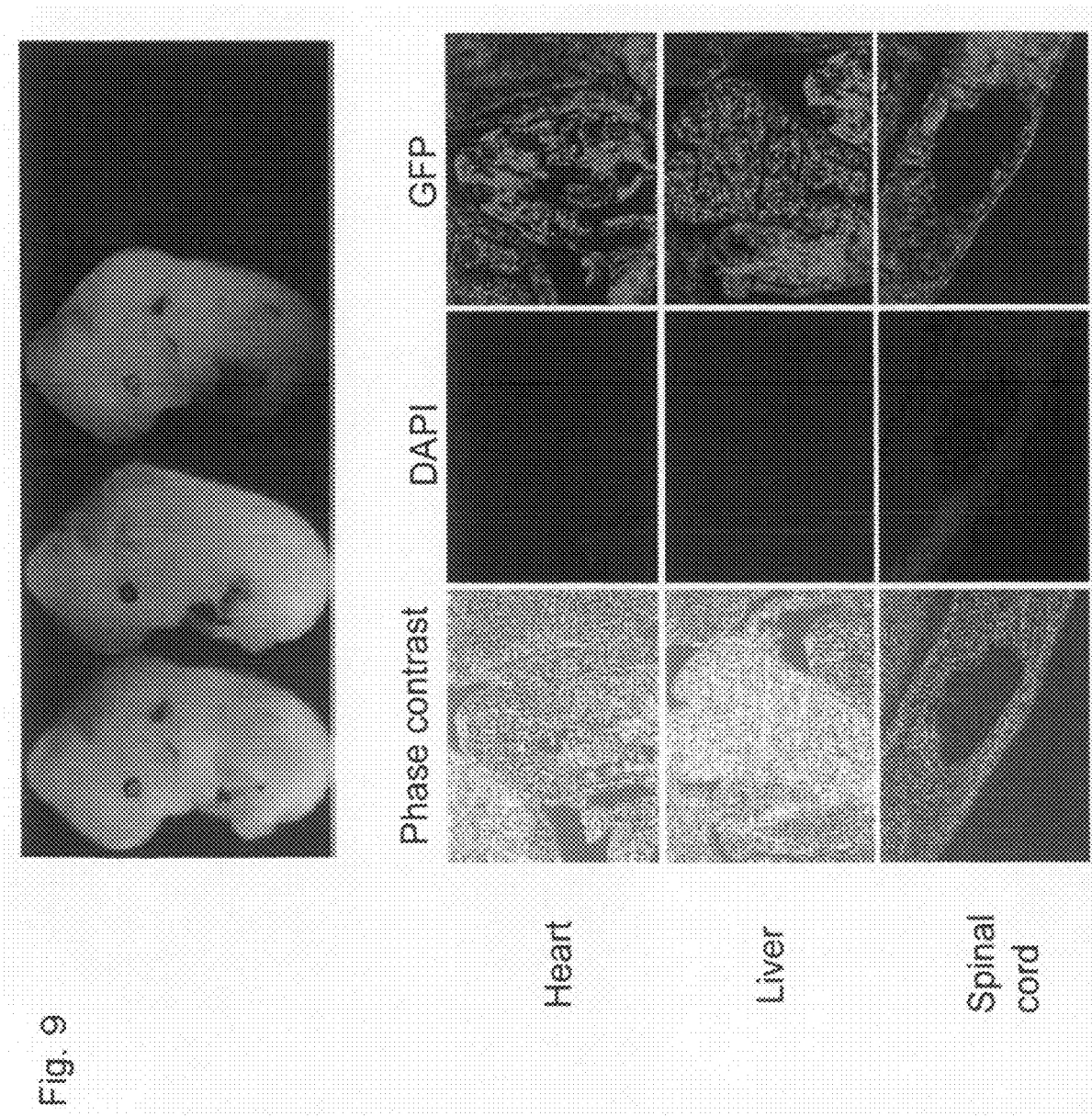
FIG. 9 depicts photographs of embryos prepared by transplanting iPS cells derived from adult dermal fibroblasts into mouse blastocysts and transplanting the cells into the uteri of pseudopregnant mice. It can be observed that, in the upper left embryo, cells derived from the iPS cells (emitting green fluorescence) were systemically distributed. In the lower photographs, it can be observed that almost all cells of the heart, liver, and spinal cord of the embryo were GFP-positive and were derived from the iPS cells.

The 4 factors identified in the mouse embryonic fibroblasts (MEFs) were transduced into fibroblasts derived from tails of βgeo knockin Fbx15 adult mice systemically expressing green fluorescence protein (GFP). Then, the cells were cultured on feeder cells under the same conditions as ES cell culture conditions, and G418 selection was performed. In about two weeks after the start of the drug selection, a plurality of colonies of iPS cells were obtained. When these cells were subcutaneously transplanted to nude mice, teratomas consisting of a variety of all three germ layer tissues were formed. Further, when the iPS cells derived from adult dermal fibroblasts were transplanted to the blastocysts, and then transplanted into the uteri of pseudopregnant mice, embryos in which the GFP-positive cells were systemically distributed were observed among those at 13.5 days after fertilization (FIG. 9), demonstrating that the iPS cells had pluripotency and were able to contribute to mouse embryogenesis. These results indicate that the identified class of factors had an ability to induce reprogramming of not only somatic cells in an embryonic period, but also somatic cells of mature mice. Practically, it is extremely important that the reprogramming can be induced in cells derived from adult skin.

Example 5

Figure 11:
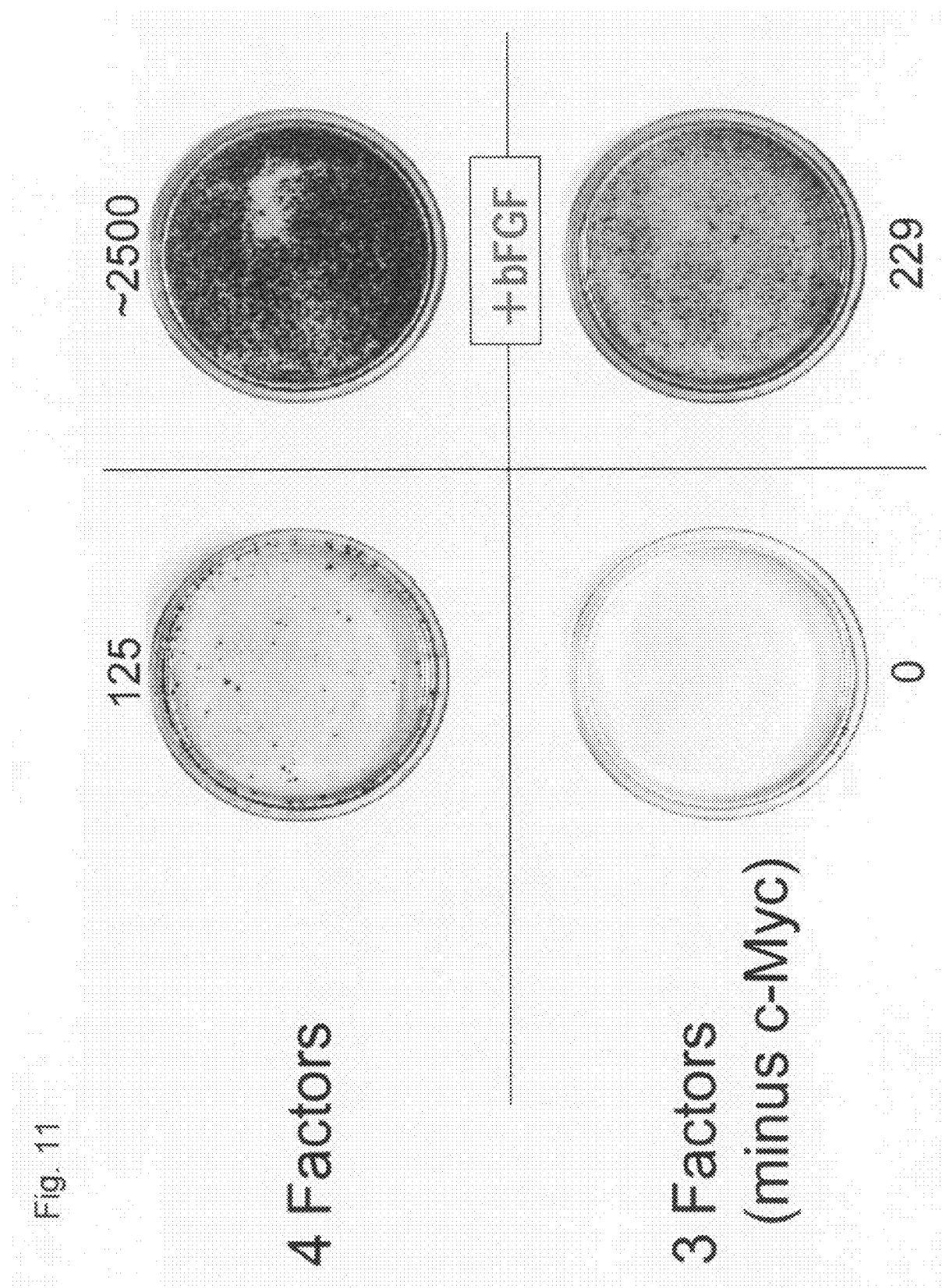
FIG. 11 shows an effect of bFGF on the establishment of iPS cells from MEFs. Four factors (upper row) or three factors except for c-Myc (lower row) were retrovirally transduced into MEFs derived from Fbx15$^{\beta geo/\beta geo}$ mice, and cultured on ordinary feeder cells (STO cells) (left) and bFGF expression vector-introduced STO cells (right). G418 selection was performed for 2 weeks, and cells were stained with crystal blue and photographed. The numerical values indicate the number of colonies.

An effect of cytokine on iPS cell establishment was investigated. Expression vector (pMX retroviral vector) for basic fibroblast growth factor (bFGF) or stem cell factor (SCF) was transduced into feeder cells (STO cells) to establish cells permanently expressing the cytokines. MEFs derived from the Fbx15$^{\beta geo/\beta geo}$ mouse (500,000 cells/100 mm dish) were cultured on these STO cells and transduced with the 4 factors, and then subjected to G418 selection. As a result, the number of formed colonies increased 20 times or higher on the STO cells producing bFGF (FIG. 11) or SCF (data not shown), as compared with the culture on normal STO cells. Further, although no iPS cell colony was formed on the normal STO cells when the 3 factors other than c-Myc were transduced, colony formation was observed on the STO cells producing bFGF (FIG. 11) or SCF (data not shown). These results revealed that stimulation with the cytokine increased the efficiency of the establishment of iPS cells from MEFs, and the nuclear reprogramming was achievable by using a cytokine instead of c-Myc.

Example 6

Family genes exist for all of the Oct3/4, Klf4, c-Myc, and Sox2 genes (Tables 1 and 2). Accordingly, studies were made as to whether iPS cells could be established with the family genes instead of the 4 genes. In Table 7, combined experimental results in duplicate are shown. With regard to the Sox family, Sox1 gave almost the same number of G418-resistant colonies formed and iPS cell establishment efficiency as those with Sox2. As for Sox3, the number of G418-resistant colonies formed was about 1/10 of that with Sox2, however, iPS cell establishment efficiency of the colonies picked up was in fact higher than that with Sox2. As for Sox15, both the number of G418-resistant colonies formed and iPS cell establishment efficiency were lower than those with Sox2. As for Sox17, the number of G418-resistant colonies formed was almost the same as that with Sox2, however, iPS cell establishment efficiency was low. With regard to the Klf family, Klf2 gave a smaller number of G418-resistant colonies than Klf4, however, they gave almost the same iPS cell establishment efficiency. With regard to the Myc family, it was found that wild-type c-Myc was almost the same as a T58A mutant both in the number of G418-resistant colonies formed and iPS cell establishment efficiency. Further, each of N-Myc and L-Myc (each wild type) was almost the same as c-Myc in both of the number of G418-resistant colonies formed and iPS cell establishment efficiency.

TABLE 7

| Transduced gene | Number of formed colonies | Number of picked colonies | Number of established iPS cell strain | iPS cell establishment efficiency (%) |
|---|---|---|---|---|
| 4 Factors (cMycT58A) | 85 | 12 | 5 | 42 |
| Sox1 | 84 | 12 | 7 | 58 |
| Sox3 | 8 | 8 | 7 | 92 |
| Sox15 | 11 | 11 | 1 | 8 |
| Sox17 | 78 | 12 | 2 | 17 |
| Klf2 | 11 | 10 | 5 | 50 |
| c-MycWT | 53 | 11 | 8 | 72 |
| N-MycWT | 40 | 12 | 7 | 58 |
| L-MycWT | 50 | 12 | 11 | 92 |
| 3 Factors (-Sox2) | 6 | 6 | 2 | 17 |

Example 7

Figure 12:
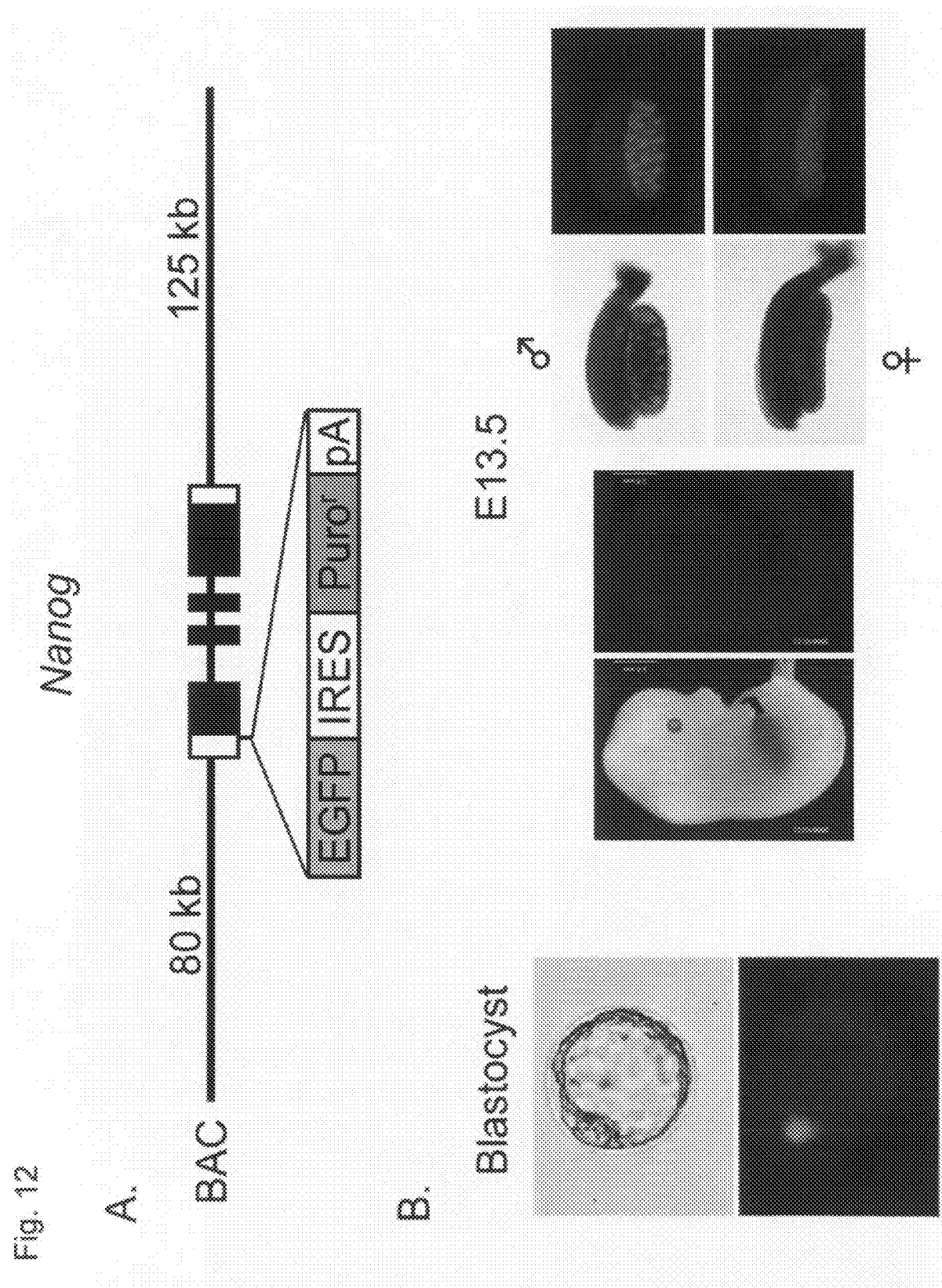
FIG. 12 depicts explanations of the experiments using Nanog-EGFP-IRES-Puro mice. A: E. coli artificial chromosome (BAC) containing the mouse Nanog gene in the center was isolated, and the EGFP-IRES-Puro cassette was inserted upstream from the coding region of Nanog by recombineering. B: Transgenic mice were prepared with the modified BAC. GFP expression was observed limitedly in inner cell masses of blastocysts and gonads.
Figure 13:
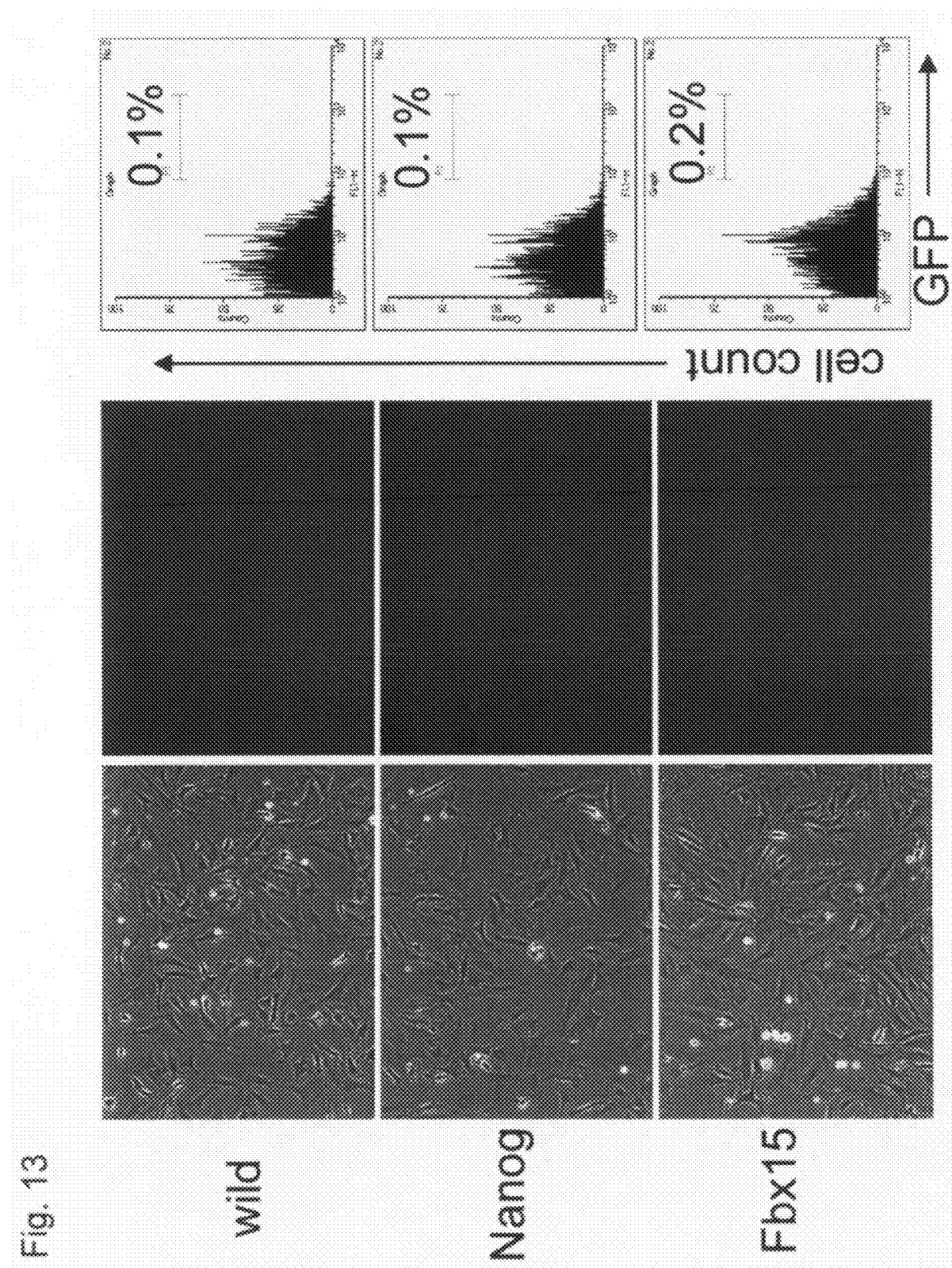
FIG. 13 depicts explanations of the experiments using Nanog-EGFP-IRES-Puro mice. From embryos of Nanog-EGFP-IRES-Puro mice (13.5 days after fertilization), heads, viscera and gonads were removed to establish MEFs. As a result of analysis with a cell sorter, almost no GFP-positive cells existed in MEFs derived from the Nanog-EGFP-IRES-Puro mice (Nanog) in the same manner as the Fbx15$^{\beta geo/\beta geo}$ mouse-derived MEFs (Fbx15) or wild-type mouse-derived MEFs (Wild).
Figure 14:
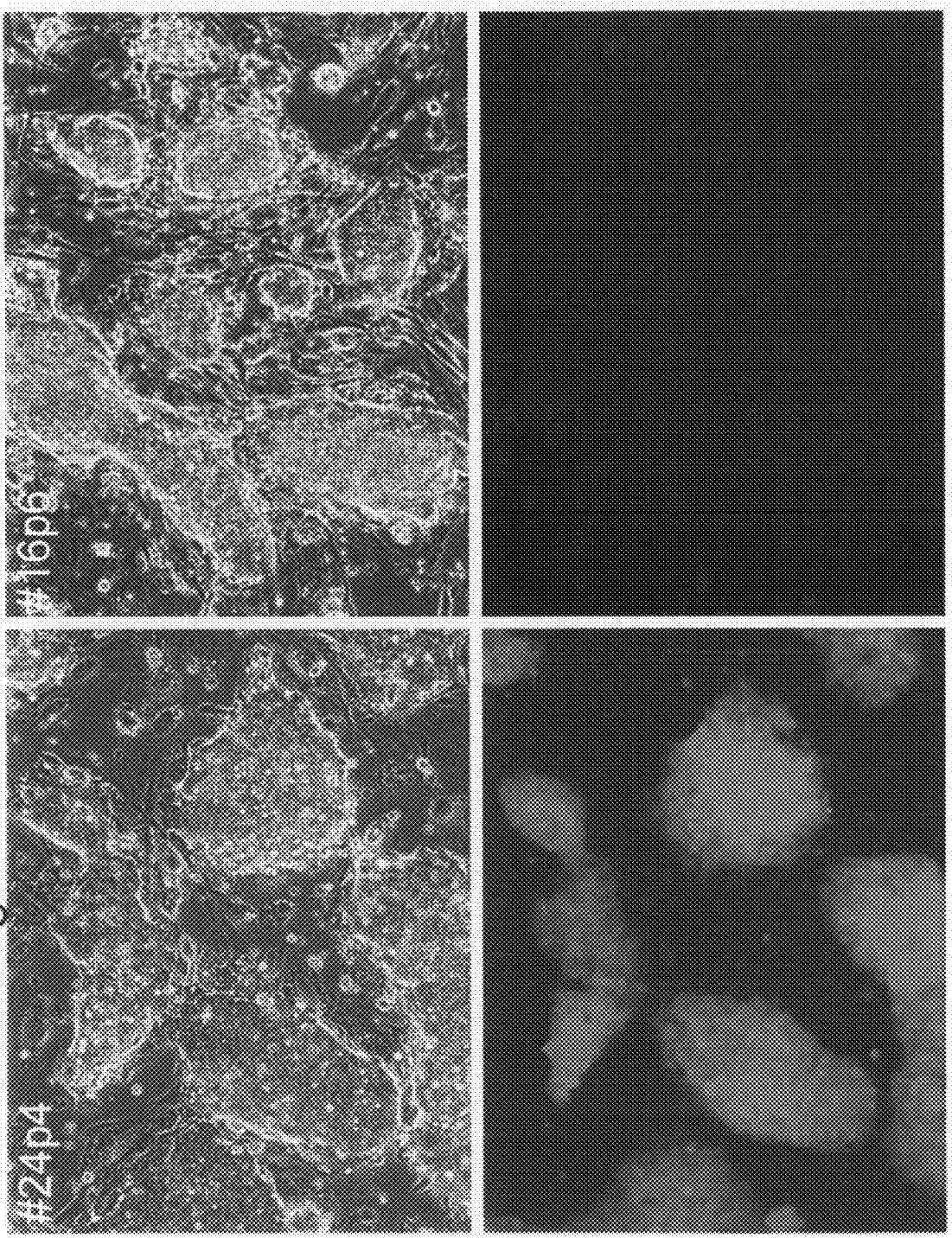
FIG. 14 depicts photographs of iPS cells established from the Nanog-EGFP-IRES-Puro mouse MEFs (left) and the Fbx15$^{\beta geo/\beta geo}$ mouse MEFs (right). The cells were selected with puromycin and G418, respectively.
Figure 15:
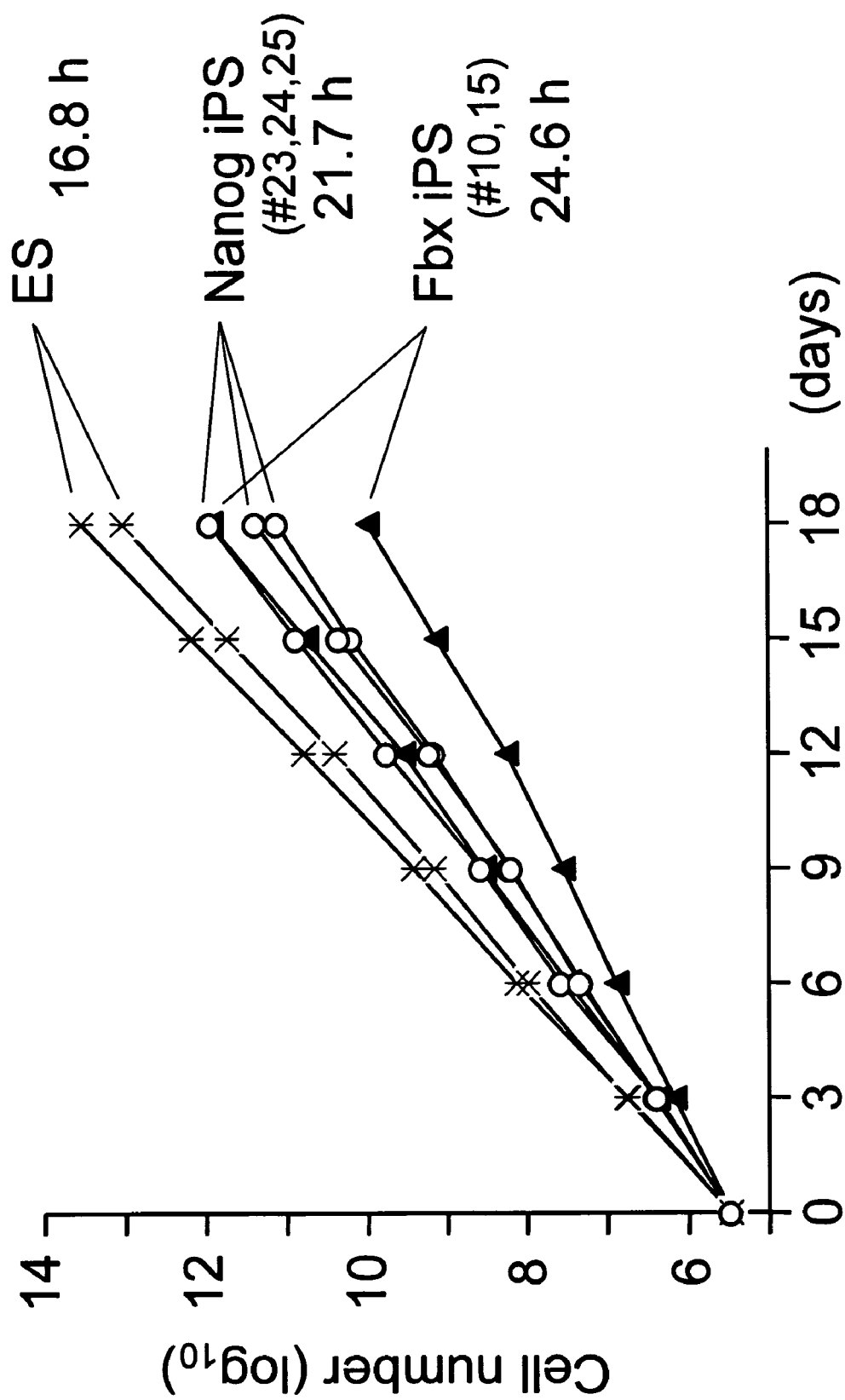
FIG. 15 shows results of growth of iPS cells. 100,000 cells of each of ES cells, iPS cells derived from the Nanog-EGFP-IRES-Puro mouse MEFs (Nanog iPS, left), and iPS cells derived from the Fbx15$^{\beta geo/\beta geo}$ mouse MEFs (Fbx iPS) were seeded on 24-well plates, and passaged every 3 days. Cell count results are shown. The numerical values represent average doubling times.
Figure 16:
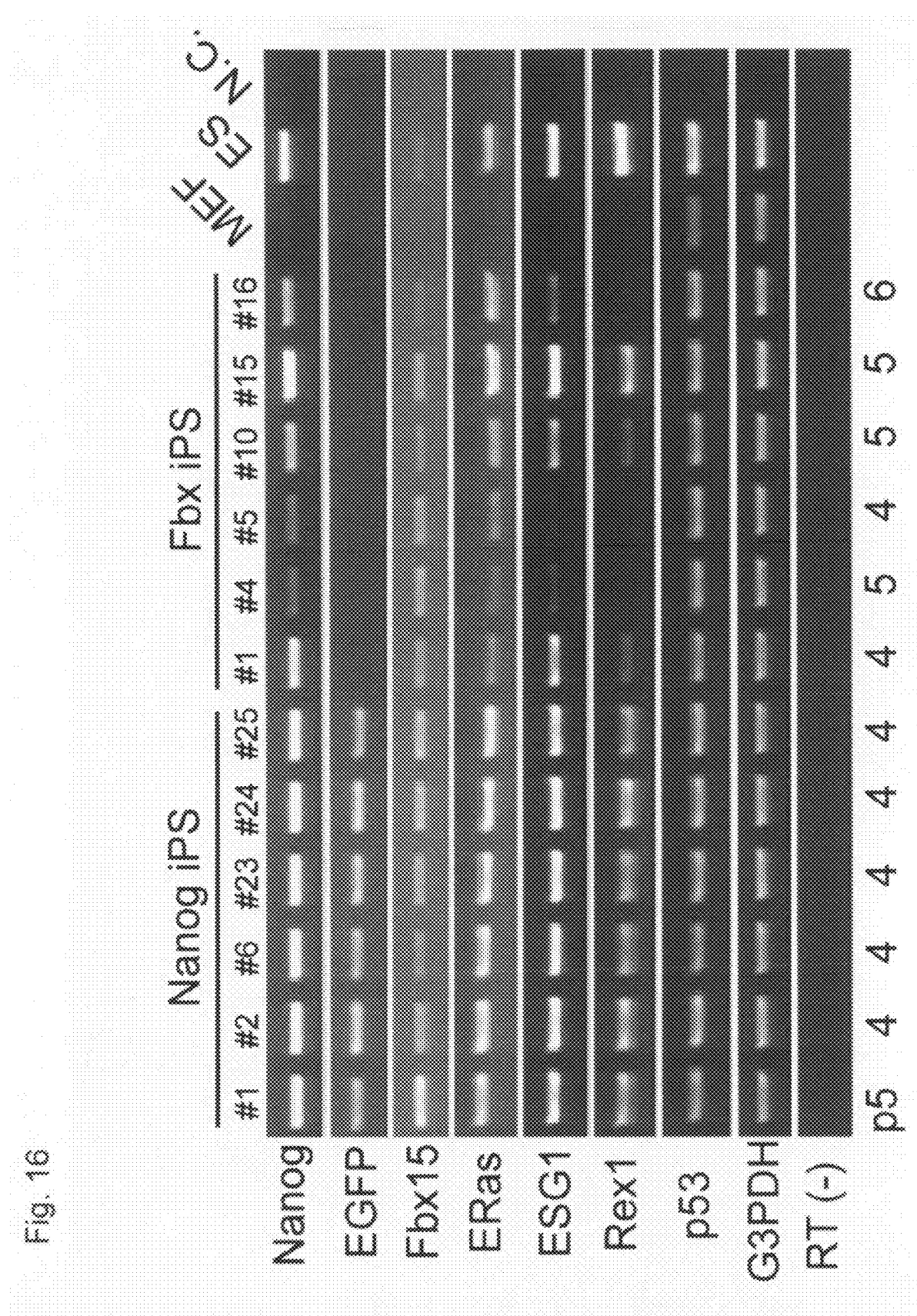
FIG. 16 shows gene expression profiles of iPS cells. Expression of the marker genes in MEFs, ES cells, iPS cells derived from Nanog-EGFP-IRES-Puro mouse MEFs (Nanog iPS, left), and iPS cells derived from Fbx15$^{\beta geo/\beta geo}$ mouse MEFs (Fbx iPS) were analyzed by RT-PCR. The numerical values at the bottom indicate the numbers of passages.
Figure 17:
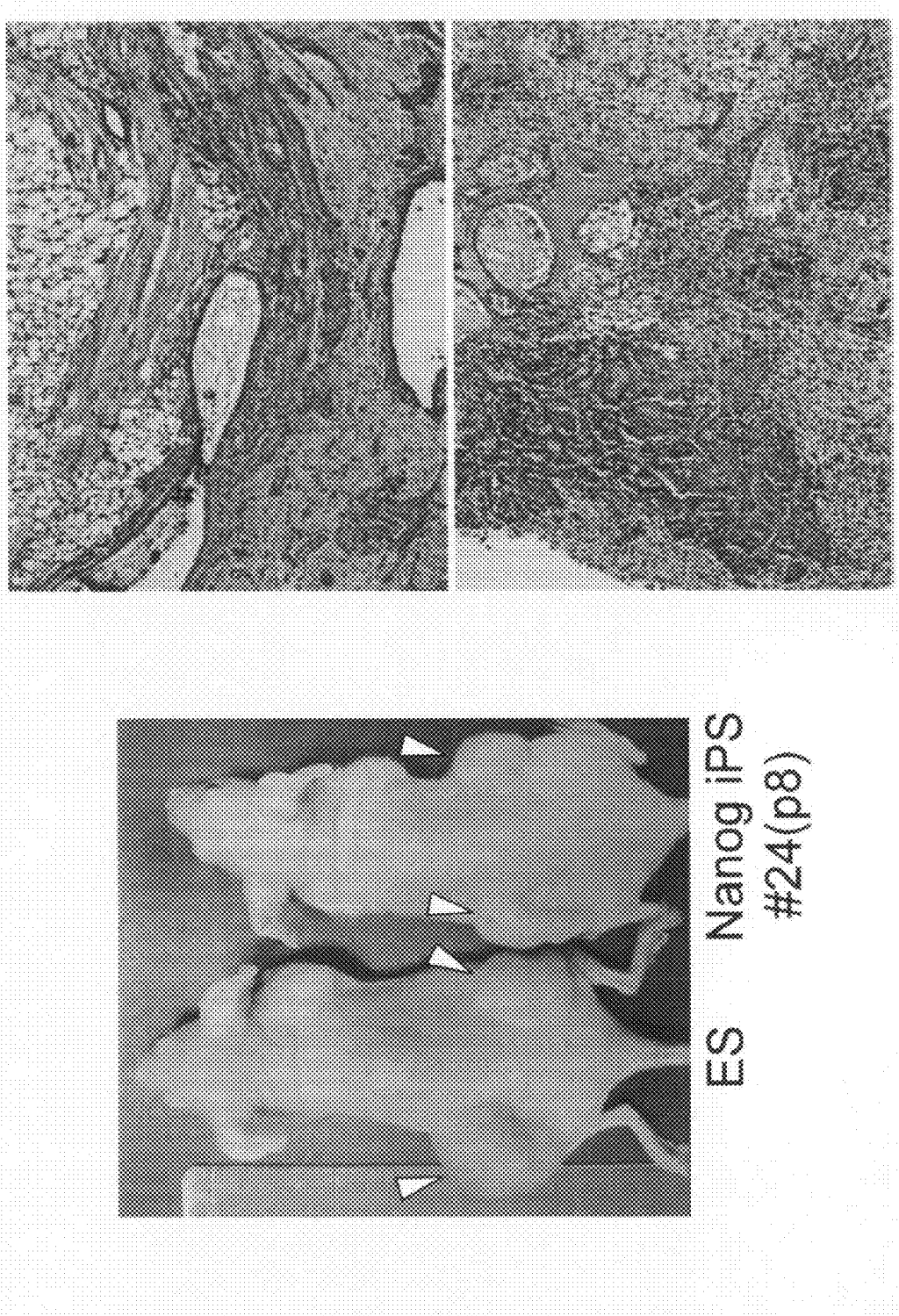
FIG. 17 shows teratoma formation from the Nanog iPS cells. 1,000,000 cells of each of ES cells or Nanog iPS cells were subcutaneously injected into the backs of nude mice, and the appearance of tumors formed after 3 weeks (left) and tissue images (right, H & E stained) are shown.
Figure 18:
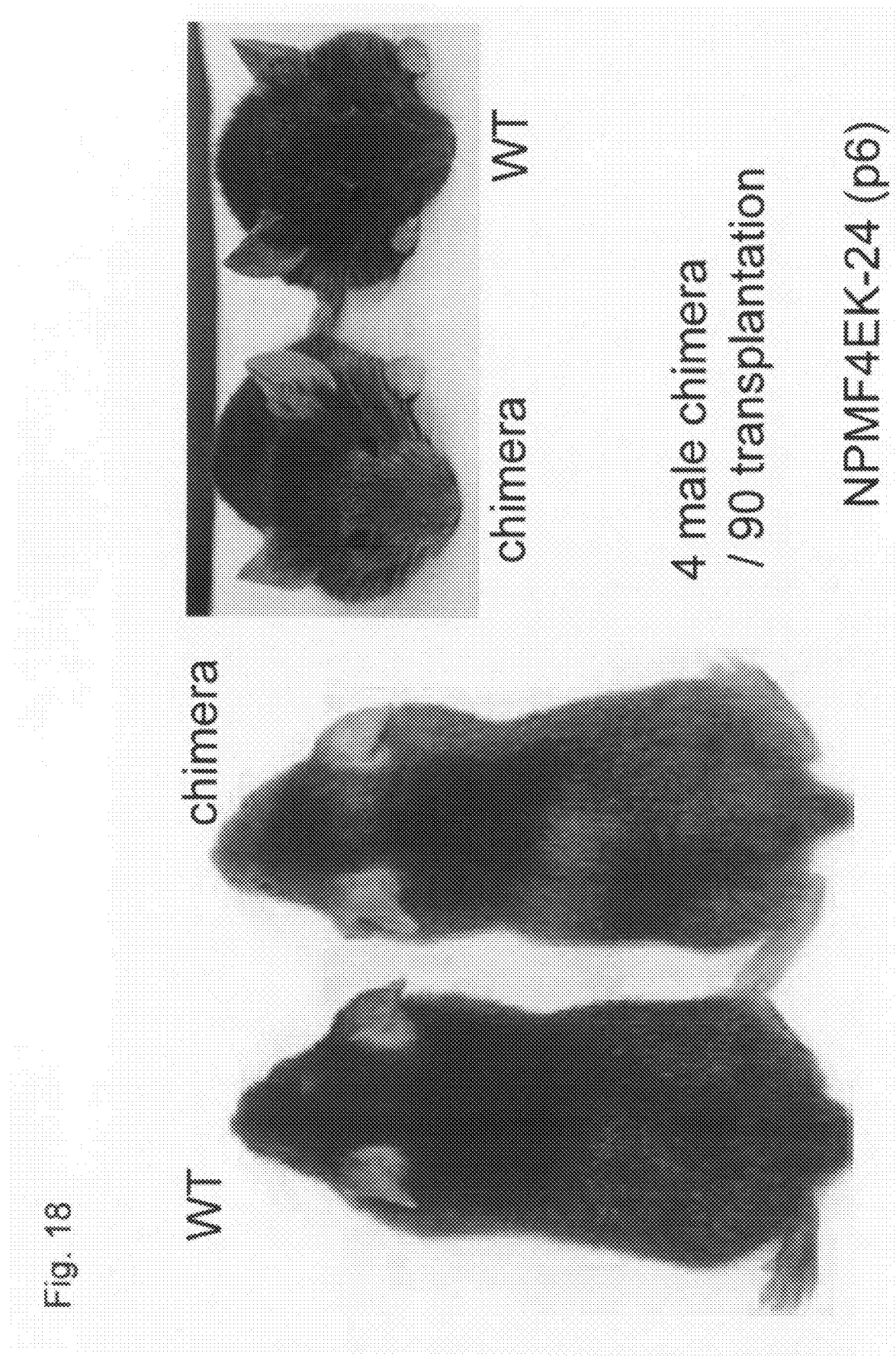
FIG. 18 shows preparation of chimeric mice with the Nanog iPS cells. The chimeric mice that were born after transplantation of the Nanog iPS cells (clone NPMF4EK-24, passaged 6 times) into the blastocysts. Four chimeric mice were born from 90 transplanted embryos.
Figure 19:
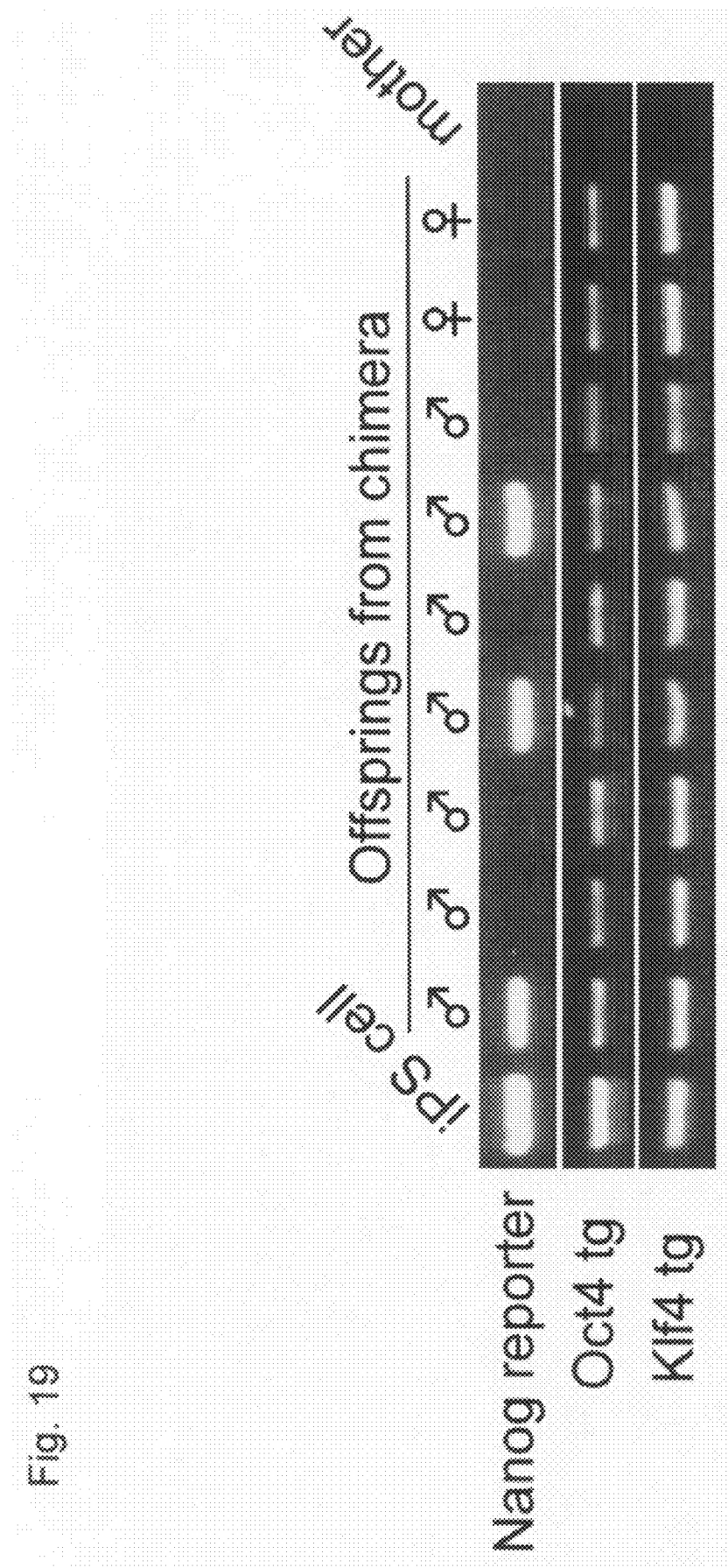
FIG. 19 shows germ-line transmission from the Nanog iPS cells. PCR analysis of genomic DNA of mice, born by mating of the chimeric mice shown in FIG. 18 and C57BL/6 mice, revealed the existence of transgenes of Oct¾ and Klf4 in all of the mice, thereby confirming germ-line transmission.

Studies were made as to whether iPS cells could be established with a reporter other than Fbx15-βgeo. *Escherichia. coli* artificial chromosome (BAC) containing the Nanog gene in the center was isolated, and then the GFP gene and the puromycin resistance gene were knocked in by recombination in *E. coli* (FIG. 12A). Subsequently, the above modified BAC was introduced into ES cells to confirm that the cells became GFP-positive in an undifferentiated state specific manner (data not shown). Then, these ES cells were transplanted in mouse blastocysts to create transgenic mice via chimeric mice. In these mice, GFP-positive cells were specifically observed in inner cell masses of the blastocysts or gonads of embryos at 13.5 days after fertilization (FIG. 12B). The gonads were removed from the embryos at 13.5 days after fertilization (hybrid of DBA, 129, and C57BL/6 mice), and MEFs were isolated. The isolated MEFs were confirmed to be GFP-negative (FIG. 13) by flow cytometry. These MEFs were retrovirally transduced with the 4 factors and subjected to puromycin selection, and as a result, a plural number of resistant colonies were obtained. Only about 10 to 20% of the colonies were GFP-positive. When the GFP-positive colonies were passaged, they gave morphology (FIG. 14) and proliferation (FIG. 15) similar to those of ES cells. Examination of the gene expression pattern revealed that the expression pattern was closer to that of ES cells as compared to the iPS cells isolated from Fbx15$^{\beta geo/\beta geo}$ MEFs by G418 selection (FIG. 16). When these cells were transplanted to nude mice, teratoma formation was induced, thereby the cells were confirmed to be iPS cells (FIG. 17). Further, chimeric mice were born by transplanting the iPS cells obtained by Nanog-GFP selection to the blastocysts of C57BL/6 mice (FIG. 18). When these chimeric mice were mated, germ-line transmission was observed (FIG. 19). In these iPS cells established by Nanog-GFP selection, which were closer to ES cells, the expressions of the 4 factors from the retroviruses were almost completely silenced, suggesting that self-replication was maintained by endogenous Oct3/4 and Sox2.

Example 8 iPS cells in 10 cm confluent were trypsinized and suspended in ES cell medium (the STO cells were removed by adhesion to a gelatin-coated dish for 10 to 20 minutes after the suspension). 2×10$^6$ cells were cultured for four days in a HEMA (2-hydroxyethyl methacrylate) coated *E. coli* culture dish as a suspension culture to form embryoid bodies (EBs) (day 1 to 4). On the 4th day of EB formation (day 4), all of the EBs were transferred to a 10-cm tissue culture dish, and cultured in ES cell medium for 24 hours to allow adhesion. After 24 hours (day 5), the medium was changed to an ITS/fibronectin-containing medium. The culture was performed for 7 days (medium was exchanged every 2 days), and nestin-positive cells were selected (cells of other pedigrees were dying to some extent in a culture under serum-free condition) (day 5 to 12). A2B5-positive cells were then induced. After 7 days (day 12), the cells were separated by trypsinization, and the remaining EBs were removed. $1 \times 10^5$ cells were seeded on a poly-L-ornithine/fibronectin-coated 24-well plate, and cultured for 4 days in an N2/bFGF-containing medium (medium was exchanged every 2 days) (day 12 to 16). After 4 days (day 16), the medium was changed to an N2/bFGF/EGF-containing medium, and the culture was continued for 4 days (medium was exchanged every 2 days) (day 16 to 20). After 4 days (day 20), the medium was changed to an N2/bFGF/PDGF-containing medium, and the culture was continued for 4 days (medium was exchanged every 2 days)(day 20 to 24). During this period (day 12 to 24), when the cells had increased excessively and reached confluent, they were passaged at appropriate times, and 1 to $2 \times 10^5$ cells were seeded (the number of the cells varied depending on the timing of the passage). After 4 days (day 24), the medium was changed to an N2/T3 medium, and the culture was continued for 7 days (day 24 to 31) with medium exchange every 2 days. On day 31, the cells were fixed and subjected to immunostaining. As a result, differentiation of the iPS cells into βIII tubulin-positive nerve cells, O4-positive oligodendrocytes, and GFAP-positive astrocytes was observed (FIG. 20).

Example 9

Figure 21:
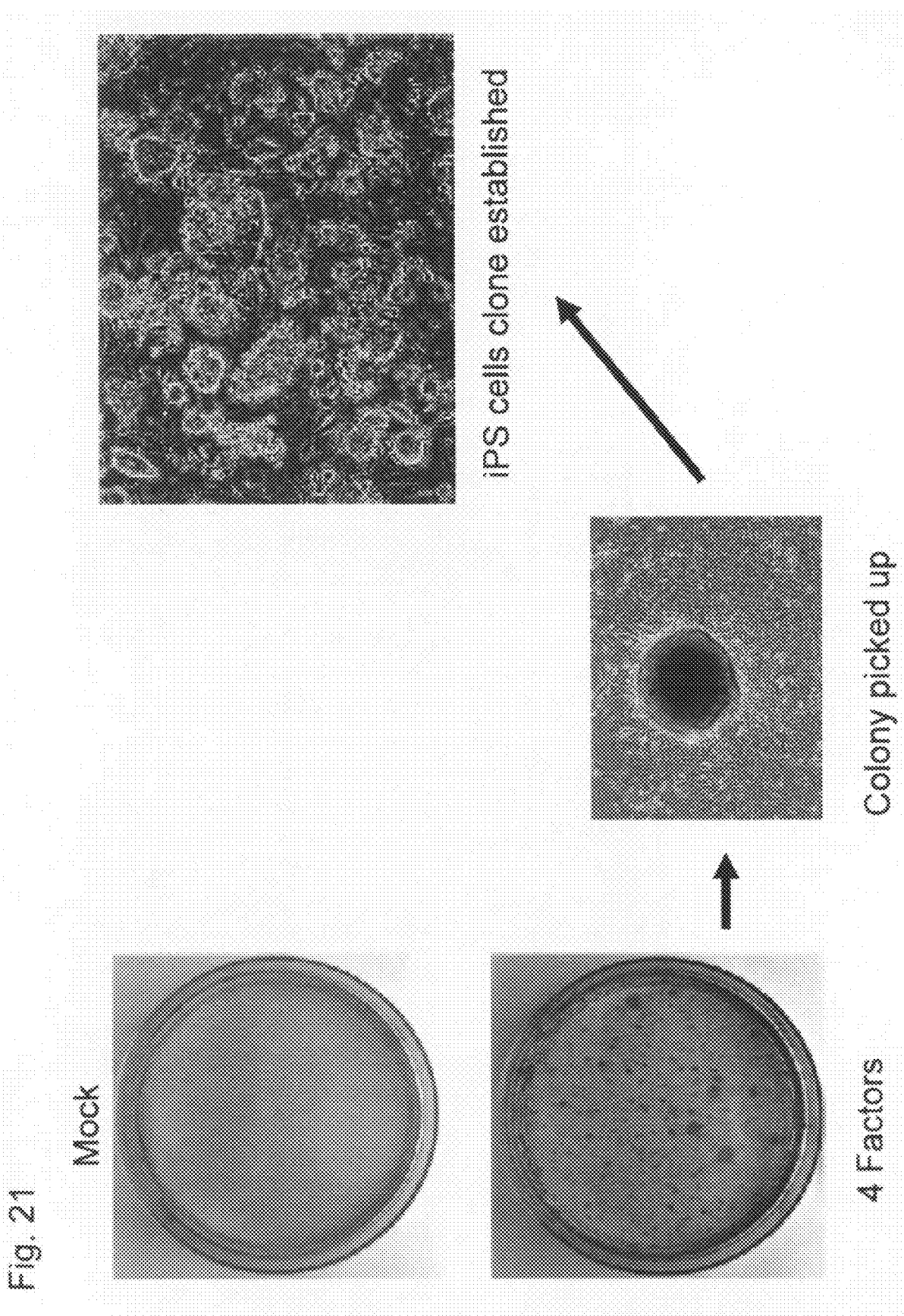
FIG. 21 depicts explanations of establishment of the iPS cells without using drug selection. MEFs at 10,000 to 100,000 cells per 10 cm dish were seeded, and the 4 factors were retrovirally transduced. No colony appeared in the control (Mock, left), whilst in the dish with the transduction by the 4 factors, swelling colonies similar to those of the iPS cells were obtained (center), as well as flat transformant colonies. When the cells were passaged, cells similar to the iPS cells were obtained (right).
Figure 22:
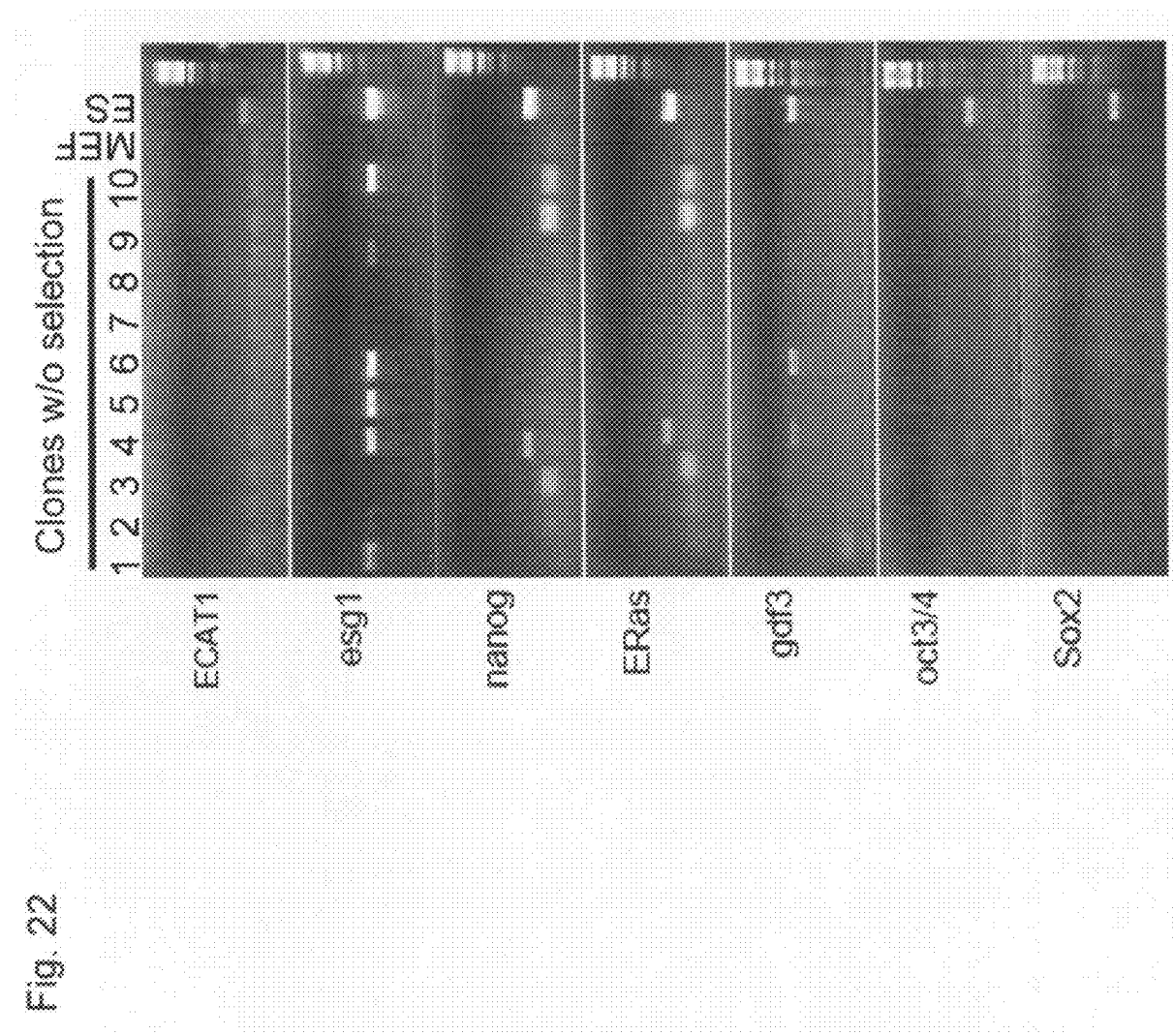
FIG. 22 shows gene expression profiles of cells established without using drug selection. RNA was extracted from the established cells shown in FIG. 21, and expression of the ES cell marker genes was analyzed by RT-PCR.

In order to establish iPS cells from arbitrary mouse somatic cells other than those derived from the Fbx15-βgeo knockin mouse, a method for the establishment without using drug selection was developed. Mouse embryo fibroblasts (MEFs) were cultured on a 10-cm dish (on STO feeder cells) in a number smaller than those used above (10,000, 50,000, or 100,000 cells), and a control DNA or the 4 factors were retrovirally transduced. When culture was performed for 2 weeks in the ES cell medium (without G418 selection), no colony formation was observed in the dish in which the control DNA was transduced, whilst in the dish in which the 4 factors were transduced, a plurality of compact colonies were formed as well as flat colonies considered to be transformed (FIG. 21). When 24 colonies were picked up from these colonies and culture was continued, ES cell-like morphology was observed. Gene expression profiles thereof were examined by RT-PCR, and as a result, the expression of Esg1, an ES cell marker, was observed in 7 clones. Induction of many ES cell markers such as Nanog, ERas, GDF3, Oct¾, and Sox2 was observed in clone 4, and therefore the cells were considered to be iPS cells (FIG. 22). The above results demonstrated that drug selection using Fbx15-βgeo knockin or the like was not indispensable for iPS cell establishment, and iPS cells could be established from arbitrary mouse-derived somatic cells. This also suggested the possibility that iPS cells could be established from somatic cells of a disease model mouse by the aforementioned technique.

Example 10

As cells from which iPS cells were induced, hepatocytes and gastric mucous cells being cells other than fibroblasts were examined. Hepatocytes were isolated from the liver of the $Fbx15^{\beta geo/\beta geo}$ mice by perfusion. These hepatocytes were retrovirally introduced with the 4 factors, and then subjected to G418 selection to obtain plural iPS cell colonies. As a result of gene expression pattern analysis using a DNA microarray, the iPS cells derived from the liver were found to be more similar to ES cells than the iPS cells derived from dermal fibroblasts or embryonic fibroblasts. iPS cells were obtained also from gastric mucous cells in the same manner as those from hepatocytes.

Example 11

PD98059 is an inhibitor of MAP kinase which suppresses proliferation of various differentiated cells. However, it is known to promote maintenance of undifferentiated status and proliferation of ES cells. Effects of PD98059 on iPS cell establishment were thus examined. MEFs established from a mouse having the selective markers of Nanog-EGFP-IRES-Puro were retrovirally introduced with the 4 factors and subjected to puromycin selection. When PD98059 was not added, the percentage of GFP-positive colonies was 8% of the iPS cell colonies obtained. However, in the group to which PD98059 (final concentration: 25 μM) was continuously added from the next day of the retroviral transfection, 45% of the colonies obtained were GFP-positive. The results were interpreted to be due to PD98059 promoting the proliferation of the GFP-positive iPS cells, which are closer to ES cells, whilst PD98059 suppressing the proliferation of the GFP-negative iPS cells or differentiated cells. From these results, PD98059 was demonstrated to be able to be used for establishment of the iPS cells closer to ES cells or establishment of iPS cells without using drug selection.

Example 12

A plasmid, containing the red fluorescence protein gene downstream from the mouse Oct¾ gene promoter and the hygromycin resistance gene downstream from the PGK promoter, was introduced by nucleofection into embryonic human dermal fibroblasts (HDFs) in which solute carrier family 7 (Slc7a1, NCBI accession number NM_007513) as a mouse ecotropic virus receptor was expressed by lentiviral transduction. Hygromycin selection was performed to establish strains with stable expression. 800,000 cells were seeded on the STO cells treated with mitomycin, and on the next day, Oct¾, Sox2, Klf4, and c-Myc (each derived from human) were retrovirally transduced into the cells. 24 colonies were picked up from those obtained after 3 weeks (FIG. 23, left), and transferred on a 24-well plate on which the STO cells were seeded and then cultured. After 2 weeks, one grown clone was passaged on a 6-well plate on which the STO cells were seeded and cultured. As a result, cells morphologically similar to ES cells were obtained (FIG. 23, right), suggesting that the cells were iPS cells. The mouse ES cell medium was used as every medium.

Example 13

Human adult dermal fibroblasts (adult HDFs) were transduced with Slc7a1 (mouse retroviral receptor) by using lentivirus, and the resulting cells were seeded on 800,000 feeder cells (mitomycin-treated STO cells). The genes were retrovirally transduced as the following combinations.
1. Oct¾, Sox2, Klf4, c-Myc, TERT, and SV40 Large T antigen
2. Oct¾, Sox2, Klf4, c-Myc, TERT, HPV16 E6
3. Oct¾, Sox2, Klf4, c-Myc, TERT, HPV16 E7
4. Oct¾, Sox2, Klf4, c-Myc, TERT, HPV16 E6, HPV16 E7
5. Oct¾, Sox2, Klf4, c-Myc, TERT, Bmil (Oct3/4, Sox2, Klf4, c-Myc and TERT were derived from human, and Bmil was derived from mouse)

Figure 24:
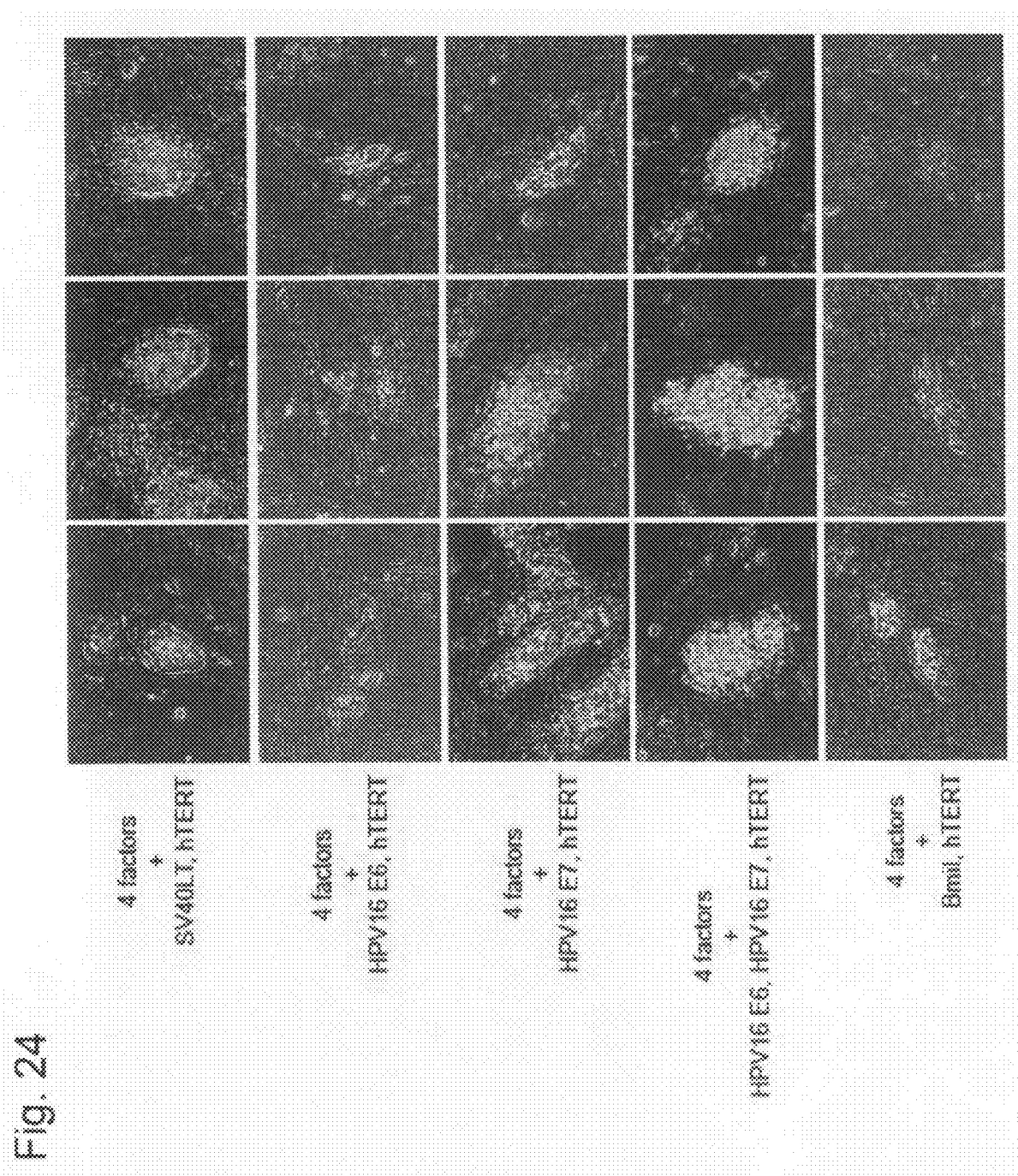
FIG. 24 shows establishment of the iPS cells from human adult dermal fibroblasts. The factors mentioned in the left column were transduced retrovirally into human adult dermal fibroblasts infected with the mouse retroviral receptor with lentivirus. The photographs shows phase contrast images (object×10) on day 8 after the viral infection.

The culture was continued under the culture conditions for mouse ES cells without drug selection. As a result, colonies considered to be those of iPS cells emerged on the 8th day after the virus transfection on the dish in which the factors were introduced according to Combination 1 (FIG. 24). iPS cell-like colonies also emerged with the other combinations (2 to 5), although they were not as apparent when compared to Combination 1. When only the 4 factors were transduced, no colonies emerged.

INDUSTRIAL APPLICABILITY

By using the nuclear reprogramming factor provided by the present invention, reprogramming of differentiated cell nuclei can be conveniently and highly reproducibly induced without using embryos or ES cells, and induced pluripotent stem cells as undifferentiated cells having differentiation ability, pluripotency and growth ability similar to those of ES cells can be established.

What is claimed is:

1. A nuclear reprogramming factor comprising an isolated Oct family gene, an isolated Klf family gene, and an isolated Myc family gene.

2. The factor according to claim 1, which comprises each of the following three genes: Oct3/4, Klf4, and c-Myc.

3. The factor according to claim 1, which further comprises an isolated Sox family gene.

4. The factor according to claim 3, wherein the Sox family gene is Sox2 gene.

5. The factor according to claim 1, further comprising a cytokine.

6. The factor according to claim 5, wherein the cytokine is basic fibroblast growth factor (bFGF) and/or stem cell factor (SCF).

7. The factor according to claim 1, which further comprises isolated TERT gene.

8. The factor according to claim 1, which further comprises one or more of the following isolated genes: SV40 Large T antigen, HPV16 E6, HPV16 E7, and Bmil.

9. The factor according to claim 1, which further comprises one or more of the following isolated genes: Fbx15, Nanog, ERas, ECAT15-2, Tcl, and β-catenin.

10. The factor according to claim 1, which further one or more of the following isolated genes: ECAT1, Esg1, Dnmt3L, ECAT8, Gdf3, Sox15, ECAT15-1, Fthl17, Sall4, Rex1, UTF1, Stella, Stat3, and Grb2.

11. A nuclear reprogramming factor comprising an isolated Oct family gene, an isolated Klf family gene, and a cytokine.

12. The factor according to claim 11, wherein the cytokine is bFGF and/or SCF.

13. The factor according to claim 11, which comprises each of the following two genes: Oct3/4 and Klf4.

14. The factor according to claim 11, which further comprises an isolated Sox family gene.

15. The factor according to claim 14, wherein the Sox family gene is Sox2 gene.

16. The factor according to claim 14, wherein the Oct family gene is an Oct3/4 gene, the Klf family gene is a Klf4gene, the Sox family gene is Sox2gene and the cytokine is bFGF.

17. The factor according to claim 2, wherein an L-Myc or N-Myc gene is substituted for the c-Myc gene.

18. The factor according to claim 2, wherein a Klf2 gene is substituted for the Klf4 gene.

19. The factor according to claim 4, wherein a Sox1, Sox3, Sox15 or Sox17 gene is substituted for the Sox2 gene.

20. The factor according to claim 2, which consists of each of the following three genes: Oct3/4, Klf4, and c-Myc.

21. The factor according to claim 2, further comprising Sox2 gene.

22. The factor according to claim 21, which consists of each of the following four genes: Oct3/4, Klf4, c-Myc, and Sox2.

23. The factor according to claim 21, wherein an L-Myc or N-Myc gene is substituted for the c-Myc gene.

24. The factor according to claim 23, which consists of each of the following four genes: Oct3/4, Klf4, L-Myc and Sox2.

25. The factor according to claim 16, which consists of Oct3/4 gene, Klf4 gene, Sox2 gene and bFGF.

* * * * *

UNITED STATES PATENT AND TRADEMARK OFFICE
CERTIFICATE OF CORRECTION

PATENT NO. : 8,048,999 B2
APPLICATION NO. : 12/086479
DATED : November 1, 2011
INVENTOR(S) : Shinya Yamanaka et al.

It is certified that error appears in the above-identified patent and that said Letters Patent is hereby corrected as shown below:

Title page, Col. 2, line 5, under Other Publications, change "Ooctyes," to --Oocytes,--.

Title page, Col. 2, line 13, under Other Publications, change "Nat1 . Acad." to --Natl. Acad.--.

At Page 2, Col. 2, line 74, under Foreign Patent Documents, change "WO 2609/" to --WO 2009/--.

At Page 3, Col. 1, line 3, under Other Publications, change "Pluriportent" to --Pluripotent--.

At Page 4, Col. 2, line 18, under Other Publications, change "miroRNA" to --microRNA--.

At Page 5, Col. 2, line 35, under Other Publications, change "Biochemisny" to --Biochemistry--.

At Page 6, Col. 1, line 33, under Other Publications, change "SI4" to --S14--.

At Page 6, Col. 2, line 18, under Other Publications, change "Nat!" to --Natl.--.

At Page 7, Col. 1, line 45, under Other Publications, change "Pluripotericy" to --Pluripotency--.

At Page 9, Col. 1, line 1, under Other Publications, change "Researchr." to --Research.--.

At Page 9, Col. 1, line 42, under Other Publications, change "lmmunol." to --Immunol.--.

At Col. 1, line 60, change "of" to --of:--.

At Col. 2, line 57, change "Bmil," to --Bmi1,--.

At Col. 9, line 6, change "Bmil." to --Bmi1.--.

At Col. 9, line 12, change "Bmil" to --Bmi1--.

At Col. 9, line 19, change "Bmil" to --Bmi1--.

At Col. 10, line 39, change "form" to --from--.

At Col. 15, line 65, change "withdrawal" to --with withdrawal--.

At Col. 17-18 (Table 6), line 2, change "GTC" to --CTC--.

At Col. 22, line 67, change "Bmil" to --Bmi1--.

At Col. 23, line 2, change "Bmil" to --Bmi1--.

At Col. 33, line 45, in Claim 8, change "Bmil." to --Bmi1.--.

At Col. 33, line 43, in Claim 9, change "Tcl," to --Tcl1,--.

Signed and Sealed this
Fourth Day of September, 2012

David J. Kappos
*Director of the United States Patent and Trademark Office*

CERTIFICATE OF CORRECTION (continued)
U.S. Pat. No. 8,048,999 B2

At Col. 33, line 49, in Claim 10, change "further" to --further comprises--.

At Col. 33, line 51, in Claim 10, change "Fthll7," to --Fthl17,--.

At Col. 34, line 34, in Claim 16, change "Klf4gene," to --Klf4 gene,--.

At Col. 34, line 34, in Claim 16, change "Sox2gene" to --Sox2 gene--.